(12) United States Patent
Kobayashi

(10) Patent No.: US 11,678,875 B2
(45) Date of Patent: Jun. 20, 2023

(54) METHODS AND APPARATUS FOR RADIALLY COMPRESSIVE SHAPE MEMORY IMPLANTS

(71) Applicant: DEPUY SYNTHES PRODUCTS, INC., Raynham, MA (US)

(72) Inventor: Kenneth Kobayashi, Downingtown, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 32 days.

(21) Appl. No.: 17/241,760

(22) Filed: Apr. 27, 2021

(65) Prior Publication Data

US 2022/0338869 A1    Oct. 27, 2022

(51) Int. Cl.
| | | |
|---|---|---|
| *A61B 17/00* | (2006.01) | |
| *A61B 17/80* | (2006.01) | |
| *A61B 17/68* | (2006.01) | |
| *A61B 17/064* | (2006.01) | |

(52) U.S. Cl.
CPC ...... *A61B 17/0642* (2013.01); *A61B 17/0644* (2013.01); *A61B 17/8014* (2013.01); *A61B 17/8019* (2013.01); *A61B 17/8061* (2013.01); *A61B 17/8085* (2013.01); *A61B 2017/00867* (2013.01); *A61B 2017/0641* (2013.01); *A61B 2017/0645* (2013.01); *A61B 2017/681* (2013.01)

(58) Field of Classification Search
CPC ............ A61B 17/8014; A61B 17/8019; A61B 17/0642; A61B 17/8061; A61B 17/8085; A61B 17/0644; A61B 2017/00862; A61B 2017/00867; A61B 2017/681; A61B 2017/0641; A61B 2017/0645
USPC .................................................. 606/75, 282
See application file for complete search history.

(56) References Cited

U.S. PATENT DOCUMENTS

| | | | |
|---|---|---|---|
| 5,201,737 A * | 4/1993 | Leibinger | A61B 17/8085 606/280 |
| 5,246,443 A | 9/1993 | Mai | |
| 5,785,713 A | 7/1998 | Jobe | |
| 6,179,839 B1 | 1/2001 | Weiss et al. | |
| 8,062,297 B2 | 11/2011 | Faillace et al. | |
| 10,117,647 B2 | 11/2018 | Cheney | |
| 10,292,743 B2 | 5/2019 | Taylor et al. | |

(Continued)

OTHER PUBLICATIONS

International Search Report for PCT/IB2022/053430, dated Sep. 12, 2022, PCT Application Counterpart to U.S. Appl. No. 17/241,760.

*Primary Examiner* — Marcela I. Shirsat
(74) *Attorney, Agent, or Firm* — Christopher L. Makay

(57) ABSTRACT

A radially compressive implant, which includes a central vertical axis, is configured to transition between a natural shape and an insertion shape. A transition of the implant from the natural shape to the insertion shape facilitates the implant storing energy deliverable radially relative to the central vertical axis. A transition of the implant from the insertion shape toward the natural shape facilitates the implant delivering the energy stored therein radially relative to the central vertical axis. An implant delivery device in an implant engagement position is configured to engage the implant and constrain the implant in the insertion shape. The implant delivery device in an implant release position is configured to release the implant.

22 Claims, 40 Drawing Sheets

(56) References Cited

U.S. PATENT DOCUMENTS

| | | |
|---|---|---|
| 2005/0216008 A1* | 9/2005 | Zwirnmann ............ A61B 17/68 |
| | | 606/915 |
| 2009/0264923 A1 | 10/2009 | Sater |
| 2015/0230843 A1* | 8/2015 | Palmer ............... A61B 17/7291 |
| | | 606/331 |
| 2016/0166252 A1 | 6/2016 | Viola et al. |
| 2017/0181779 A1 | 6/2017 | Leither et al. |
| 2017/0209190 A1 | 7/2017 | Goodwin, Jr. et al. |
| 2018/0140312 A1 | 5/2018 | Sikora et al. |
| 2018/0310972 A1 | 11/2018 | Anding et al. |
| 2019/0110824 A1* | 4/2019 | Kobayashi ......... A61B 17/8085 |
| 2019/0117219 A1 | 4/2019 | Ritz et al. |
| 2020/0229813 A1 | 7/2020 | Seykora et al. |
| 2020/0281633 A1 | 9/2020 | Rogers |

\* cited by examiner

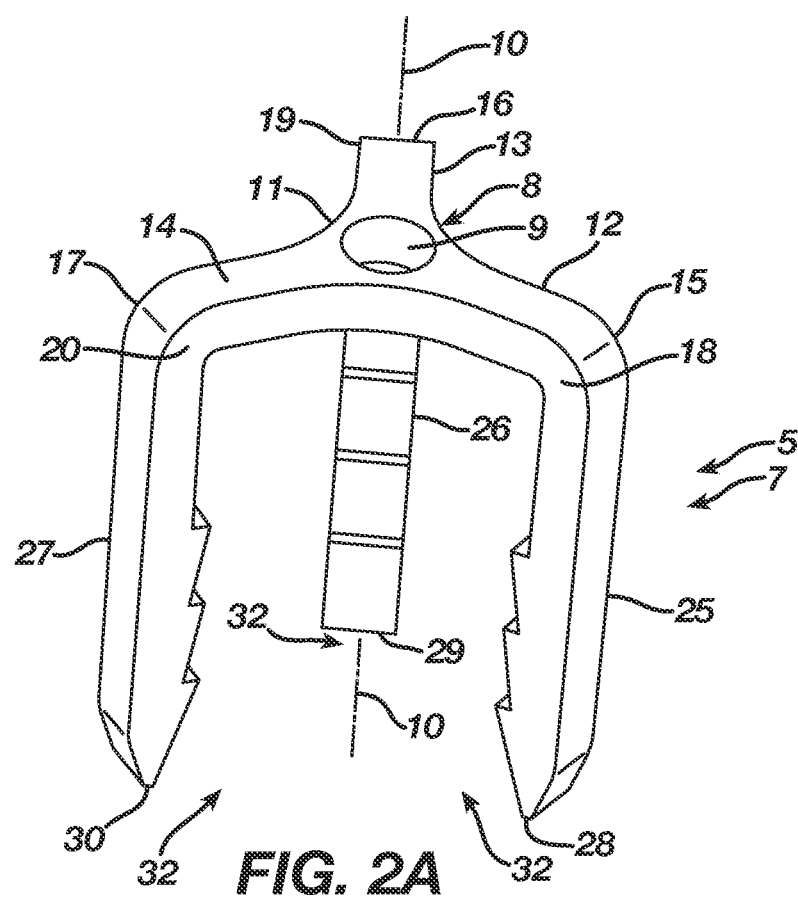
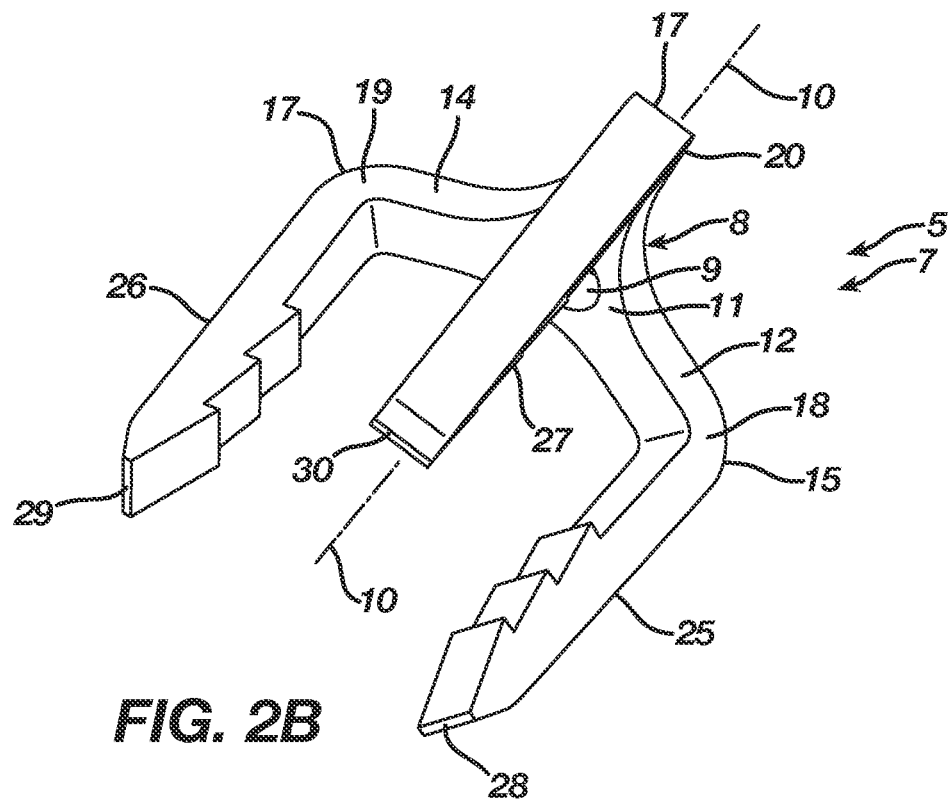

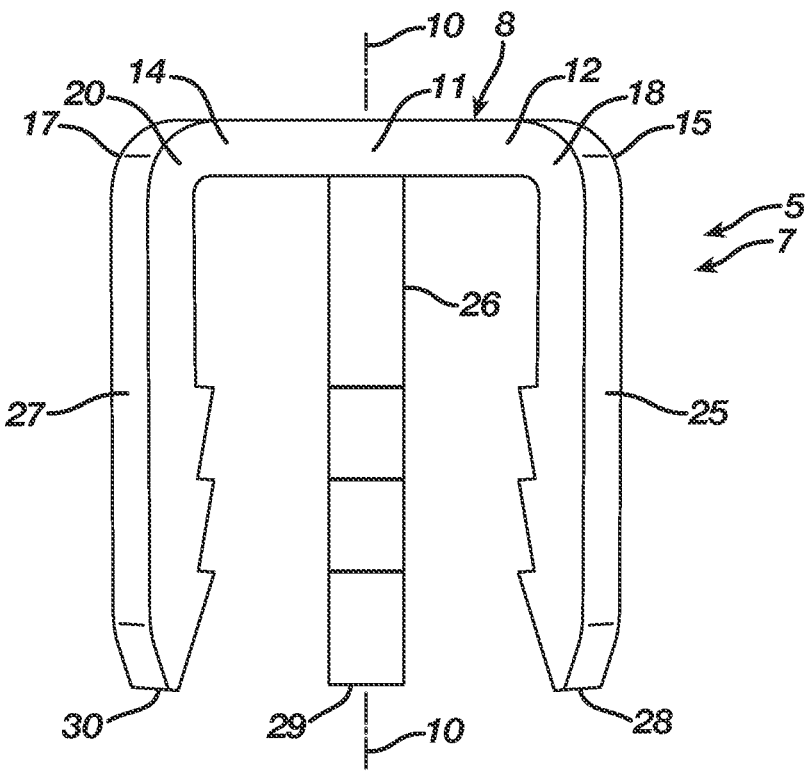
FIG. 2C
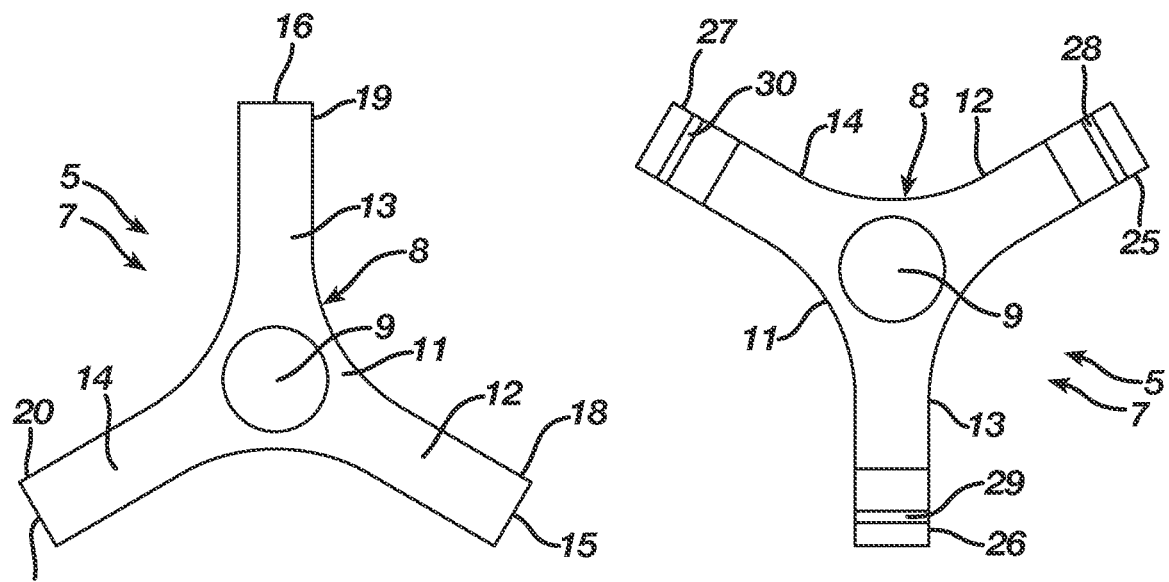
FIG. 2D
FIG. 2E

METHODS AND APPARATUS FOR RADIALLY COMPRESSIVE SHAPE MEMORY IMPLANTS

BACKGROUND OF THE INVENTION

1. Field of the Invention

The present invention relates generally to shape memory implants and the implantation thereof using implant delivery devices and, more particularly, but not way of limitation, to radially compressive shape memory implants and implant delivery devices configured for loading with the radially compressive shape memory implants and for subsequent delivery of the radially compressive shape memory implants into bone, bones, or bone pieces utilizing the implant delivery devices.

2. Description of the Related Art

Shape memory materials (e.g., nitinol (nickel-titanium)) due to their superelastic or temperature dependent properties currently are employed in the manufacture of surgical implants designed to affix bone, bones, or bone pieces; such as, for example, surgical staples and surgical plates. A surgical implant manufactured from a shape memory material with superelastic or temperature dependent properties typically includes a natural shape. Nevertheless, the surgical implant may be deformed from its natural shape to an insertion shape whereby the surgical implant stores energy deliverable to a bone, bones, or bone pieces. The surgical implant when deformed to its insertion shape typically loads on a mechanical constraint that prevents transition of the surgical implant from its insertion shape to its natural shape. The surgical implant once loaded on a mechanical constraint is deliverable to a bone, bones, or bone pieces. After the surgical implant is delivered and then released from the mechanical constraint, the surgical implant attempts to transition from its insertion shape to its natural shape such that the surgical implant exerts a compressive force to the bone, bones, or bone pieces.

A surgical staple typically includes a bridge with one or more transition sections, one or more legs extending from a first end of the bridge, and one or more legs extending from a second end of the bridge. The surgical staple includes a natural shape where the one or more transition sections maintain the one or more legs at the first end and the one or more legs at the second end in a natural position, which normally is converging. The surgical staple, however, deforms from its natural shape to an insertion shape where the one or more transition sections move the one or more legs at the first end and the one or more legs at the second end to an insertion position, which normally is substantially parallel. The surgical staple once deformed to its insertion shape typically loads on a mechanical constraint prior to the delivery of the surgical staple into a bone, bones, or bone pieces. After the surgical staple is delivered and released from the mechanical constraint, the surgical staple, due to its superelastic or temperature dependent properties, attempts to transition from its insertion shape to its natural shape such that the surgical staple exerts a compressive force to the bone, bones, or bone pieces.

A surgical plate typically includes a transition section, one or more apertures at a first end of the surgical plate configured to receive screws therethrough, and one or more apertures at a second end of the surgical plate configured to receive screws therethrough. The surgical plate includes a natural shape where the transition section maintains the first end of the surgical plate and the second end of the surgical plate at a first distance. The surgical plate, however, deforms from its natural shape to an insertion shape where the transition section moves the first end of the surgical plate and the second end of the surgical plate to a second distance greater than the first distance. The surgical plate once deformed to its insertion shape typically loads on a mechanical constraint prior to the delivery of the surgical plate onto a bone, bones, or bone pieces. After the surgical plate is delivered, secured to the bone, bones, or bone pieces via screws inserted through the apertures at the first and second ends, and then released from the mechanical constraint, the surgical plate, due to its superelastic or temperature dependent properties, attempts to transition from its insertion shape to its natural shape such that the surgical plate exerts a compressive force to the bone, bones, or bone pieces.

While shape memory material surgical implants, such as the above-described surgical staples and surgical plates, in most instances operate adequately in the healing of bone, bones, or bone pieces, the surgical implants, which generate linear compressive forces, are less than ideal for certain orthopedic surgical procedures, such as, for example, carpal fusions and the like that require multiple bone segments be drawn into a central point and then held until a fusion thereof. Although multiple linear surgical implants can be used to hold multiple bone segments at a central point until a fusion thereof, the results of the fusion often are less than optimal. Accordingly, a shape memory implant configured to radially compress multiple bone segments until a fusion thereof will provide an improvement in certain orthopedic surgical procedures, such as, for example, carpal fusions and the like.

SUMMARY OF THE INVENTION

In accordance with the present invention, a radially compressive implant, which includes a central vertical axis, is transitionable between a natural shape and an insertion shape. A transition of the implant from the natural shape to the insertion shape facilitates the implant storing energy deliverable radially relative to the central vertical axis. A transition of the implant from the insertion shape toward the natural shape facilitates the implant delivering the energy stored therein radially relative to the central vertical axis. The implant, once implanted in bone, bones, or bone pieces, attempts to transition from the insertion shape to the natural shape whereby the implant delivers the energy stored therein to the bone, bones, or bone pieces in order to affix the bone, bones, or bone pieces and promote a healing thereof. The implant during the attempted transition thereof from the insertion shape to the natural shape continuously and radially compresses the bone, bones, or bone pieces to promote fusion thereof. The radially compressive implant may form an orthopedic fixation system when used in combination with an implant delivery device.

The radially compressive implant includes a bridge disposed about the central vertical axis of the implant. The bridge includes a center section, a first bridge segment, a second bridge, and a third bridge segment. The first bridge segment extends from the center section to an end thereof, the second bridge segment extends from the center section to an end thereof, and the third bridge segment extends from the center section to an end thereof. The bridge includes a first transition section located in the first bridge segment, a second transition section located in the second bridge segment, and a third transition section located in the third bridge segment. The radially compressive implant includes a first fixation member extending from the first bridge segment, a second fixation member extending from the second bridge segment, and a third fixation member extending from the third bridge segment.

A transition of the implant from the natural shape to the insertion shape includes a deformation of the first transition section, the second transition section, and the third transition section that stores energy therein. When undergoing deformation, the first transition section, the second transition section, and the third transition section move the bridge from a natural form to an insertion form. Concurrently, the first transition section moves the first fixation member, the second transition section moves the second fixation member, and the third transition section moves the third fixation member linearly away from the central axis. The first fixation member, the second fixation member, and the third fixation member accordingly diverge relative to the central axis as the first fixation member, the second fixation member, and the third fixation member progress from a natural position to an insertion position, thereby facilitating the implant storing energy deliverable radially relative to the central vertical axis.

A transition of the implant from the insertion shape toward the natural shape includes the first transition section, the second transition section, and the third transition section delivering the energy stored therein. In delivering the stored energy, the first transition section, the second transition section, and the third transition section move the bridge from the insertion form toward the natural form. Concurrently, the first transition section moves the first fixation member, the second transition section moves the second fixation member, and the third transition section moves the third fixation member linearly toward the central axis. The first fixation member, the second fixation member, and the third fixation member accordingly converge relative to the central axis as the first fixation member, the second fixation member, and the third fixation member progress from the insertion position toward the natural position, thereby facilitating the implant delivering the energy stored therein radially relative to the central vertical axis.

The first bridge segment, the second bridge segment, and the third bridge segment preferably are symmetrical in that the first bridge segment, the second bridge segment, and the third bridge segment radially extend from the center section and are spaced about the central vertical axis substantially equidistant. Moreover, the first bridge segment, the second bridge segment, and the third bridge segment are substantially, dimensionally identical. In accordance with the symmetry of the first bridge segment, the second bridge segment, and the third bridge segment, the first fixation member, the second fixation member, and the third fixation member preferably are spaced apart substantially equidistant about the central vertical axis in both the natural position and the insertion position. The first fixation member, the second fixation member, and the third fixation member in the natural position reside from the central vertical axis at a first distance, whereas the first fixation member, the second fixation member, and the third fixation member in the insertion position reside from the central vertical axis at a second distance that is greater than the first distance.

In a first embodiment of the radially compressive implant, the implant defines an aperture at the central vertical axis thereof that facilitates engagement of the implant with an implant delivery device. More particularly, the bridge of the implant at the center section defines the aperture. The first transition section is located in the first bridge segment at the end thereof, the second transition section is located in the second bridge segment at the end thereof, and the third transition section is located in the third bridge segment at the end thereof. As such, the first fixation member extends from the first transition section of the first bridge segment at the end thereof, the second fixation member extends from the second transition section of the second bridge segment at the end thereof, and the third fixation member extends from the third transition section of the third bridge segment at the end thereof.

A transition of the implant according to the first embodiment from the natural shape to the insertion shape includes a deformation of the first transition section, the second transition section, and the third transition section that stores energy therein. When undergoing deformation, the first transition section, the second transition section, and the third transition section move the bridge from the natural form to the insertion form. Concurrently, the first transition section moves the first fixation member, the second transition section moves the second fixation member, and the third transition section moves the third fixation member linearly away from the central axis. The first fixation member, the second fixation member, and the third fixation member accordingly diverge relative to the central axis as the first fixation member, the second fixation member, and the third fixation member progress from the natural position to the insertion position, thereby facilitating the implant storing energy deliverable radially relative to the central vertical axis.

A transition of the implant according to the first embodiment from the insertion shape toward the natural shape includes the first transition section, the second transition section, and the third transition section delivering the energy stored therein. In delivering the stored energy, the first transition section, the second transition section, and the third transition section move the bridge from the insertion form toward the natural form. Concurrently, the first transition section moves the first fixation member, the second transition section moves the second fixation member, and the third transition section moves the third fixation member linearly toward the central axis. The first fixation member, the second fixation member, and the third fixation member accordingly converge relative to the central axis as the first fixation member, the second fixation member, and the third fixation member progress from the insertion position toward the natural position, thereby facilitating the implant delivering the energy stored therein radially relative to the central vertical axis.

The first fixation member of the implant according to the first embodiment includes a first leg extending from the first transition section of the first bridge segment at the end. Likewise, the second fixation member includes a second leg extending from the second transition section of the second bridge segment at the end, and the third fixation member includes a third leg extending from the third transition section of the third bridge segment at the end.

A transition of the implant according to the first embodiment from the natural shape to the insertion shape includes a deformation of the first transition section, the second transition section, and the third transition section that stores energy therein. When undergoing deformation, the first transition section, the second transition section, and the third transition section move the bridge from the natural form to the insertion form. Concurrently, the first transition section moves the first leg, the second transition section moves the second leg, and the third transition section moves the third leg linearly away from the central axis. The first leg, the second leg, and the third leg accordingly diverge relative to the central axis as the first leg, the second leg, and the third leg progress from the natural position to the insertion position, thereby facilitating the implant storing energy deliverable radially relative to the central vertical axis.

A transition of the implant according to the first embodiment from the insertion shape toward the natural shape includes the first transition section, the second transition section, and the third transition section delivering the energy stored therein. In delivering the stored energy, the first transition section, the second transition section, and the third transition section move the bridge from the insertion form toward the natural form. Concurrently, the first transition section moves the first leg, the second transition section moves the second leg, and the third transition section moves the third leg linearly toward the central axis. The first leg, the second leg, and the third leg accordingly converge relative to the central axis as the first leg, the second leg, and the third leg progress from the insertion position toward the natural position, thereby facilitating the implant delivering the energy stored therein radially relative to the central vertical axis.

In a second embodiment of the radially compressive implant, the implant defines an aperture at the central vertical axis thereof that facilitates engagement of the implant with an implant delivery device. More particularly, the bridge of the implant at the center section defines the aperture. The bridge further includes a fourth bridge segment extending from the center section to an end thereof and a fourth transition section located in the fourth bridge segment at the end thereof. The first bridge segment, the second bridge segment, the third bridge segment, and the fourth bridge segment are spaced symmetrically about the central vertical axis of the implant. Moreover, a fourth fixation member extends from the fourth transition section of the fourth bridge segment at the end thereof.

A transition of the implant according to the second embodiment from the natural shape to the insertion shape includes a deformation of the first transition section, the second transition section, the third transition section, and the fourth transition section that stores energy therein. When undergoing deformation, the first transition section, the second transition section, the third transition section, and the fourth transition section move the bridge from the natural form to the insertion form. Concurrently, the first transition section moves the first fixation member, the second transition section moves the second fixation member, the third transition section moves the fourth fixation member, and the fourth transition section moves the fourth fixation member linearly away from the central axis. The first fixation member, the second fixation member, the third fixation member, and the fourth fixation member accordingly diverge relative to the central axis as the first fixation member, the second fixation member, the third fixation member, and the fourth fixation member progress from the natural position to the insertion position, thereby facilitating the implant storing energy deliverable radially relative to the central vertical axis.

A transition of the implant according to the second embodiment from the insertion shape toward the natural shape includes the first transition section, the second transition section, the third transition section, and the fourth transition section delivering the energy stored therein. In delivering the stored energy, the first transition section, the second transition section, the third transition section, and the fourth transition section move the bridge from the insertion form toward the natural form. Concurrently, the first transition section moves the first fixation member, the second transition section moves the second fixation member, the third transition section moves the third fixation member, and the fourth transition section linearly toward the central axis. The first fixation member, the second fixation member, the third fixation member, and the fourth fixation member accordingly converge relative to the central axis as the first fixation member, the second fixation member, the third fixation member, and the fourth fixation member progress from the insertion position toward the natural position, thereby facilitating the implant delivering the energy stored therein radially relative to the central vertical axis.

In a third embodiment of the radially compressive implant, the implant defines an aperture at the central vertical axis thereof. More particularly, the bridge of the implant at the center section defines the aperture. The first bridge segment includes an opening adjacent the end thereof, the second bridge segment includes an opening adjacent the end thereof, and the third bridge segment includes an opening adjacent the end thereof. The first transition section is located in the first bridge segment between the center section and the opening of the first bridge segment, the second transition section is located in the second bridge segment between the center section and the opening of the second bridge segment, and the third transition section is located in the third bridge segment between the center section and the opening of the third bridge segment. The first fixation member inserts through the opening of the first bridge segment at the end thereof, the second fixation member inserts through the opening of the second bridge segment at the end thereof, and the third fixation member inserts through the opening of the third bridge segment at the end thereof. The first bridge segment, the second bridge segment, and the third bridge segment at the ends thereof each define an interlock adapted to facilitate engagement of the implant with an implant delivery device.

A transition of the implant from the natural shape to the insertion shape includes a deformation of the first transition section, the second transition section, and the third transition section that stores energy therein. When undergoing deformation, the first transition section, the second transition section, and the third transition section move the bridge from the natural form to the insertion form. Concurrently, the first transition section moves the first fixation member, the second transition section moves the second fixation member, and the third transition section moves the third fixation member linearly away from the central axis. The first fixation member, the second fixation member, and the third fixation member accordingly diverge relative to the central axis as the first fixation member, the second fixation member, and the third fixation member progress from the natural position to the insertion position, thereby facilitating the implant storing energy deliverable radially relative to the central vertical axis.

A transition of the implant from the insertion shape toward the natural shape includes the first transition section, the second transition section, and the third transition section delivering the energy stored therein. In delivering the stored energy, the first transition section, the second transition section, and the third transition section move the bridge from the insertion form toward the natural form. Concurrently, the first transition section moves the first fixation member, the second transition section moves the second fixation member, and the third transition section moves the third fixation member linearly toward the central axis. The first fixation member, the second fixation member, and the third fixation member accordingly converge relative to the central axis as the first fixation member, the second fixation member, and the third fixation member progress from the insertion position toward the natural position, thereby facilitating the implant delivering the energy stored therein radially relative to the central vertical axis.

The first fixation member, the second fixation member, and the third fixation member in the natural position reside from the central vertical axis at a first angle measured from a plane perpendicular to the central vertical axis, whereas the first fixation member, the second fixation member, and the third fixation member in the insertion position reside from the central vertical axis at a second angle measured from a plane perpendicular to the central vertical axis that is greater than the first angle. The first fixation member in the third embodiment includes a first screw inserted through the opening of the first bridge segment at the end thereof. Likewise, the second fixation member includes a second screw inserted through the opening of the second bridge segment at the end thereof, and the third fixation member includes a third screw inserted through the opening of the third bridge segment at the end thereof.

A transition of the implant from the natural shape to the insertion shape includes a deformation of the first transition section, the second transition section, and the third transition section that stores energy therein. When undergoing deformation, the first transition section, the second transition section, and the third transition section move the bridge from the natural form to the insertion form. Concurrently, the first transition section moves the first screw, the second transition section moves the second screw, and the third transition section moves the third screw linearly away from the central axis. The first screw, the second screw, and the third screw accordingly diverge relative to the central axis as the first screw, the second screw, and the third screw progress from the natural position to the insertion position, thereby facilitating the implant storing energy deliverable radially relative to the central vertical axis.

A transition of the implant from the insertion shape toward the natural shape includes the first transition section, the second transition section, and the third transition section delivering the energy stored therein. In delivering the stored energy, the first transition section, the second transition section, and the third transition section move the bridge from the insertion form toward the natural form. Concurrently, the first transition section moves the first screw, the second transition section moves the second screw, and the third transition section moves the third screw linearly toward the central axis. The first screw, the second screw, and the third screw accordingly converge relative to the central axis as the first screw, the second screw, and the third screw progress from the insertion position toward the natural position, thereby facilitating the implant delivering the energy stored therein radially relative to the central vertical axis.

In the third embodiment of the radially compressive implant, the bridge includes a fourth bridge segment extending from the center section to an end thereof and a fifth bridge segment extending from the center section to an end thereof. The fourth bridge segment and the fifth bridge segment each include an opening adjacent the end thereof. The first bridge segment, the second bridge segment, the third bridge segment, the fourth bridge segment, and the fifth bridge segment are spaced symmetrically about the central vertical axis of the implant. The bridge further includes a fourth transition section located in the fourth bridge segment between the center section and the opening of the fourth bridge segment and a fifth transition section located in the fifth bridge segment between the center section and the opening of the fifth bridge segment. A fourth fixation member is insertable through the opening of the fourth bridge segment at the end thereof. A fifth fixation member is insertable through the opening of the fifth bridge segment at the end thereof. The fourth bridge segment and the fifth bridge segments at the ends thereof each define an interlock adapted to facilitate engagement of the implant with an implant delivery device.

A transition of the implant from the natural shape to the insertion shape includes a deformation of the first transition section, the second transition section, the third transition section, the fourth transition section, and the fifth transition section that stores energy therein. When undergoing deformation, the first transition section, the second transition section, the third transition section, the fourth transition section, and the fifth transition section move the bridge from the natural form to the insertion form. Concurrently, the first transition section moves the first fixation member, the second transition section moves the second fixation member, the third transition section moves the fourth fixation member, the fourth transition section moves the fourth fixation member, and the fifth transition section moves the fifth fixation member linearly away from the central axis. The first fixation member, the second fixation member, the third fixation member, the fourth fixation member, and the fifth fixation member accordingly diverge relative to the central axis as the first fixation member, the second fixation member, the third fixation member, the fourth fixation member, and the fifth fixation member progress from the natural position to the insertion position, thereby facilitating the implant storing energy deliverable radially relative to the central vertical axis.

A transition of the implant from the insertion shape toward the natural shape includes the first transition section, the second transition section, the third transition section, the fourth transition section, and the fifth transition section delivering the energy stored therein. In delivering the stored energy, the first transition section, the second transition section, the third transition section, the fourth transition section, and the fifth transition section move the bridge from the insertion form toward the natural form. Concurrently, the first transition section moves the first fixation member, the second transition section moves the second fixation member, the third transition section moves the third fixation member, the fourth transition section, and the fifth transition section moves the fifth fixation member linearly toward the central axis. The first fixation member, the second fixation member, the third fixation member, the fourth fixation member, and the fifth fixation member accordingly converge relative to the central axis as the first fixation member, the second fixation member, the third fixation member, the fourth fixation member, and the fifth fixation member progress from the insertion position toward the natural position, thereby facilitating the implant delivering the energy stored therein radially relative to the central vertical axis.

In an orthopedic fixation system, an implant delivery device is configured in an implant release position to release the implant. The implant delivery device further is configured in an implant engagement position to engage the implant and constrain the implant in the insertion shape.

The implant delivery device in a first embodiment thereof includes a central vertical axis and transitions between the implant release position and the implant engagement position through a transitional position. The implant delivery device includes a barrel, a first finger, a second finger, a third finger, and a plunger. The first finger, which extends from the barrel, terminates in an abutment and includes a bend with a first end and a second end. The second finger, which extends from the barrel, terminates in an abutment and includes a bend with a first end and a second end. The third finger, which extends from the barrel, terminates in an abutment and includes a bend with a first end and a second end. The bends of the first finger, the second finger, and the third finger define an expansion. The plunger integrates with the barrel and the first finger, the second finger, and the third finger. The plunger includes a protrusion disposed in the expansion defined by the bends of the first finger, the second finger, and the third finger and a rod extending from the protrusion.

The implant delivery device of the first embodiment in the implant release position includes the plunger retracted relative to the barrel. The rod accordingly disengages from the abutments of the first finger, the second finger, and the third finger and the aperture of the implant while moving above the abutments and the implant. In addition, the protrusion moves adjacent and in abutment with the first ends of the bends in the first finger, the second finger, and the third finger such that the protrusion expands the first finger, the second finger, and third finger. Upon expansion of the first finger, the second finger, and third finger, the abutments thereof in a disengaged position are spaced apart from the central vertical axis of the implant delivery device a distance that facilitates a bypass of the implant by the abutments.

The implant delivery device of the first embodiment in the implant engagement position includes the plunger advanced into the barrel. The protrusion accordingly moves adjacent and in abutment with the second ends of the bends in the first finger, the second finger, and the third finger such that the protrusion expands the first, second, and third fingers. Upon expansion of the first finger, the second finger, and third finger, the abutments thereof in an engaged position are spaced apart from the central vertical axis of the implant delivery device a distance that facilitates the abutments engaging the implant and constraining the implant in the insertion shape. In addition, the rod inserts through the aperture of the implant in order to stabilize the implant in the implant delivery device. Moreover, the rod moves adjacent and in abutment with the abutments of the first finger, the second finger, and third finger whereby the rod facilitates the abutments engaging the implant and constraining the implant in the insertion shape.

The implant delivery device of the first embodiment in the transitional position includes the plunger either retracted or advanced partially relative to the barrel. The protrusion accordingly moves into the expansion defined by the bends of the first finger, the second finger, and the third finger such that the first finger, the second finger, and the third finger collapse. Upon collapse of the first finger, the second finger, and third finger, the abutments thereof in an intermediate position are spaced apart from the central vertical axis of the implant delivery device a distance that facilitates a disengagement of the abutments from the implant or an engagement of the abutments with the implant. In addition, the rod inserts into the aperture of the implant in order to stabilize the implant in the implant delivery device.

The implant delivery device of the first embodiment when loading with the implant in the insertion shape includes the plunger advanced partially relative to the barrel. The protrusion accordingly moves from the first ends of the bends in the first finger, the second finger, and the third finger into the expansion defined by the bends such that the first finger, the second finger, and the third finger collapse. As a result, the abutment of the first finger bypasses and resides below the first bridge segment of the bridge of the implant, the abutment of the second finger being bypasses and resides below the second bridge segment of the bridge of the implant, and the abutment of the third finger bypasses and resides below the third bridge segment of the bridge of the implant. Upon the collapse of the first finger, the second finger, and the third finger, the abutment of the first finger in an intermediate position resides in an unaligned position remote from the first fixation member of the implant but interior thereto, the abutment of the second finger in an intermediate position resides in an unaligned position remote from the second fixation member of the implant but interior thereto, and the abutment of the third finger in an intermediate position resides in an unaligned position remote from the third fixation member of the implant but interior thereto. In addition, the rod inserts into the aperture located in the center section of the bridge in order to stabilize the implant in the implant delivery device.

The implant delivery device of the first embodiment when loading with the implant in the insertion shape further includes a rotation of the implant delivery device. As a result of the rotation, the abutment of the first finger in a movement from the unaligned position to an aligned position resides separated from the first fixation member of the implant but in alignment therewith. Likewise, the abutment of the second finger in a movement from the unaligned position to an aligned position resides separated from the second fixation member of the implant but in alignment therewith, and the abutment of the third finger in a movement from the unaligned position to an aligned position resides separated from the third fixation member of the implant but in alignment therewith.

The implant delivery device of the first embodiment when loading with the implant in the insertion shape still further includes the plunger advanced fully relative to the barrel. The protrusion accordingly moves from the expansion defined by the bends in the first finger, the second finger, and the third finger to a location adjacent and in abutment with the second ends of the bends such that the first finger, the second finger, and the third finger expand. Upon expansion of the first finger, the second finger, and the third finger, the abutment of the first finger moves from the intermediate position to an engaged position such that the abutment abuts the first fixation member of the implant. Likewise, the abutment of the second finger moves from the intermediate position to an engaged position such that the abutment abuts the second fixation member of the implant, and the abutment of the third finger moves from the intermediate position to an engaged position such that the abutment abuts the third fixation member of the implant. In addition, the rod moves through the aperture disposed in the center section of the bridge and into an abutting relationship with the abutments of the first finger, the second finger, and third finger. As a result, the implant delivery device in the implant engagement position with the rod supporting the abutment of the first finger against the first fixation member, the abutment of the second finger against the second fixation member, and the abutment of the third finger against the third fixation member constrains the implant in the insertion shape.

The implant delivery device of the first embodiment when delivering the implant constrained in the insertion shape includes the plunger retracted partially relative to the barrel. The rod accordingly ceases contact with the abutments of the first finger, the second finger, and the third finger while remaining disposed in the aperture located in the center section of the bridge in order to stabilize the implant in the implant delivery device. In addition, the protrusion moves from the second ends of the bends in the first finger, the second finger, and the third finger into the expansion defined by the bends such that the first finger, the second finger, and the third finger collapse. Upon collapse of the first finger, the second finger, and the third finger, the abutment of the first finger moves from an engaged position such that the abutment abuts the first fixation member of the implant to an intermediate position whereby the abutment in an aligned position resides separated from the first fixation member of the implant but in alignment therewith. Likewise, the abutment of the second finger being moves from an engaged position such that the abutment abuts the second fixation member of the implant to an intermediate position whereby the abutment in an aligned position resides separated from the second fixation member of the implant but in alignment therewith, and the abutment of the third finger moves from an engaged position such that the abutment abuts the third fixation member of the implant to an intermediate position whereby the abutment in an aligned position resides separated from the third fixation member of the implant but in alignment therewith.

The implant delivery device of the first embodiment when delivering the implant constrained in the insertion shape further includes a rotation of the implant delivery device. As a result of the rotation, the abutment of the first finger in a movement from the aligned position to an unaligned position resides remote from the first fixation member of the implant but interior thereto. Likewise, the abutment of the second finger in a movement from the aligned position to an unaligned position resides remote from the second fixation member of the implant but interior thereto, and the abutment of the third finger in a movement from the aligned position to an unaligned position resides remote from the third fixation member of the implant but interior thereto.

The implant delivery device of the first embodiment when delivering the implant constrained in the insertion shape still further includes the plunger retracted fully relative to the barrel. The rod accordingly moves from the aperture located in the center section of the bridge in order to release the implant. In addition, the protrusion moves from the expansion defined by the bends in the first finger, the second finger, and the third finger to a location adjacent and in abutment with the first ends of the bends such that the first finger, the second finger, and the third finger expand. Upon expansion of the first finger, the second finger, and the third finger, the abutment of the first finger moves from the intermediate position to a disengaged position whereby the abutment resides remote from the first bridge segment of the bridge of the implant. Likewise, the abutment of the second finger moves from the intermediate position to a disengaged position whereby the abutment resides remote from the second bridge segment of the bridge of the implant, and the abutment of the third finger moves from the intermediate position to a disengaged position whereby the abutment resides remote from the third bridge segment of the bridge of the implant. As a result, the abutment of the first finger bypasses and resides above the first bridge segment of the bridge of the implant, the abutment of the second finger bypasses and resides above the second bridge segment of the bridge of the implant, and the abutment of the third finger bypasses and resides above the third bridge segment of the bridge of the implant such that the implant delivery device in the implant release position releases the implant for transition from the insertion shape toward the natural shape.

The implant delivery device in an alternative to the first embodiment includes a fourth finger. The fourth finger, which extends from the barrel, terminates in an abutment and includes a bend with a first end and a second end. The bends of the first finger, the second finger, the third finger, and the fourth finger define the expansion such that the plunger integrates with the barrel and the first finger, the second finger, the third finger, and the fourth finger The implant delivery device in a second embodiment thereof includes a central vertical axis, an implant holding ring, and a fastener. The implant holding ring terminates in a first end and a second end with a split therebetween. The implant holding ring includes a first projection with an aperture therethrough extending from the first end at a top thereof and a second projection with an aperture therethrough extending from the second end at a bottom thereof. The implant holding ring is configured for pivotal movement between an open position and a closed position. When the implant holding ring pivots to the open position, the first projection and the second projection and the apertures thereof are misaligned, and the implant holding ring releases the implant. Conversely, when the implant holding ring pivots to the closed position, the first projection and the second projection align such that the apertures thereof vertically align, and the implant holding ring at an inner wall thereof engages the implant and constrains the implant in the insertion shape. The fastener, when the implant holding ring pivots to the closed position, engages the first projection and the second projection at the apertures thereof thereby securing the implant holding ring in the closed position.

The implant delivery device of the second embodiment when loading with the implant in the insertion shape includes the implant holding ring being placed about the implant in the insertion shape. The implant holding ring pivots in a contraction from the open position to the closed position such that the implant holding ring at the inner wall thereof engages the implant and retains the implant therein. The first projection and the second projection, upon contraction of the implant holding ring from the open position to the closed position, align such that the apertures thereof vertically align. Moreover, the fastener inserts into the apertures of the first projection and the second projection in order to secure the implant holding ring in the closed position, whereby the implant delivery device in the implant engagement position constrains the implant in the insertion shape.

The implant delivery device of the second embodiment when delivering the implant constrained in the insertion shape includes removal of the fastener from the apertures of the first projection and the second projection in order to release the first projection and the second projection. The implant holding ring, upon removal of the fastener, pivots in an expansion from the closed position to the open position whereby the implant holding ring at the inner wall thereof disengages from the implant. The first projection and the second projection, upon expansion of the implant holding ring from the closed position to the open position, move into misalignment such that the apertures thereof misalign. The implant delivery device in the implant release position accordingly releases the implant for transition from the insertion shape toward the natural shape.

The implant delivery device of the second embodiment when loading with the implant in the insertion shape includes the implant holding ring being placed about the implant in the insertion shape. The implant holding ring pivots in a contraction from the open position to the closed position such that the implant holding ring at the inner wall thereof engages the first bridge segment of the bridge of the implant at the end thereof, the second bridge segment of the bridge of the implant at the end thereof, and the third bridge segment of the bridge of the implant at the end thereof and retains the implant therein. More particularly, the implant holding ring at the inner wall thereof engages the first bridge segment, the second bridge segment, and the third bridge segment at the interlocks thereof. The first projection and the second projection, upon contraction of the implant holding ring from the open position to the closed position, align such that the apertures thereof vertically align. Moreover, the fastener inserts into the apertures of the first projection and the second projection in order to secure the implant holding ring in the closed position, whereby the implant delivery device in the implant engagement position constrains the implant in the insertion shape.

The implant delivery device of the second embodiment when delivering the implant constrained in the insertion shape includes removal of the fastener from the apertures of the first projection and the second projection in order to release the first projection and the second projection. The implant holding ring, upon removal of the fastener, pivots in an expansion from the closed position to the open position whereby the implant holding ring at the inner wall thereof disengages from the first bridge segment of the bridge of the implant at the end thereof, the second bridge segment of the bridge of the implant at the end thereof, and the third bridge segment of the bridge of the implant at the end thereof. More particularly, the implant holding ring at the inner wall thereof disengages the first bridge segment, the second bridge segment, and the third bridge segment at the interlocks thereof. The first projection and the second projection, upon expansion of the implant holding ring from the closed position to the open position, move into misalignment such that the apertures thereof misalign. The implant delivery device in the implant release position accordingly releases the implant for transition from the insertion shape toward the natural shape.

It is therefore an object of the present invention to provide a radially compressive implant transitionable between a natural shape and an insertion shape.

It is another object of the present invention to provide the radially compressive implant, whereby, after implantation in bone, bones, or bone pieces, the implant continuously and radially compresses the bone, bones, or bone pieces to promote fusion thereof due to an attempted transition of the implant from the insertion shape to the natural shape.

It is a further object of the present invention to provide an orthopedic fixation system including a radially compressive implant and an implant delivery device configured in an implant release position to release the implant and in an implant engagement position to engage the implant and constrain the implant in the insertion shape.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF DRAWINGS

FIGS. 2A and 2B are isometric views illustrating the radially compressive shape memory implant according to the first embodiment residing in an insertion shape.

FIG. 2C is a side view illustrating the radially compressive shape memory implant according to the first embodiment residing in the insertion shape.

FIG. 2D is a top view illustrating the radially compressive shape memory implant according to the first embodiment residing in the insertion shape.

FIG. 2E is a bottom view illustrating the radially compressive shape memory implant according to the first embodiment residing in the insertion shape.

DETAILED DESCRIPTION OF THE PREFERRED EMBODIMENTS

Figure 1A:
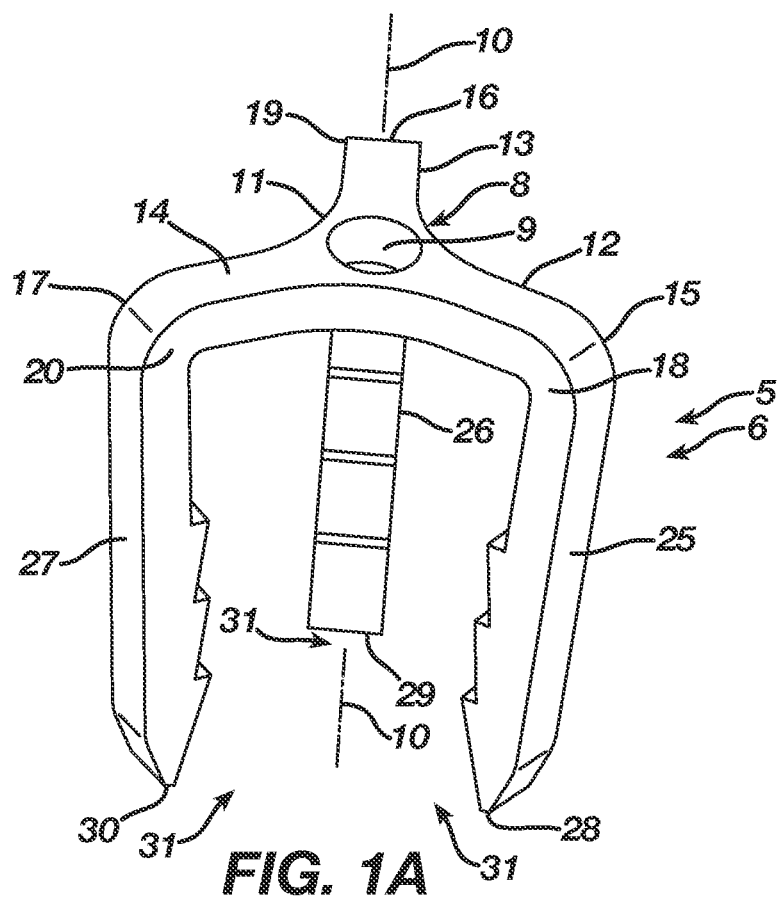
FIGS. 1A and 1B are isometric views illustrating a radially compressive shape memory implant according to a first embodiment residing in a natural shape.
Figure 1B:
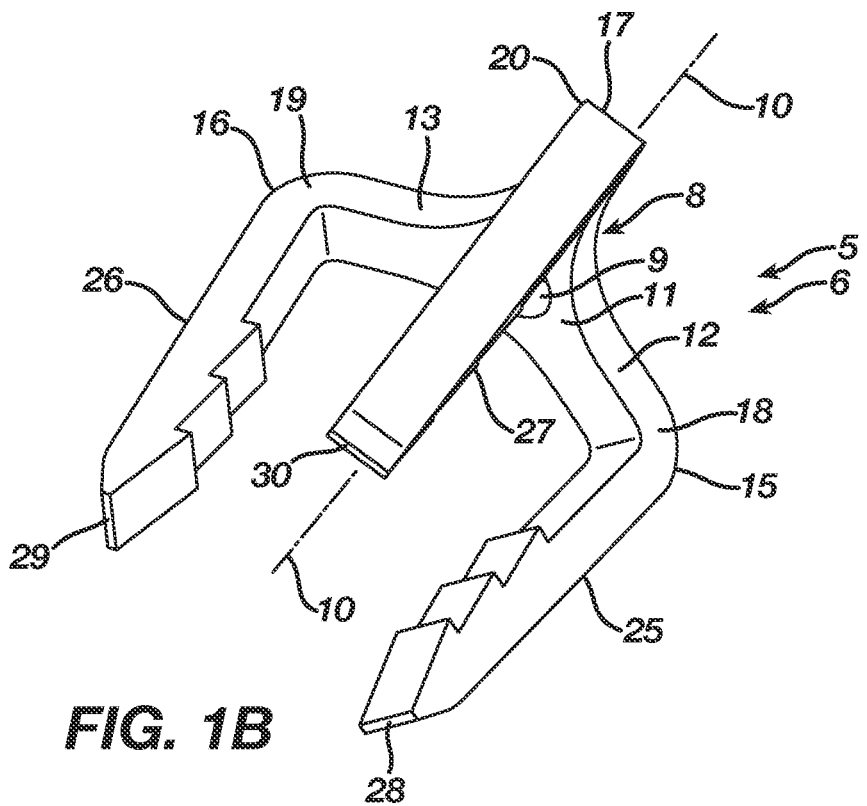
Figure 1C:
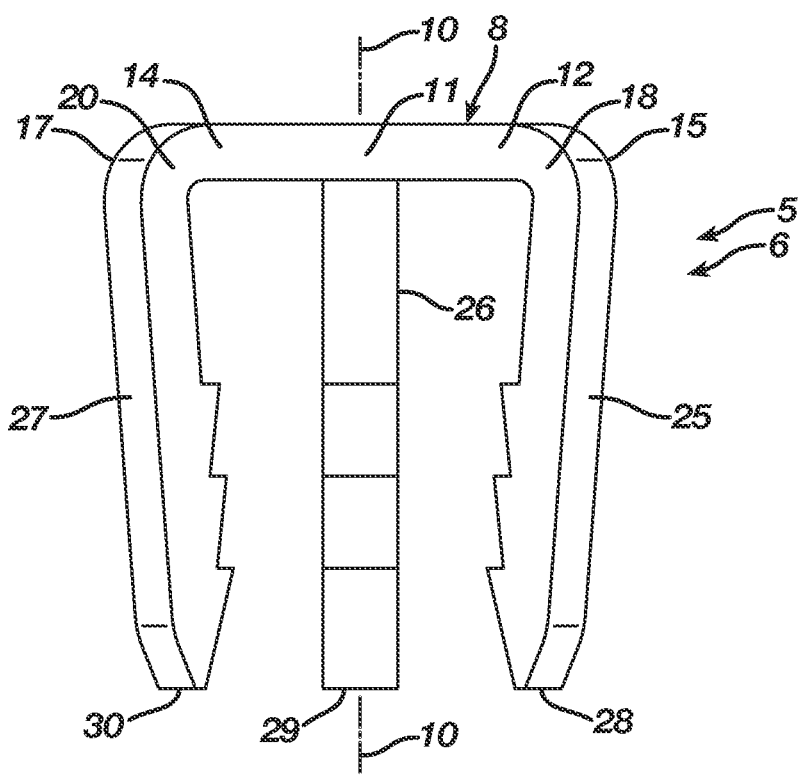
FIG. 1C is a side view illustrating the radially compressive shape memory implant according to the first embodiment residing in the natural shape.
Figure 1D:
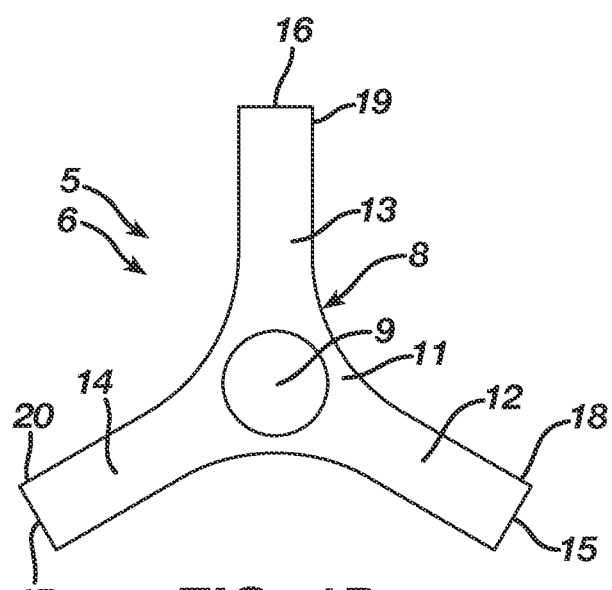
FIG. 1D is a top view illustrating the radially compressive shape memory implant according to the first embodiment residing in the natural shape.
Figure 1E:
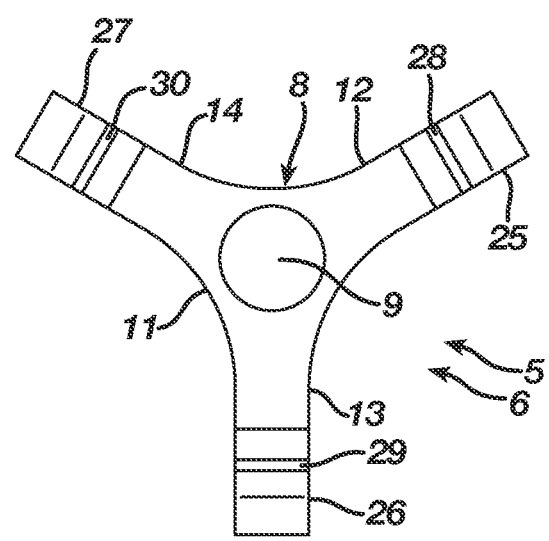
FIG. 1E is a bottom view illustrating the radially compressive shape memory implant according to the first embodiment residing in the natural shape.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 1A-1E illustrate an orthopedic implant 5 according to a first embodiment in a natural shape 6, whereas FIGS. 2A-2E illustrate the orthopedic implant 5 in an insertion shape 7. The implant 5 in the first embodiment may be manufactured from a shape memory material with superelastic or temperature dependent properties (e.g., Nitinol) such that the implant 5 transitions between its natural shape 6 and its insertion shape 7. The implant 5 when deformed from its natural shape 6 to its insertion shape 7 stores energy deliverable to bone, bones, or bone pieces. In accordance with its manufacture from shape memory material, the implant 5 begins in its natural shape 6, is transitionable to its insertion shape 7, and, once implanted in bone, bones, or bone pieces, attempts to transition from its insertion shape 7 to its natural shape 6 whereby the implant 5 delivers the energy stored therein to the bone, bones, or bone pieces in order to affix the bone, bones, or bone pieces and promote a healing thereof. In the first embodiment, attempted transition of the implant 5 from its insertion shape 7 to its natural shape 6 continuously and radially compresses the bone, bones, or bone pieces to promote fusion thereof.

The implant 5 in the first embodiment includes a bridge 8 defining an aperture 9 at a central vertical axis 10 of the implant 5. The bridge 8 includes a center section 11 defining the aperture 9 at the central vertical axis 10 and a first bridge segment 12 extending from the center section 11 to an end 15 thereof, a second bridge segment 13 extending from the center section 11 to an end 16 thereof, and a third bridge segment 14 extending from the center section 11 to an end 17 thereof. The bridge 8 of the implant 5 according to the first embodiment includes a transition section 18 located in the first bridge segment 12 at the end 15 thereof, a transition section 19 located in the second bridge segment 13 at the end 16 thereof, and a transition section 20 located in the third bridge segment 14 at the end 17 thereof. The first bridge segment 12, the second bridge segment 13, and the third bridge segment 14 in the first embodiment are symmetrical in that the first, second, and third bridge segments 12-14 radially extend from the center section 11 and are spaced about the central vertical axis 10 equidistant or at least substantially equidistant in order for the implant 5 to provide optimal radial compression. Moreover, the symmetry of the first bridge segment 12, the second bridge segment 13, and the third bridge segment 14 includes the first, second, and third bridge segments 12-14 being dimensionally identical or at least substantially, dimensionally identical; particularly with respect to length.

The implant 5 in the first embodiment includes a fixation member in the form of a leg 25 extending from the transition section 18 of the first bridge segment 12 at its end 15, a fixation member in the form of a leg 26 extending from the transition section 19 of the second bridge segment 13 at its end 16, and a fixation member in the form of a leg 27 extending from the transition section 20 of the third bridge segment 14 at its end 17. In the first embodiment, the leg 25 is formed integrally with the first bridge segment 12 at the transition section 18, the leg 26 is formed integrally with the second bridge segment 13 at the transition section 19, and the leg 27 is formed integrally with the third bridge segment 14 at the transition section 20. The fixation members in the form of the legs 25-27 in the first embodiment, due to the configuration of the bridge 8 whereby the first, second, and third bridge segments 12-14, which include the transition sections 18-20, respectively, at the ends 15-18, are spaced apart substantially equidistant about the central vertical axis 10, also are spaced about the central vertical axis 10 equidistant or at least substantially equidistant. Each leg 25-27, which has a respective tip 28-30, may include barbs thereon that improve the pull-out resistance of the implant 5. The implant 5 includes the fixation members in the form of the legs 25-27 in order to facilitate a securing of the implant 5 with bone, bones, or bone pieces whereby the bridge 8 between the legs 25-27 traverses a fixation zone central relative to the bone, bones, or bone pieces such that the implant 5, after its insertion and attempted transition from the insertion shape 7 to the natural shape 6, delivers energy to the bone, bones, or bone pieces at their centrally located fixation zone.

Referring to FIGS. 1A-1E, the regular inherent shape of the implant 5 is its natural shape 6 where the transition sections 18-20 locate the bridge 8 in a natural form that places the legs 25-27 in a natural position, which, in the first embodiment, is convergent. More particularly, each transition section 18-20 locates a respective leg 25-27 appended thereto in a position whereby each of the legs 25-27 resides from the central vertical axis 10 at a first distance 31 as illustrated in FIG. 1A. Additionally, the legs 25-27 when residing in their natural position are spaced about the central vertical axis 10 equidistant or at least substantially equidistant due to the symmetrical configuration of the bridge segments 12-14 comprising the bridge 8. Nevertheless, referring to FIGS. 2A-2E, the implant 5 is deformable under the action of superelasticity or temperature dependent shape memory to the insertion shape 7 where the transition sections 18-20 deform to store energy while also moving the bridge 8 from its natural form to an insertion form that places the legs 25-27 in an insertion position which, in the first embodiment, is substantially parallel. More particularly, each transition section 18-20 moves a respective leg 25-27 appended thereto linearly away from the central vertical axis 10 whereby each of the legs 25-27 resides from the central vertical axis 10 at a second distance 32 as illustrated in FIG. 2A that is greater than the first distance 31. Additionally, the legs 25-27 when residing in their insertion position also are spaced about the central vertical axis 10 equidistant or at least substantially equidistant due to the linear movement of the legs 25-27 relative to the central vertical axis 10 and the symmetrical configuration of the bridge segments 12-14 comprising the bridge 8.

Since the insertion shape 7 is not the regular inherent shape of the implant 5, the implant 5 typically is mechanically constrained using an implant delivery device that maintains the bridge 8 in its insertion form and the legs 25-27 in their insertion position. The bridge 8 includes the aperture 9 in order to facilitate engagement of an implant delivery device of the present invention with the implant 5. Upon deformation of the transition sections 18-20, the implant delivery device passes through the aperture 9 while also engaging the legs 25-27 adjacent the transition sections 18-20 thereby constraining the legs 25-27 and thus the deformed transition sections 18-20 such that the implant delivery device maintains the implant 5 in its insertion shape 7.

After implantation of the implant 5 in its insertion shape 7 into bone, bones, or bone pieces and a release thereof, including, if necessary, a heating of the implant 5, the implant 5 in an attempted transition to its natural shape 6 delivers the energy stored in the transition sections 18-20, resulting in the bridge 8, due to the transition sections 18-20, attempting to transition from its insertion form to its natural form. The legs 25-27, accordingly, attempt to move from their insertion position to their natural position whereby the implant 5 affixes the bone, bones, or bone pieces through an application of a radial compressive force thereto. More particularly, each transition section 18-20 attempts to move a respective leg 25-27 appended thereto linearly toward the central vertical axis 10 such that the implant 5 through this attempted convergence of the legs 25-27 imparts a radial compressive force to the bone, bones, or bone pieces.

The implant 5 in the first embodiment applies a continuously compressive radial force to the bone, bones, or bone pieces at a central fixation zone thereby facilitating a fixation thereof due to the symmetrical arrangement of the bridge segments 12-14 about the central vertical axis 10 and the transition sections 18-20 that impart, respectively, linear movement to the legs 25-27 relative to the central vertical axis 10. In accordance therewith, the legs 25-27 diverge from the central vertical axis 10 when transitioning from their natural position to their insertion position and converge toward the central vertical axis 10 when transitioning from their insertion position to their natural position such that the legs 25-27 are spaced apart substantially equidistant about the central vertical axis 10 in both their natural and insertion positions. Consequently, upon implantation of the implant 5 in its insertion shape 7 into the bone, bones, or bone pieces with the bridge 8 traversing a central fixation zone of the bone, bones, or bone pieces followed by a release of the implant 5, the transition sections 18-20, respectively, impart the energy stored therein to the legs 25-27 such that the legs 25-27 attempt linear movement resulting in an attempted convergence of the legs 25-27 toward the central vertical axis 10 whereby the implant 5, via the attempted transition from its insertion shape 7 to its natural shape 6 due to the transition sections 18-20 and the attempted convergence of the legs 25-27, applies a continuously compressive radial force to the bone, bones, or bone pieces at the central fixation zone in order to fixate the bone, bones, or bone pieces at the central fixation zone.

FIGS. 3A-3E illustrate an orthopedic implant 50 according to a second embodiment in a natural shape 51, whereas FIGS. 4A-4E illustrate the orthopedic implant 50 in an insertion shape 52. The implant 50 in the second embodiment may be manufactured from a shape memory material with superelastic or temperature dependent properties (e.g., Nitinol) such that the implant 50 transitions between its natural shape 51 and its insertion shape 52. The implant 50 when deformed from its natural shape 51 to its insertion shape 52 stores energy deliverable to bone, bones, or bone pieces. In accordance with its manufacture from shape memory material, the implant 50 begins in its natural shape 51, is transitionable to its insertion shape 52, and, once implanted in bone, bones, or bone pieces, attempts to transition from its insertion shape 52 to its natural shape 51 whereby the implant 50 delivers the energy stored therein to the bone, bones, or bone pieces in order to affix the bone, bones, or bone pieces and promote a healing thereof. In the second embodiment, attempted transition of the implant 50 from its insertion shape 52 to its natural shape 51 continuously and radially compresses the bone, bones, or bone pieces to promote fusion thereof.

The implant 50 in the second embodiment includes a bridge 53 defining an aperture 54 at a central vertical axis 55 of the implant 50. The bridge 53 includes a center section 56 defining the aperture 54 at the central vertical axis 55 and a first bridge segment 57 extending from the center section 56 to an end 61 thereof, a second bridge segment 58 extending from the center section 56 to an end 62 thereof, a third bridge segment 59 extending from the center section 56 to an end 63 thereof, and a fourth bridge segment 60 extending from the center section 56 to an end 64 thereof. The bridge 53 of the implant 50 according to the second embodiment includes a transition section 65 located in the first bridge segment 57 at the end 61 thereof, a transition section 66 located in the second bridge segment 58 at the end 62 thereof, a transition section 67 located in the third bridge segment 59 at the end 63 thereof, and a transition section 68 located in the fourth bridge segment 60 at the end 64 thereof. The first bridge segment 57, the second bridge segment 58, the third bridge segment 59, and the fourth bridge segment 60 in the second embodiment are symmetrical in that the first, second, third, and fourth bridge segments 57-60 radially extend from the center section 56 and are spaced about the central vertical axis 55 equidistant or at least substantially equidistant in order for the implant 50 to provide optimal radial compression. Moreover, the symmetry of the first bridge segment 57, the second bridge segment 58, the third bridge segment 59, and the fourth bridge segment 60 includes the first, second, third, and fourth bridge segments 57-60 being dimensionally identical or at least substantially, dimensionally identical; particularly with respect to length.

The implant 50 in the second embodiment includes a fixation member in the form of a leg 69 extending from the transition section 65 of the first bridge segment 57 at its end 61, a fixation member in the form of a leg 70 extending from the transition section 66 of the second bridge segment 58 at its end 62, a fixation member in the form of a leg 71 extending from the transition section 67 of the third bridge segment 59 at its end 63, and a fixation member in the form of a leg 72 extending from the transition section 68 of the fourth bridge segment 60 at its end 64. In the second embodiment, the leg 69 is formed integrally with the first bridge segment 57 at the transition section 65, the leg 70 is formed integrally with the second bridge segment 58 at the transition section 66, the leg 71 is formed integrally with the third bridge segment 59 at the transition section 67, and the leg 72 is formed integrally with the fourth bridge segment 60 at the transition section 68. The fixation members in the form of the legs 69-72 in the second embodiment, due to the configuration of the bridge 53 whereby the bridge segments 57-60, which include the transition sections 65-68, respectively, at the ends 61-64, are spaced apart substantially equidistant about the central vertical axis 55, also are spaced about the central vertical axis 55 equidistant or at least substantially equidistant. Each leg 69-72, which has a respective tip 73-76, may include barbs thereon that improve the pull-out resistance of the implant 50. The implant 50 includes the fixation members in the form of the legs 69-72 in order to facilitate a securing of the implant 50 with bone, bones, or bone pieces whereby the bridge 53 between the legs 69-72 traverses a fixation zone central relative to the bone, bones, or bone pieces such that the implant 50, after its insertion and attempted transition from the insertion shape 52 to the natural shape 51, delivers energy to the bone, bones, or bone pieces at their centrally located fixation zone.

Figure 3A:
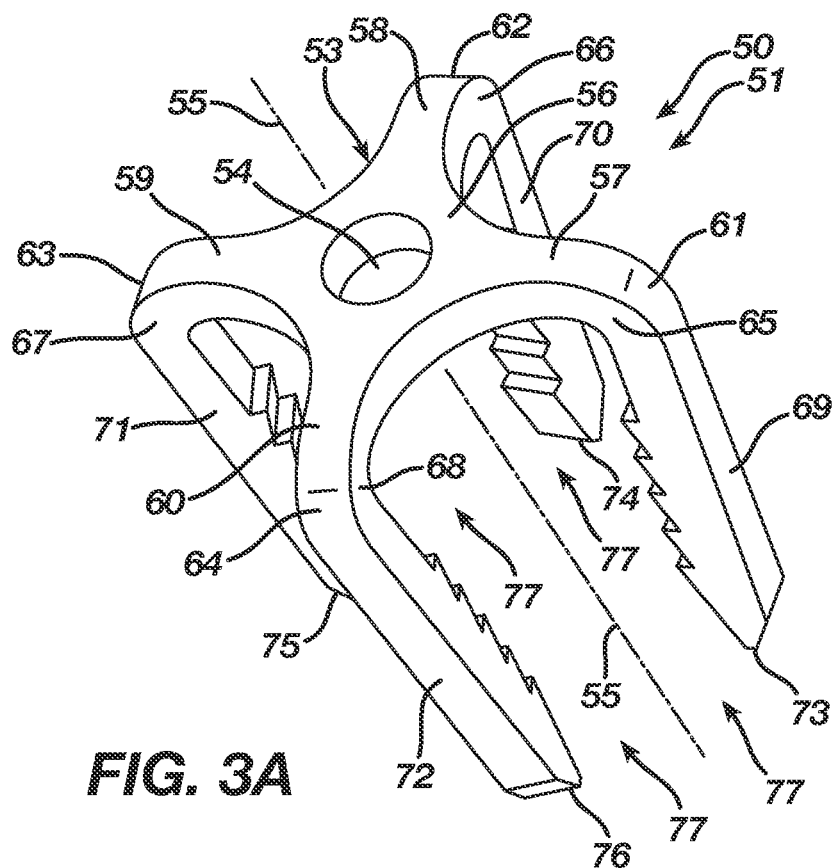
FIGS. 3A and 3B are isometric views illustrating a radially compressive shape memory implant according to a second embodiment residing in a natural shape.
Figure 3B:
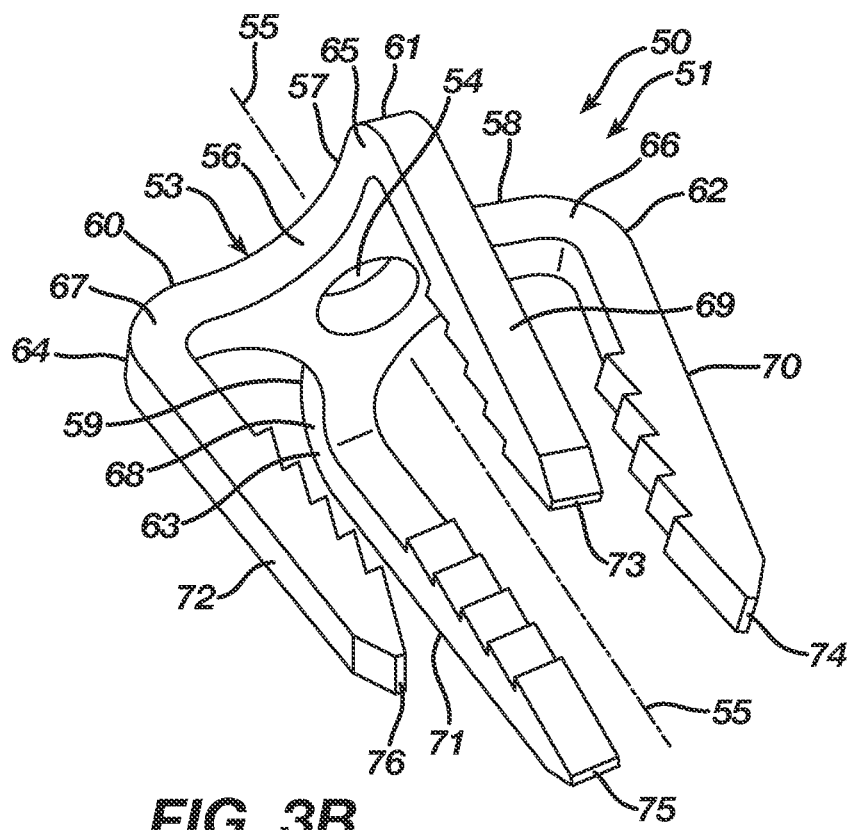
Figure 3C:
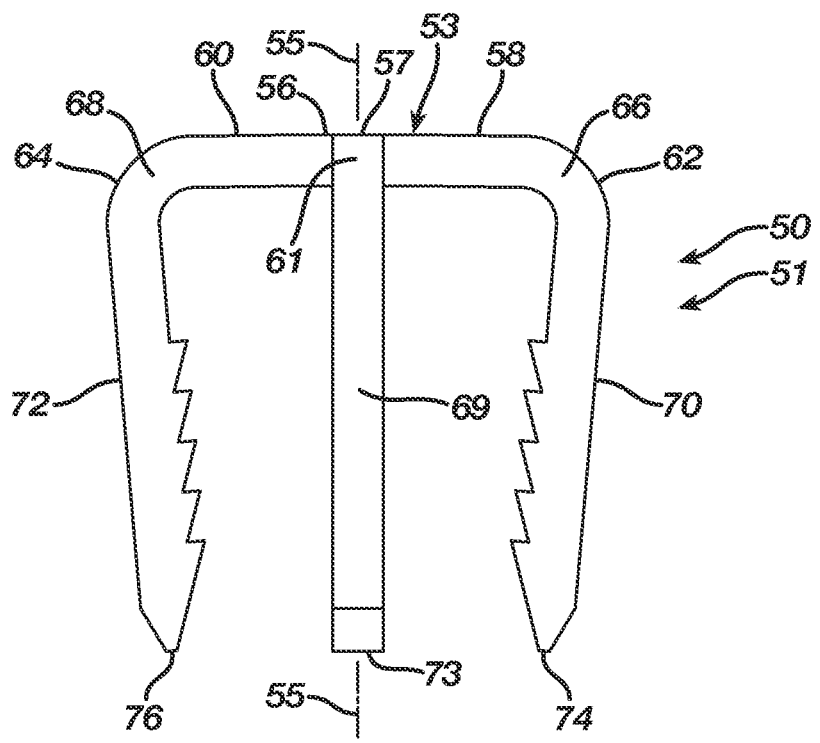
FIG. 3C is a side view illustrating the radially compressive shape memory implant according to the second embodiment residing in the natural shape.
Figure 3D:
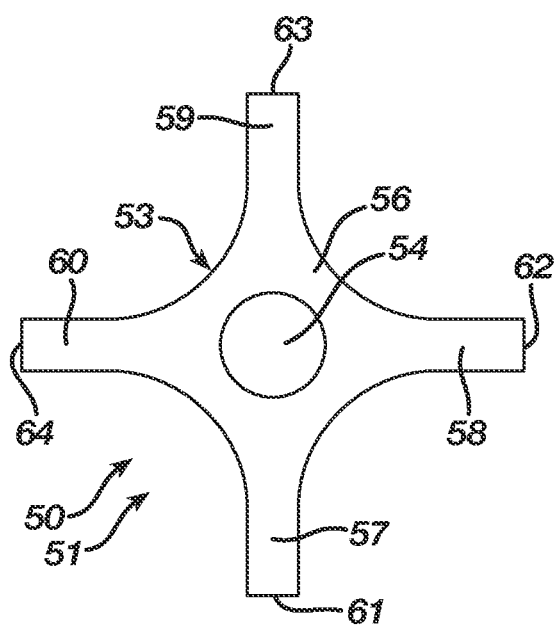
FIG. 3D is a top view illustrating the radially compressive shape memory implant according to the second embodiment residing in the natural shape.
Figure 3E:
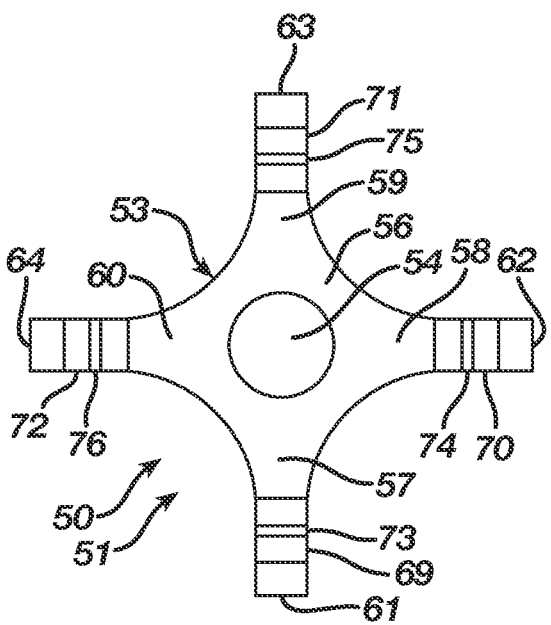
FIG. 3E is a bottom view illustrating the radially compressive shape memory implant according to the second embodiment residing in the natural shape.
Figure 4A:
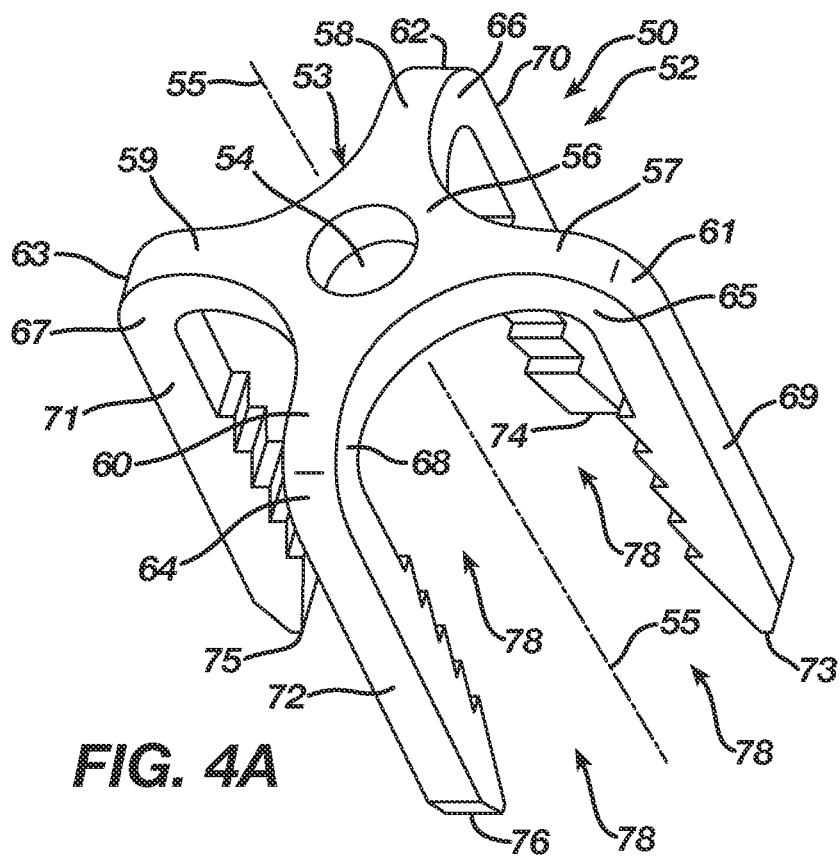
FIGS. 4A and 4B are isometric views illustrating the radially compressive shape memory implant according to the second embodiment residing in an insertion shape.
Figure 4B:
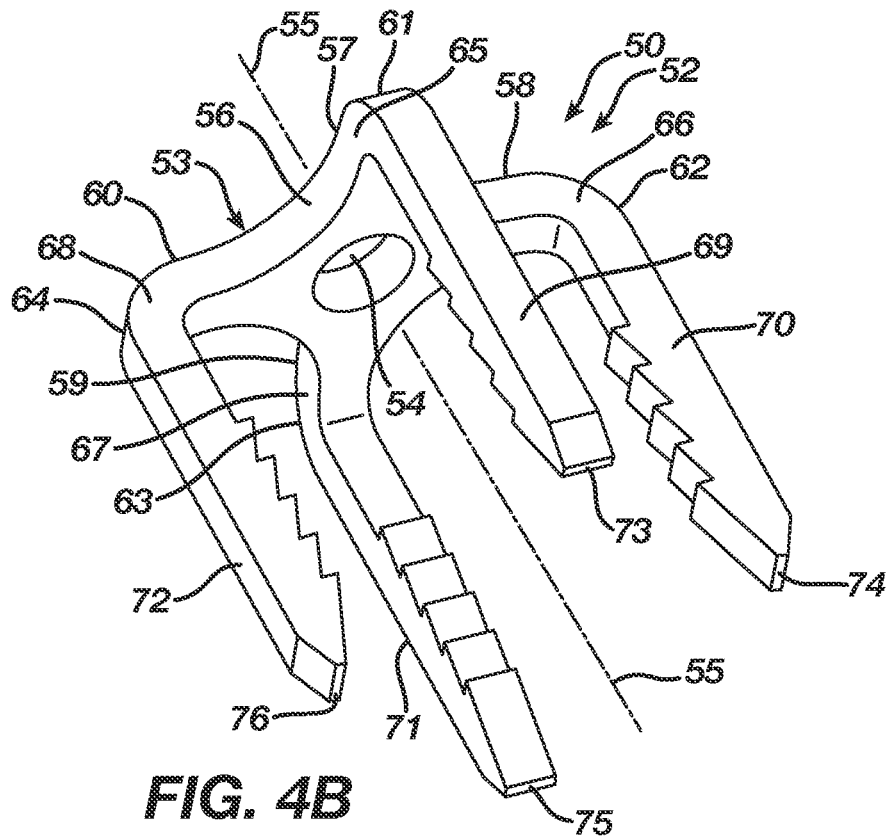
Figure 4C:
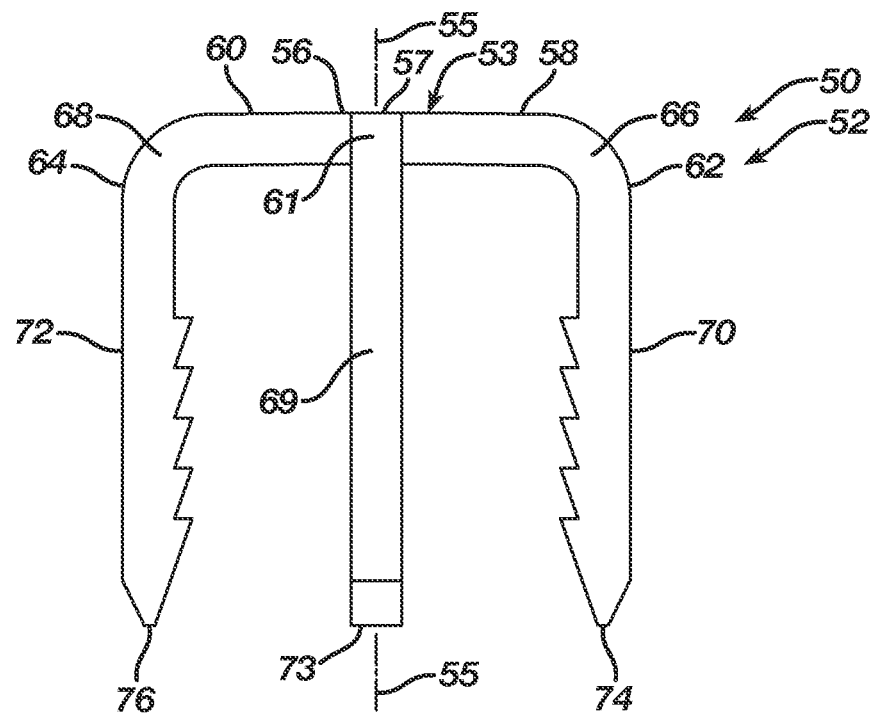
FIG. 4C is a side view illustrating the radially compressive shape memory implant according to the second embodiment residing in the insertion shape.
Figure 4D:
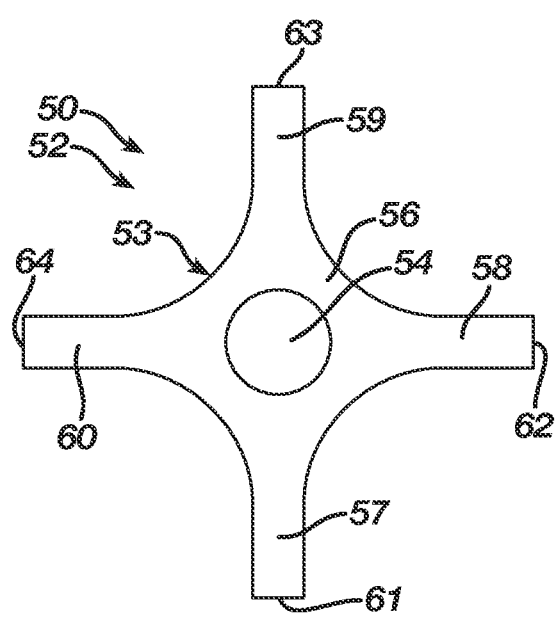
FIG. 4D is a top view illustrating the radially compressive shape memory implant according to the second embodiment residing in the insertion shape.
Figure 4E:
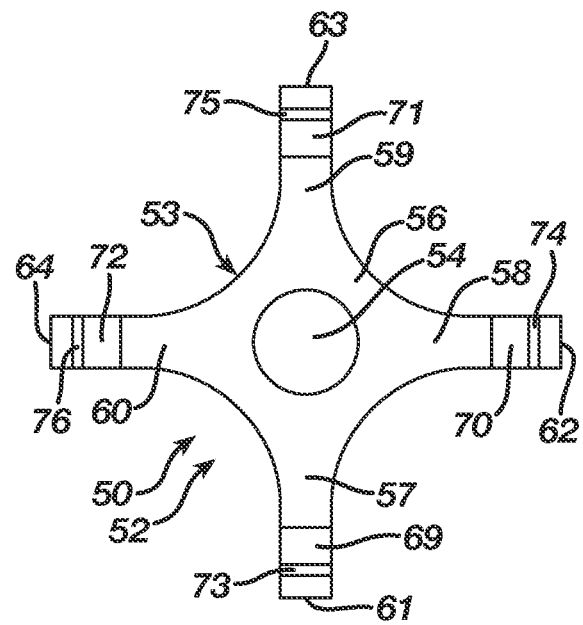
FIG. 4E is a bottom view illustrating the radially compressive shape memory implant according to the second embodiment residing in the insertion shape.

Referring to FIGS. 3A-3E, the regular inherent shape of the implant 50 is its natural shape 51 where the transition sections 65-68 locate the bridge 53 in a natural form that places the legs 69-72 in a natural position, which, in the second embodiment, is convergent. More particularly, each transition section 65-68 locates a respective leg 69-72 appended thereto in a position whereby each of the legs 69-72 resides from the central vertical axis 55 at a first distance 77 as illustrated in FIG. 3A. Additionally, the legs 69-72 when residing in their natural position are spaced about the central vertical axis 55 equidistant or at least substantially equidistant due to the symmetrical configuration of the bridge segments 57-60 comprising the bridge 53. Nevertheless, referring to FIGS. 4A-4E, the implant 50 is deformable under the action of superelasticity or temperature dependent shape memory to the insertion shape 52 where the transition sections 65-68 deform to store energy while also moving the bridge 53 from its natural form to an insertion form that places the legs 69-72 in an insertion position which, in the second embodiment, is substantially parallel. More particularly, each transition section 65-68 moves a respective leg 69-72 appended thereto linearly away from the central vertical axis 55 whereby each of the legs 69-72 resides from the central vertical axis 55 at a second distance 78 as illustrated in FIG. 4A that is greater than the first distance 77. Additionally, the legs 69-72 when residing in their insertion position also are spaced about the central vertical axis 55 equidistant or at least substantially equidistant due to the linear movement of the legs 69-72 relative to the central vertical axis 55 and the symmetrical configuration of the bridge segments 57-60 comprising the bridge 53.

Since the insertion shape 52 is not the regular inherent shape of the implant 50, the implant 50 typically is mechanically constrained using an implant delivery device that maintains the bridge 53 in its insertion form and the legs 69-72 in their insertion position. The bridge 53 includes the aperture 54 in order to facilitate engagement of an implant delivery device of the present invention with the implant 50. Upon deformation of the transition sections 65-68, the implant delivery device passes through the aperture 54 while also engaging the legs 69-72 adjacent the transition sections 65-68 thereby constraining the legs 69-72 and thus the deformed transition sections 65-68 such that the implant delivery device maintains the implant 50 in its insertion shape 52.

After implantation of the implant 50 in its insertion shape 52 into bone, bones, or bone pieces and a release thereof, including, if necessary, a heating of the implant 50, the implant 50 in an attempted transition to its natural shape 51 delivers the energy stored in the transition sections 65-68, resulting in the bridge 53, due to the transition sections 65-68, attempting to transition from its insertion form to its natural form. The legs 69-72, accordingly, attempt to move from their insertion position to their natural position whereby the implant 50 affixes the bone, bones, or bone pieces through an application of a radial compressive force thereto. More particularly, each transition section 65-68 attempts to move a respective leg 69-72 appended thereto linearly toward the central vertical axis 55 such that the implant 50 through this attempted convergence of the legs 69-72 imparts a radial compressive force to the bone, bones, or bone pieces.

The implant 50 in the second embodiment applies a continuously compressive radial force to the bone, bones, or bone pieces at a central fixation zone thereby facilitating a fixation thereof due to the symmetrical arrangement of the bridge segments 57-60 about the central vertical axis 55 and the transition sections 65-68 that impart, respectively, linear movement to the legs 69-72 relative to the central vertical axis 55. In accordance therewith, the legs 69-72 diverge from the central vertical axis 55 when transitioning from their natural position to their insertion position and converge toward the central vertical axis 55 when transitioning from their insertion position to their natural position such that the legs 69-72 are spaced apart substantially equidistant about the central vertical axis 55 in both their natural and insertion positions. Consequently, upon implantation of the implant 50 in its insertion shape 52 into the bone, bones, or bone pieces with the bridge 53 traversing a central fixation zone of the bone, bones, or bone pieces followed by a release of the implant 50, the transition sections 65-68, respectively, impart the energy stored therein to the legs 69-72 such that the legs 69-72 attempt linear movement resulting in an attempted convergence of the legs 69-72 toward the central vertical axis 55 whereby the implant 50, via the attempted transition from its insertion shape 52 to its natural shape 51 due to the transition sections 65-68 and the attempted convergence of the legs 69-72, applies a continuously compressive radial force to the bone, bones, or bone pieces at the central fixation zone in order to fixate the bone, bones, or bone pieces at the central fixation zone. Although the implant 5 according to the first embodiment discloses three legs 25-27 and the implant 50 according to the second embodiment discloses four legs 69-72, one of ordinary skill in the art will recognize an implant including more than four legs will function to continuously and radially compresses bone, bones, or bone pieces to promote a fusion thereof.

FIGS. 5A-5F illustrate an orthopedic implant 80 according to a third embodiment in a natural shape 81, whereas FIGS. 6A-6F illustrate the orthopedic implant 80 in an insertion shape 82. The implant 80 in the third embodiment may be manufactured from a shape memory material with superelastic or temperature dependent properties (e.g., Nitinol) such that the implant 80 transitions between its natural shape 81 and its insertion shape 82. The implant 80 when deformed from its natural shape 81 to its insertion shape 82 stores energy deliverable to bone, bones, or bone pieces. In accordance with its manufacture from shape memory material, the implant 80 begins in its natural shape 81, is transitionable to its insertion shape 82, and, once implanted in bone, bones, or bone pieces, attempts to transition from its insertion shape 82 to its natural shape 81 whereby the implant 80 delivers the energy stored therein to the bone, bones, or bone pieces in order to affix the bone, bones, or bone pieces and promote a healing thereof. In the third embodiment, attempted transition of the implant 80 from its insertion shape 81 to its natural shape 82 continuously and radially compresses the bone, bones, or bone pieces to promote fusion thereof.

The implant 80 in the third embodiment includes a bridge 83 defining an aperture 84 at a central vertical axis 85 of the implant 80. The bridge 83 includes a center section 86 defining the aperture 84 at the central vertical axis 85 and a first bridge segment 87 extending from the center section 86 to an end 92 thereof, a second bridge segment 88 extending from the center section 86 to an end 93 thereof, a third bridge segment 89 extending from the center section 86 to an end 94 thereof, a fourth bridge segment 90 extending from the center section 86 to an end 95 thereof, and a fifth bridge segment 91 extending from the center section 86 to an end 96 thereof. The bridge 83 of the implant 80 according to the third embodiment includes an opening 97 disposed in the first bridge segment 87 adjacent the end 92 thereof, an opening 98 disposed in the second bridge segment 88 adjacent the end 93 thereof, an opening 99 disposed in the third bridge segment 89 adjacent the end 94 thereof, an opening 100 disposed in the fourth bridge segment 90 adjacent the end 95 thereof, and an opening 101 disposed in the fifth bridge segment 91 adjacent the end 96 thereof. The openings 97-101 in the third embodiment each include an interlock feature in the form of threads that facilitate an engagement of the openings 97-101 with a fixation member. The bridge 83 of the implant 80 according to the third embodiment includes a transition section 102 located in the first bridge segment 87 between the center section 86 and the opening 97, a transition section 103 located in the second bridge segment 88 between the center section 86 and the opening 98, a transition section 104 located in the third bridge segment 89 between the center section 86 and the opening 99, a transition section 105 in the fourth bridge segment 90 between the center section 86 and the opening 100, and a transition section 106 in the fifth bridge segment 91 between the center section 86 and the opening 101. Each of the first, second, third, fourth, and fifth bridge segments 87-91 at their respective ends 92-96 includes an interlock 107 that facilitates engagement of the implant 80 with an implant delivery device. The interlocks 107 in the third embodiment each include an engagement interface 108, which is a flat surface in the respective ends 92-96 of the bridge segments 87-91, and a detent 109 disposed beneath the engagement interface 108. The first bridge segment 87, the second bridge segment 88, the third bridge segment 89, the fourth bridge segment 90, and the fifth bridge segment 91 in the third embodiment are symmetrical in that the first, second, third, fourth, and fifth bridge segments 87-91 radially extend from the center section 86 and are spaced about the central vertical axis 85 equidistant or at least substantially equidistant in order for the implant 80 to provide optimal radial compression. Moreover, the symmetry of the first bridge segment 87, the second bridge segment 88, the third bridge segment 89, the fourth bridge segment 90, and the fifth bridge segment 91 includes the first, second, third, fourth, and fifth bridge segments 87-91 being dimensionally identical or at least substantially, dimensionally identical; particularly with respect to length.

The implant 80 in the third embodiment includes a fixation member in the form of a screw 110 configured to insert through the opening 97 disposed in the first bridge segment 87 adjacent the end 92 thereof while also engaging the interlock feature of the opening 97, a fixation member in the form of a screw 111 configured to insert through the opening 98 disposed in the second bridge segment 88 adjacent the end 93 thereof while also engaging the interlock feature of the opening 98, a fixation member in the form of a screw 112 configured to insert through the opening 99 disposed in the third bridge segment 89 adjacent the end 94 thereof while also engaging the interlock feature of the opening 99, a fixation member in the form of a screw 113 configured to insert through the opening 100 disposed in the fourth bridge segment 90 adjacent the end 95 thereof while also engaging the interlock feature of the opening 100, and a fixation member in the form of a screw 114 configured to insert through the opening 101 disposed in the fifth bridge segment 91 adjacent the end 96 thereof while also engaging the interlock feature of the opening 101. The screws 110-114 in the third embodiment comprising the fixation members may include any suitable screw such as a non-locking or locking bone screw including a self-tapping bone screw. The fixation members in the form of the screws 110-114 in the third embodiment, due to the configuration of the bridge 83 whereby the bridge segments 87-91, which include the transition sections 102-106, respectively, between the center section 86 and the ends 92-96, are spaced apart substantially equidistant about the central vertical axis 85, also are spaced about the central vertical axis 85 equidistant or at least substantially equidistant. The implant 80 includes the fixation members in the form of the screws 110-114 in order to facilitate a securing of the implant 80 with bone, bones, or bone pieces whereby the bridge 83 between the screws 110-114 traverses a fixation zone central relative to the bone, bones, or bone pieces such that the implant 80, after its insertion and attempted transition from the insertion shape 82 to the natural shape 81, delivers energy to the bone, bones, or bone pieces at their centrally located fixation zone. Although the third embodiment of the implant 80 discloses the bridge 83 as including the first, second, third, fourth, and fifth bridge segments 87-91 with respective openings 97-101 disposed therein that receive a respective screw 110-114 therethrough, one of ordinary skill in the art will recognize the bridge 83 of the implant 80 will function to continuously and radially compresses bone, bones, or bone pieces to promote a fusion thereof utilizing only a first bridge segment, a second bridge segment, and a third bridge segment that are symmetrical whereby the first, second, and third bridge segments radially extend from the center section 86 and are spaced about the central vertical axis 85 equidistant or at least substantially equidistant. Moreover, one of ordinary skill in the art will recognize the bridge 83 of the implant 80 will function to continuously and radially compresses bone, bones, or bone pieces to promote a fusion thereof utilizing more than five bridge segments.

Figure 5A:
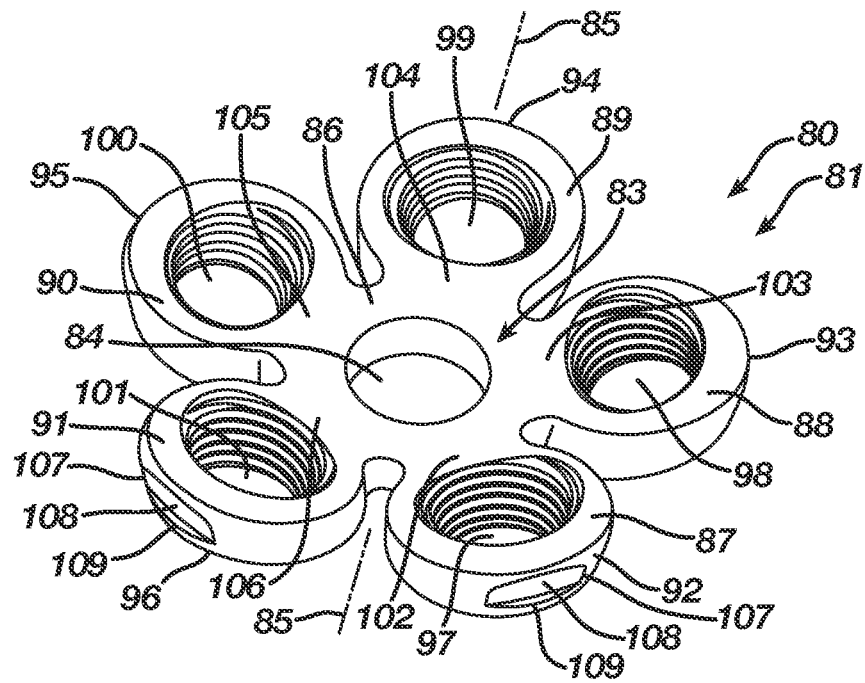
FIGS. 5A and 5C are isometric views illustrating a radially compressive shape memory implant according to a third embodiment residing in a natural shape.
Figure 5B:
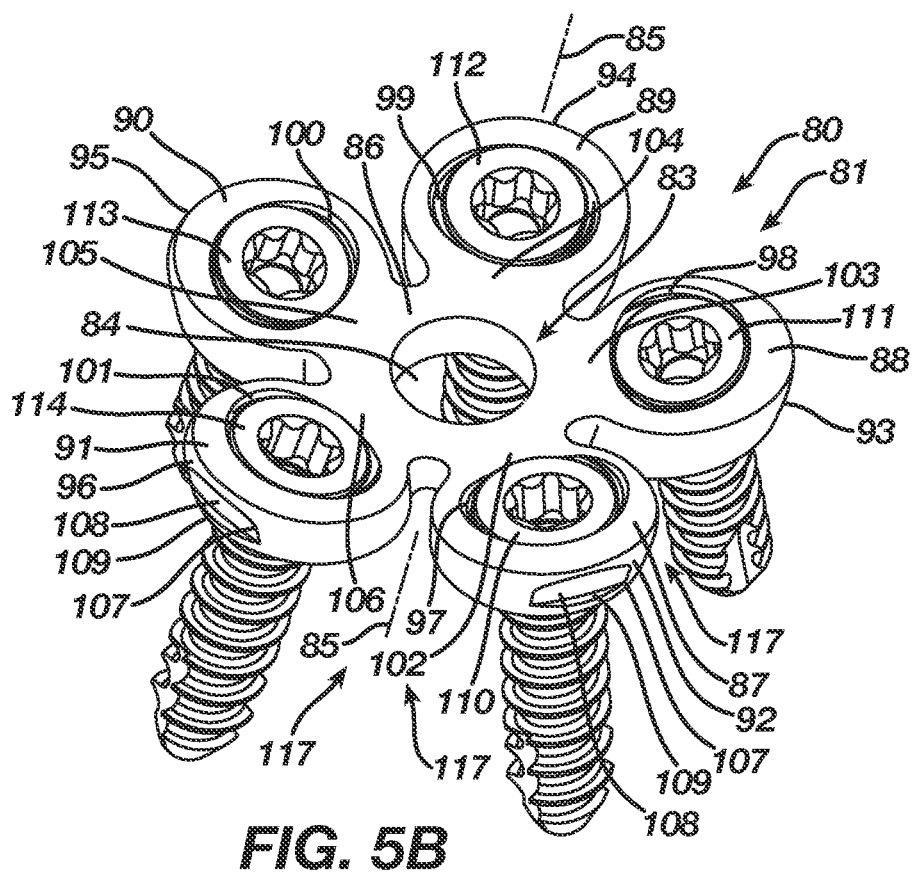
FIG. 5B is an isometric view illustrating the radially compressive shape memory implant according to the third embodiment residing in the natural shape and fasteners therefor.
Figure 5C:
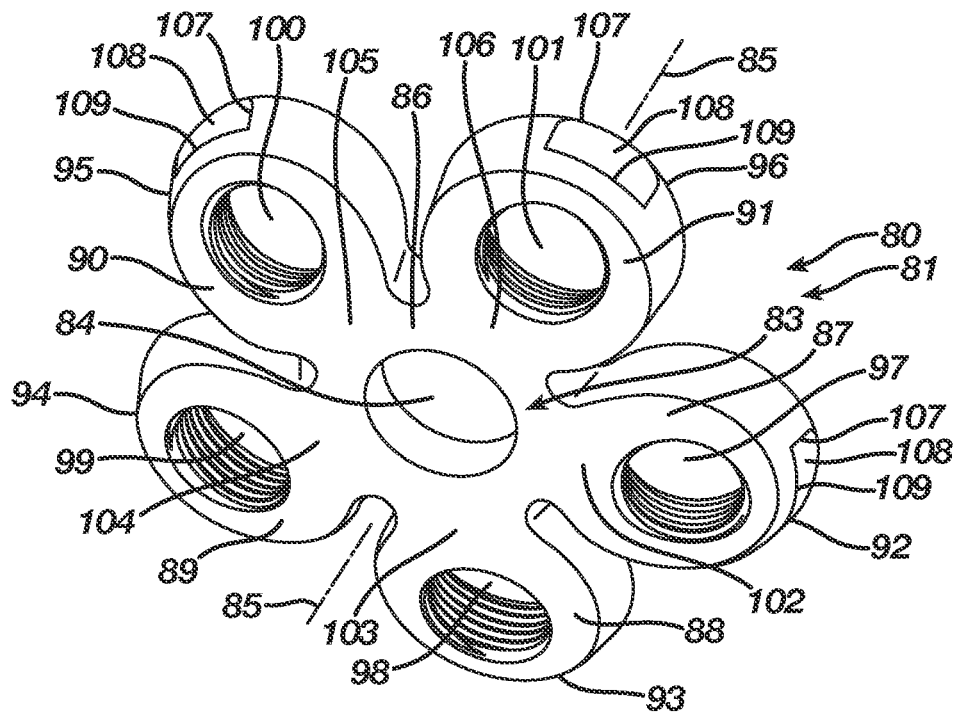
Figure 5D:
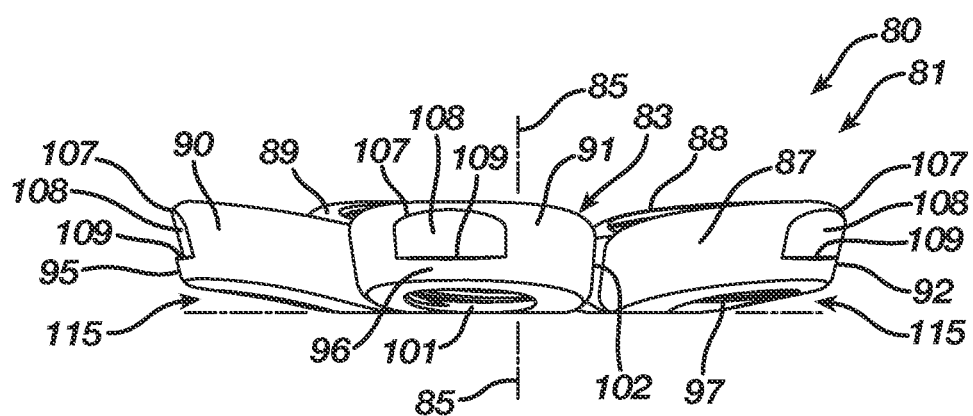
FIG. 5D is a side view illustrating the radially compressive shape memory implant according to the third embodiment residing in the natural shape.
Figure 5E:
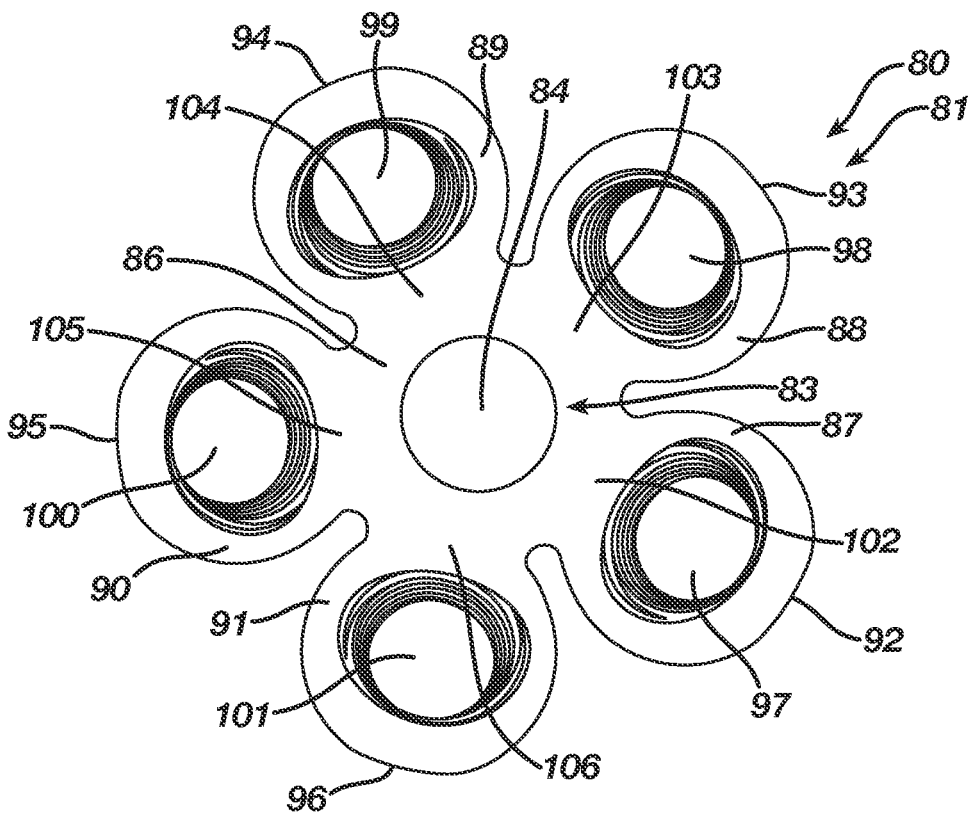
FIG. 5E is a top view illustrating the radially compressive shape memory implant according to the third embodiment residing in the natural shape.
Figure 5F:
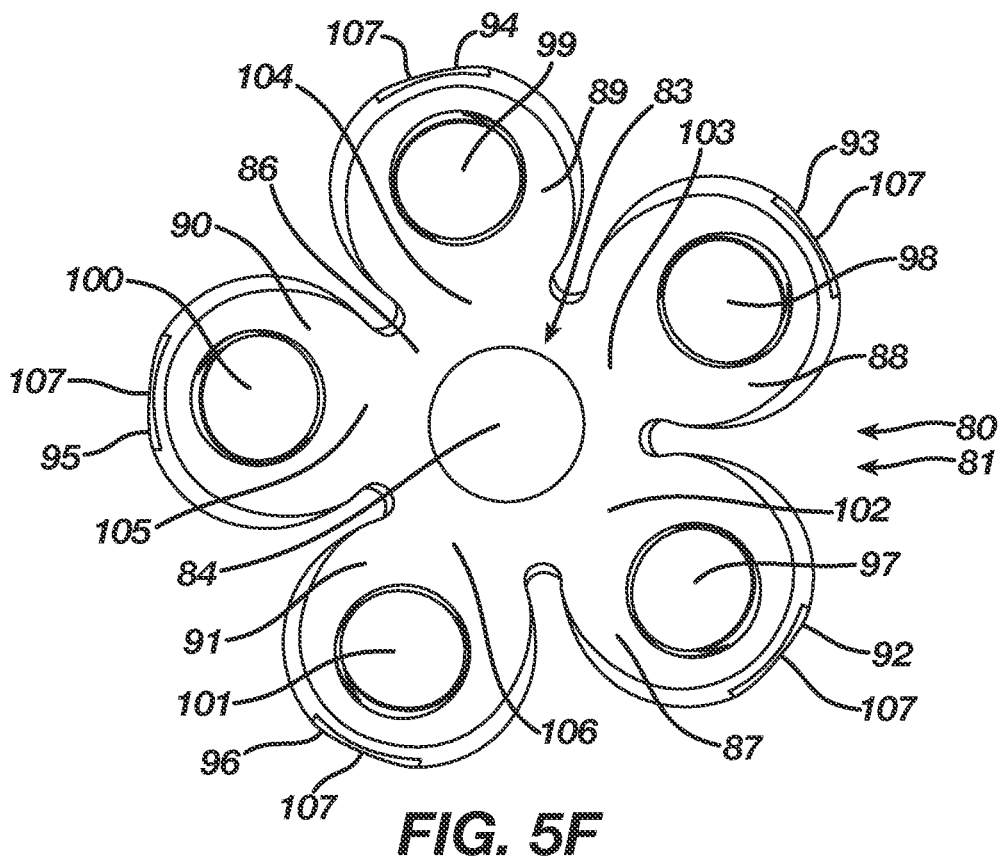
FIG. 5F is a bottom view illustrating the radially compressive shape memory implant according to the third embodiment residing in the natural shape.
Figure 6A:
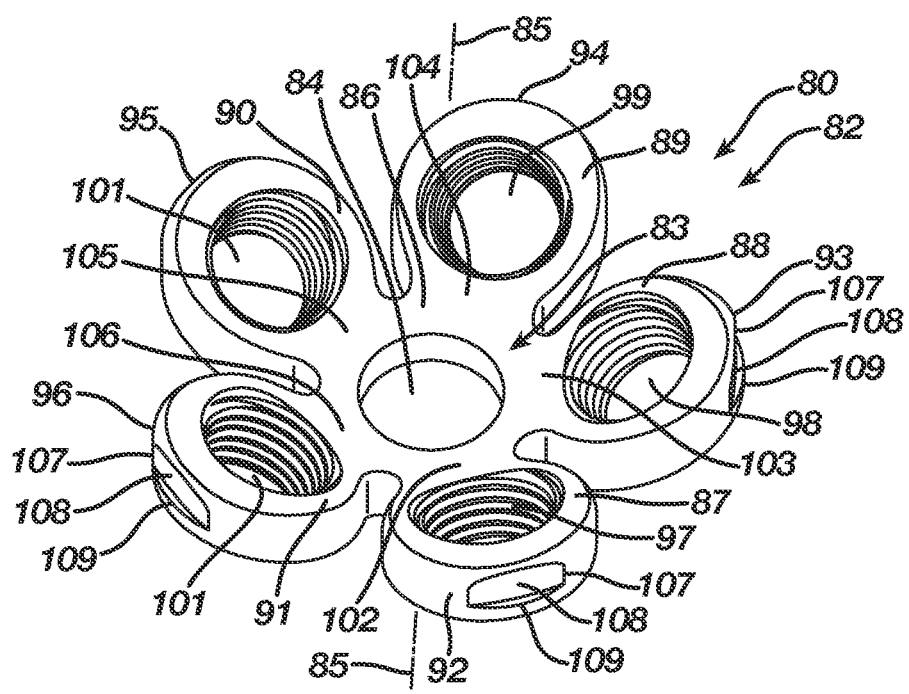
FIGS. 6A and 6C are isometric views illustrating a radially compressive shape memory implant according to the third embodiment residing in an insertion shape.
Figure 6B:
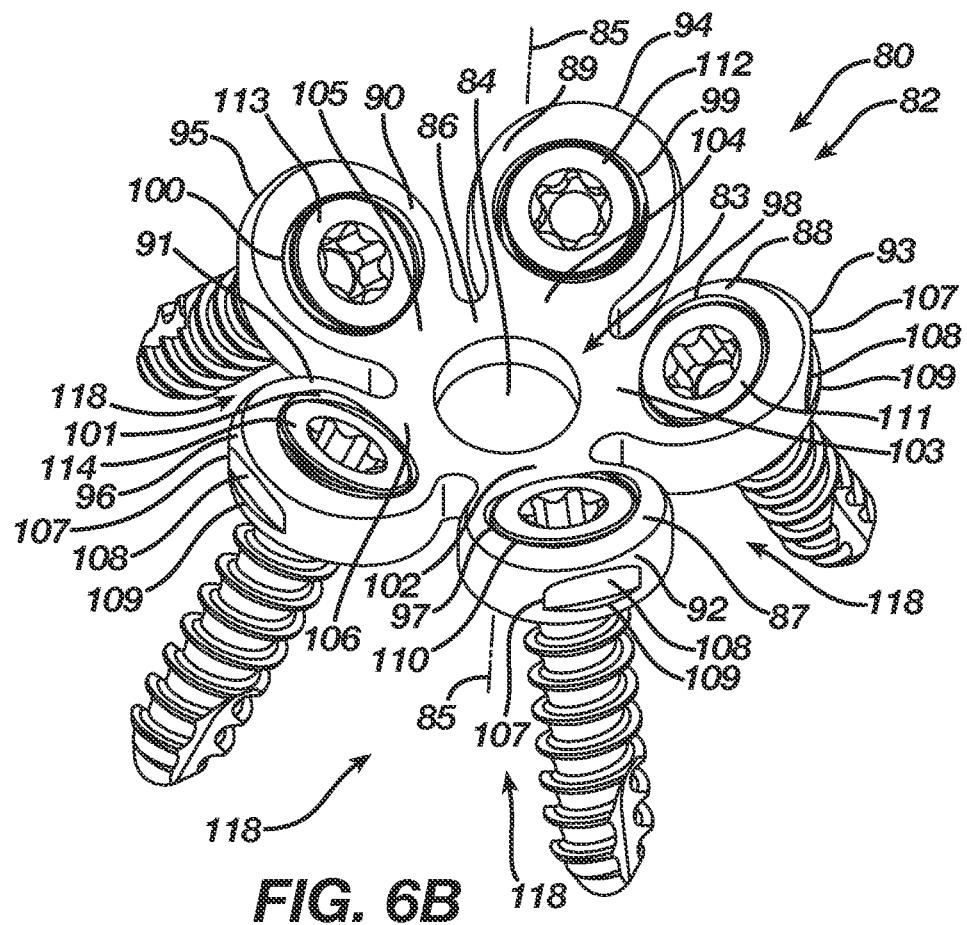
FIG. 6B is an isometric view illustrating the radially compressive shape memory implant according to the third embodiment residing in the insertion shape and fasteners therefor.
Figure 6C:
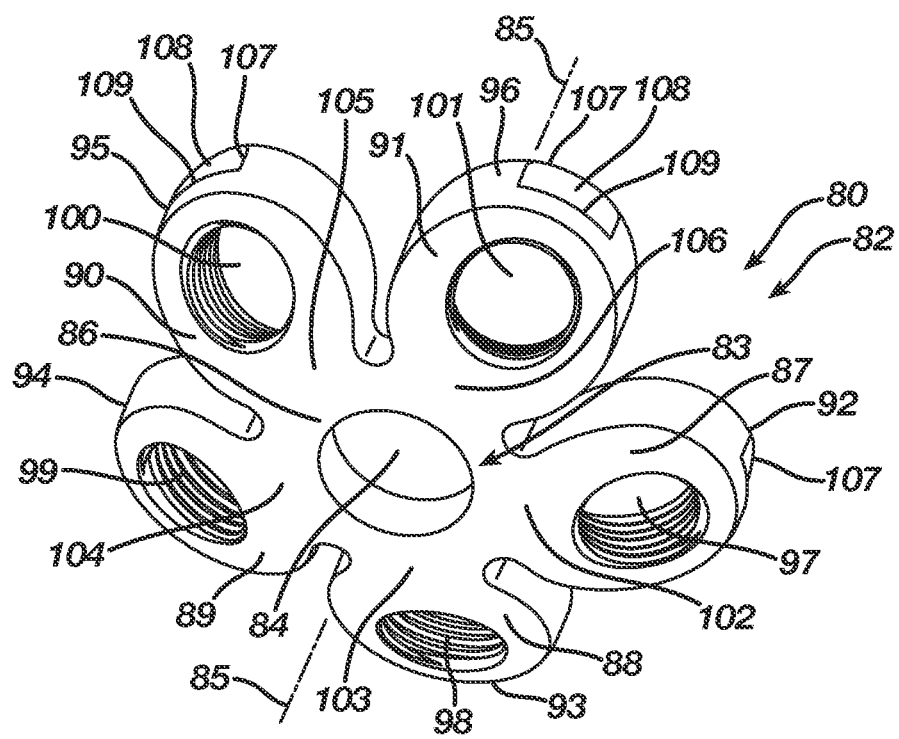
Figure 6D:
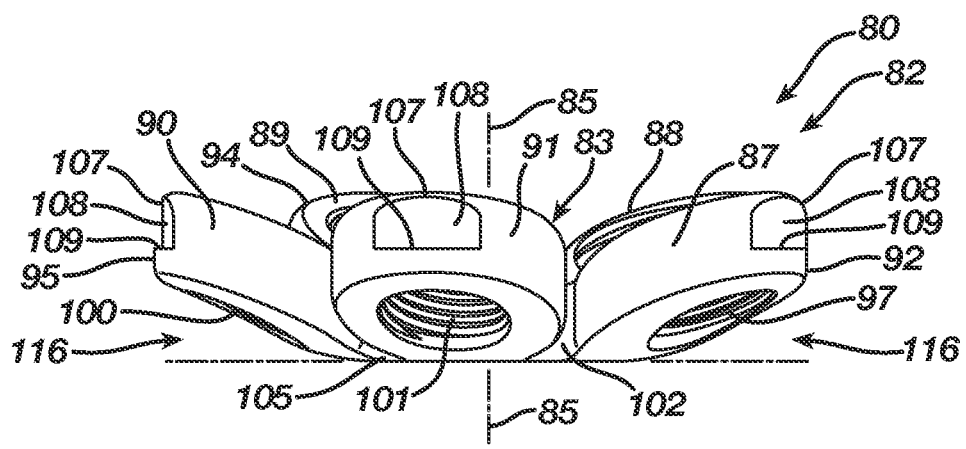
FIG. 6D is a side view illustrating the radially compressive shape memory implant according to the third embodiment residing in the insertion shape.
Figure 6E:
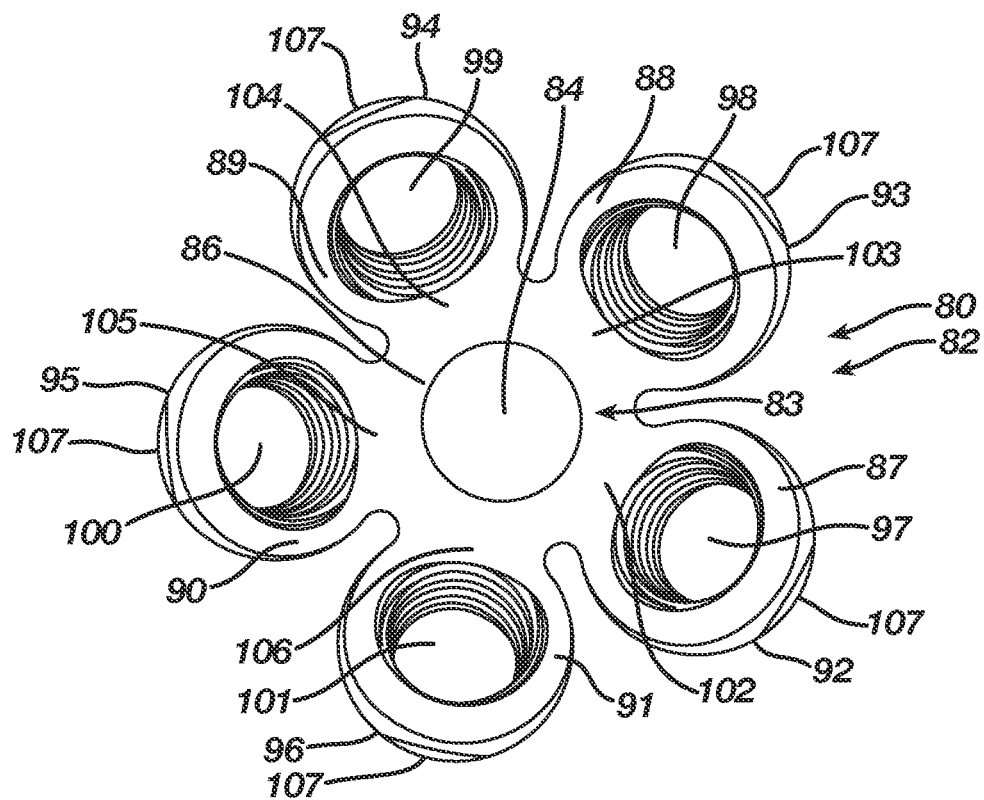
FIG. 6E is a top view illustrating the radially compressive shape memory implant according to the third embodiment residing in the insertion shape.
Figure 6F:
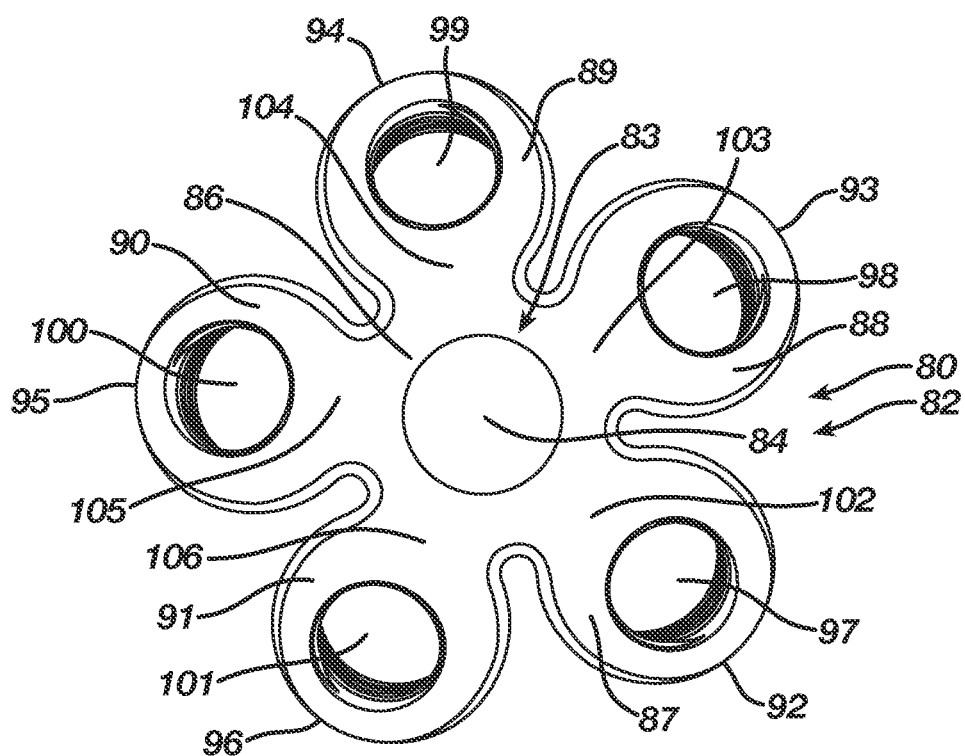
FIG. 6F is a bottom view illustrating the radially compressive shape memory implant according to the third embodiment residing in the insertion shape.
Figure 7A:
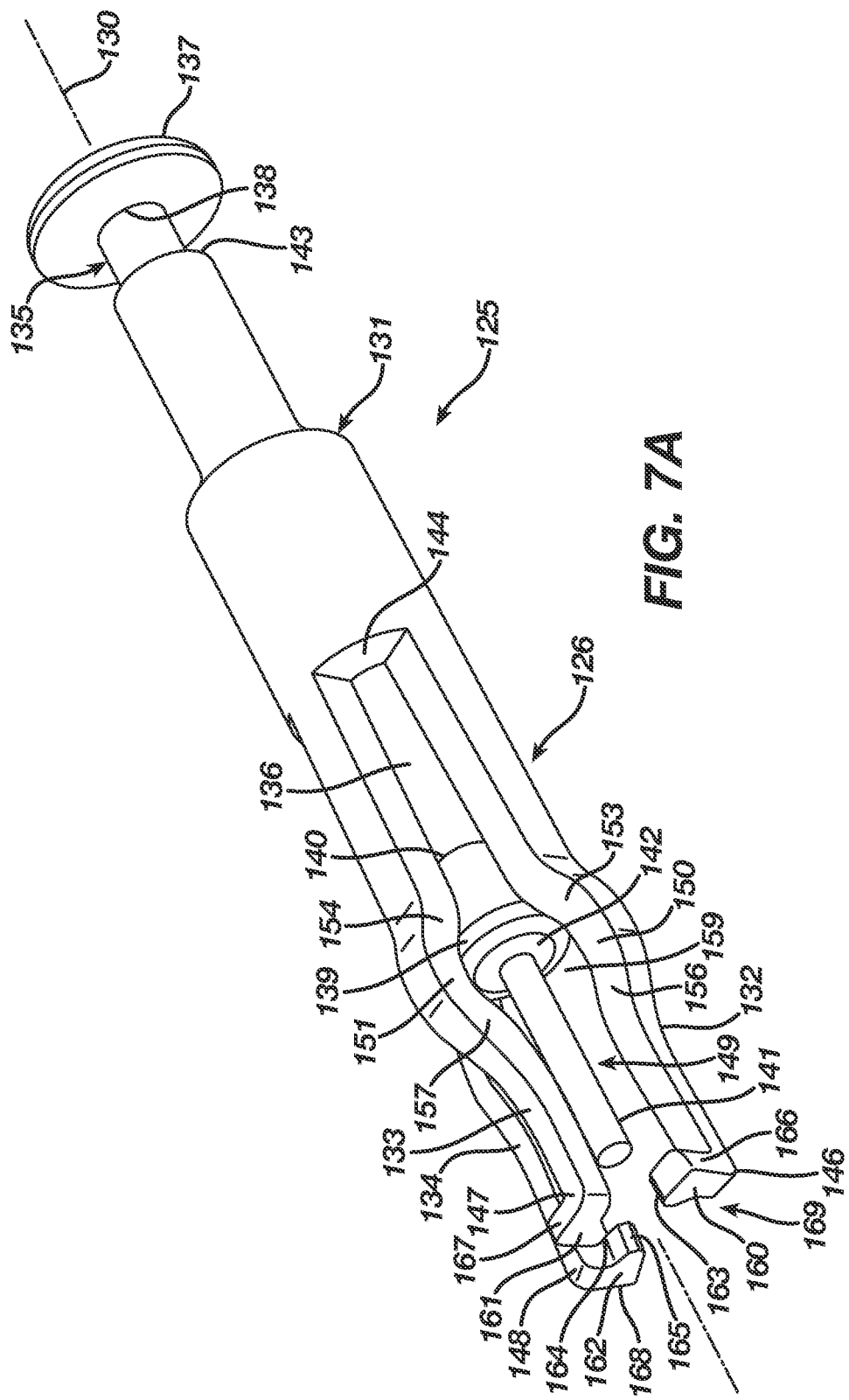
FIG. 7A is an isometric view illustrating an implant delivery device for the radially compressive shape memory implant according to the first embodiment residing in an implant release position.
Figure 7B:
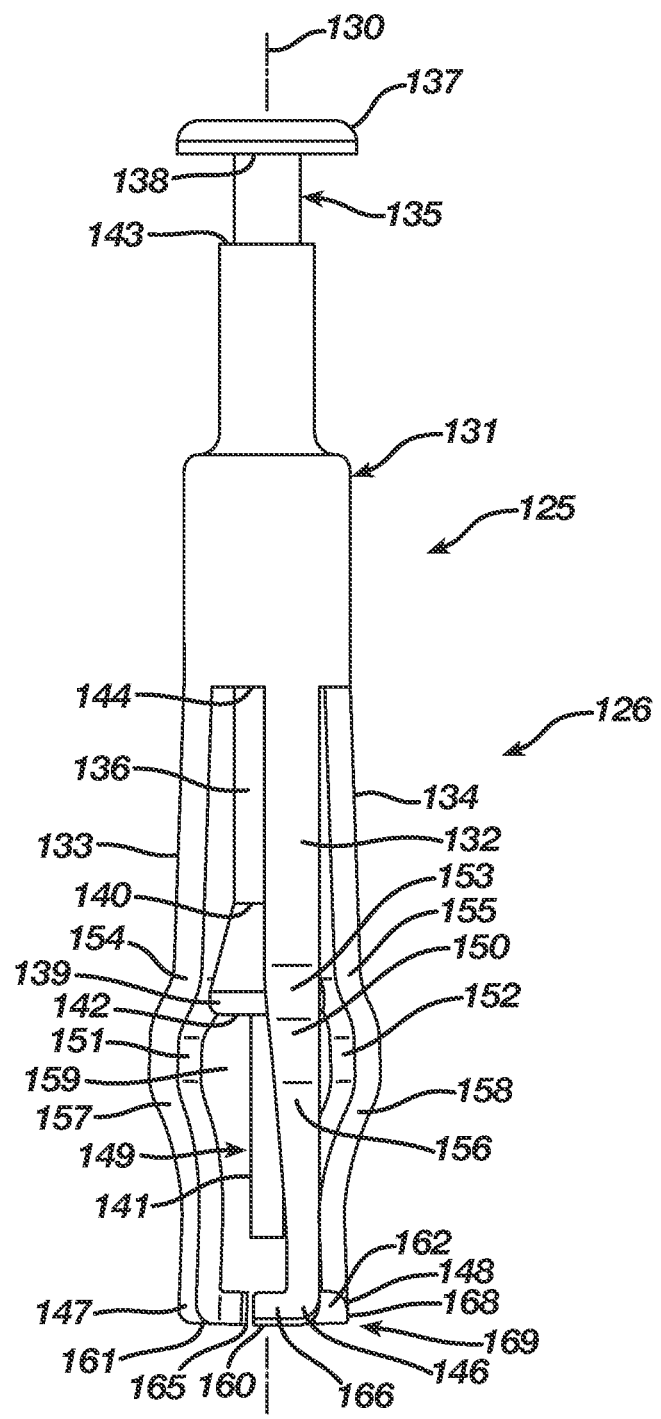
FIG. 7B is a side view illustrating the implant delivery device for the radially compressive shape memory implant according to the first embodiment residing in the implant release position.
Figure 7C:
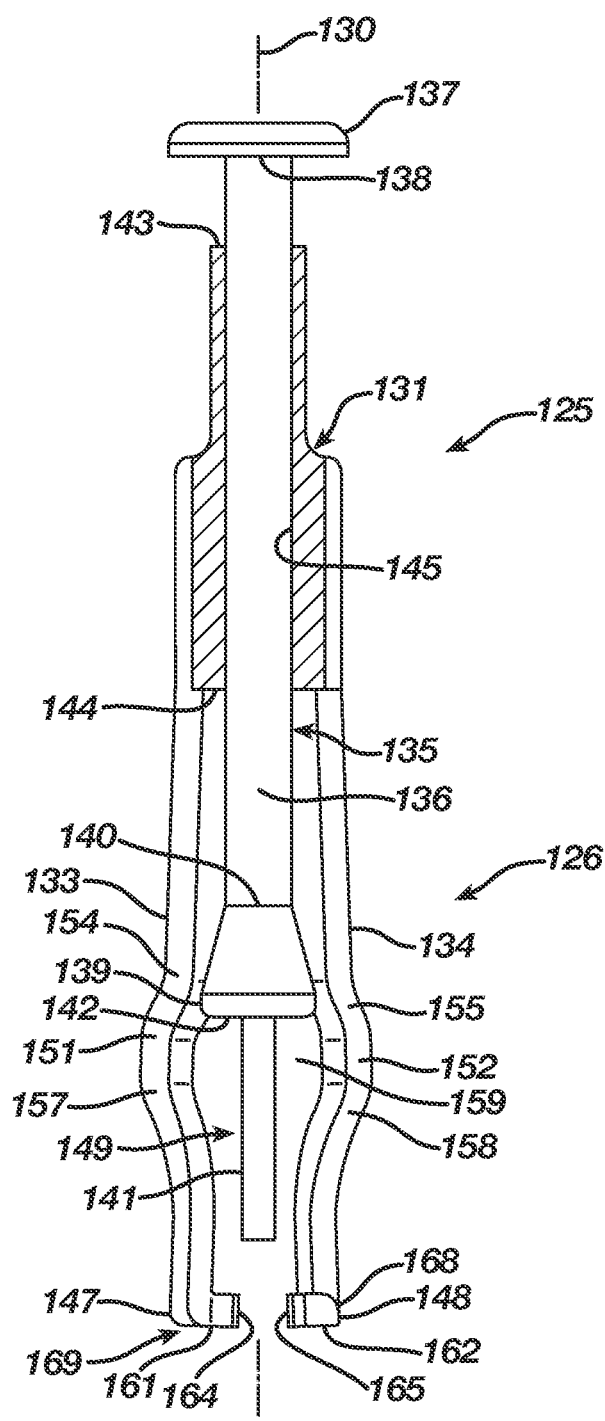
FIG. 7C is a side view in partial cross-section illustrating the implant delivery device for the radially compressive shape memory implant according to the first embodiment residing in the implant release position.

Referring to FIGS. 5A-5E, the regular inherent shape of the implant 80 is its natural shape 81 where the transition sections 102-106 locate the bridge 83 in a natural form that, as illustrated in FIG. 5D, respectively places each of the first, second, third, fourth, and fifth bridge segments 87-91 at a first angle 115 measured from a plane perpendicular to the central vertical axis 85. More particularly, each transition section 102-106 locates a respective screw 110-114 inserted through a respective opening 97-101 in a natural position whereby each of the screws 110-114 resides from the central vertical axis 55 at a first distance 117 as illustrated in FIG. 5B. Additionally, the screws 110-114 when residing in their natural position are spaced about the central vertical axis 85 equidistant or at least substantially equidistant due to the symmetrical configuration of the bridge segments 87-91 comprising the bridge 83. Nevertheless, referring to FIGS. 6A-6E, the implant 80 is deformable under the action of superelasticity or temperature dependent shape memory to the insertion shape 82 where the transition sections 102-106 deform to store energy while also moving the bridge 83 from its natural form to an insertion form that, as illustrated in FIG. 6D, respectively places each of the first, second, third, fourth, and fifth bridge segments 87-91 at a second angle 116 measured from a plane perpendicular to the central vertical axis 85 that is greater than the first angle 115. More particularly, each transition section 102-106 moves a respective screw 110-114 inserted through a respective opening 97-101 linearly away from the central vertical axis 85 from the natural position to an insertion position whereby each of the screws 110-114 resides from the central vertical axis 85 at a second distance 118 as illustrated in FIG. 6B that is greater than the first distance 117. Additionally, the screws 110-114 when residing in their insertion position also are spaced about the central vertical axis 85 equidistant or at least substantially equidistant due to the linear movement of the screws 110-114 relative to the central vertical axis 85 and the symmetrical configuration of the bridge segments 87-91 comprising the bridge 83.

Since the insertion shape 82 is not the regular inherent shape of the implant 80, the implant 80 typically is mechanically constrained using an implant delivery device that maintains the bridge 83 in its insertion form and thus the screws 110-114 in their insertion position. The bridge 83 at the respective ends 92-96 of the bridge segments 87-91 includes the interlocks 107 in order to facilitate engagement of an implant delivery device of the present invention with the implant 80. Upon deformation of the transition sections 102-106, the implant delivery device engages the bridge segments 87-91 via the interlocks 107 at the ends 92-96 thereby constraining the bridge 83 and thus the deformed transition sections 102-106 such that the implant delivery device maintains the implant 80 in its insertion shape 82.

After implantation of the implant 80 in its insertion shape 82 into bone, bones, or bone pieces and a release thereof, including, if necessary, a heating of the implant 80, the implant 80 in an attempted transition to its natural shape 81 delivers the energy stored in the transition sections 102-106, resulting in the bridge 83, due to the transition sections 102-106, attempting to transition from its insertion form to its natural form. The screws 110-114, accordingly, attempt to move from their insertion position to their natural position whereby the implant 80 affixes the bone, bones, or bone pieces through an application of a radial compressive force thereto. More particularly, each transition section 102-106 attempts to move a respective screw 110-114 inserted through a respective opening 97-101 linearly toward the central vertical axis 85 such that the implant 80 through this attempted convergence of the screws 110-114 imparts a radial compressive force to the bone, bones, or bone pieces.

The implant 80 in the third embodiment applies a continuously compressive radial force to the bone, bones, or bone pieces at a central fixation zone thereby facilitating a fixation thereof due to the symmetrical arrangement of the bridge segments 87-91 about the central vertical axis 85 and the transition sections 102-106 that impart, respectively, linear movement to the screws 110-114 relative to the central vertical axis 85. In accordance therewith, the screws 110-114 diverge from the central vertical axis 85 when transitioning from their natural position to their insertion position and converge toward the central vertical axis 85 when transitioning from their insertion position to their natural position such that the screws 110-114 are spaced apart substantially equidistant about the central vertical axis 85 in both their natural and insertion positions. Consequently, upon implantation of the implant 80 in its insertion shape 82 into the bone, bones, or bone pieces with the bridge 83 traversing a central fixation zone of the bone, bones, or bone pieces followed by a release of the implant 80, the transition sections 102-106, respectively, impart the energy stored therein to the screws 110-114 such that the screws 110-114 attempt linear movement resulting in an attempted convergence of the screws 110-114 toward the central vertical axis 85 whereby the implant 80, via the attempted transition from its insertion shape 82 to its natural shape 81 due to the transition sections 102-106 and the attempted convergence of the screws 110-114, applies a continuously compressive radial force to the bone, bones, or bone pieces at the central fixation zone in order to fixate the bone, bones, or bone pieces at the central fixation zone.

FIGS. 7A-9G illustrate an implant delivery device 125 configured to engage an implant 5 according to the first embodiment and constrain the implant 5 in its insertion shape 7 such that the implant 5 may be implanted in bone, bones, or bone pieces during a surgical operation. The implant delivery device 125 resides in either an implant release position 126 as illustrated in FIGS. 7A-7C and 9G or an implant engagement position 127 as illustrated in FIGS. 8A-8C and 9A-9B and is movable therebetween through a transitional position 128 as illustrated in FIGS. 9C-9F. The implant delivery device 125 when residing in the implant release position 126 releases the implant 5 whereby the implant 5 disengages from the implant delivery device 125 without obstruction. Conversely, the implant delivery device 125 when residing in the implant engagement position 127 engages the implant 5 and maintains the implant 5 constrained in its insertion shape 7. In addition, the implant delivery device 125 allows a surgeon to manipulate the implant 5 and implant the implant 5 into bone, bones, or bone pieces requiring fixation.

The implant delivery device 125 about at a central vertical axis 130 thereof includes a barrel 131 with a first finger 132, a second finger 133, and a third finger 134 extending therefrom and a plunger 135 integrated with the barrel 131 and the first, second, and third fingers 132-134. The plunger 135 includes a shaft 136 with a head 137 atop a first or top end 138 of the shaft 136 and a protrusion 139 at a second or bottom end 140 of the shaft 136 and further a rod 141 extending from the protrusion 139 at a bottom 142 thereof. The plunger 135 includes the head 137 to restrict movement of the shaft 136 relative to the barrel 131 and the first, second, and third fingers 132-134. The plunger 135 includes the protrusion 139, which is preferably of a bulbous shape distended at the bottom 142, in order to facilitate an interface of the plunger 135 with the first, second, and third fingers 132-134. The plunger 135 includes the rod 141 to facilitate an interface of the plunger 135 with the first, second, and third fingers 132-134 and with an implant 5 according to the first embodiment.

The barrel 131 includes a first or top end 143, a second or bottom end 144, and a channel 145 therebetween configured to receive therethrough the plunger 135 at the shaft 136. The first finger 132 extends from the second or bottom end 144 of the barrel 131 to a tip 146, the second finger 133 extends from the second or bottom end 144 of the barrel 131 to a tip 147, and the third finger 134 extends from the second or bottom end 144 of the barrel 131 to a tip 148. The extension of the first, second, and third fingers 132-134 from the second or bottom end 144 of the barrel 131 to a respective tip 146-148 forms a passageway 149 interior of the first, second, and third fingers 132-134 configured to receive therethrough the plunger 135 at the shaft 136, the protrusion 139, and the rod 141. More particularly, the first finger 132 includes a bend 150 beginning at a first or upper end 153 and stopping at a second or lower end 156, the second finger 133 includes a bend 151 beginning at a first or upper end 154 and stopping at a second or lower end 157, and the third finger 134 includes a bend 152 beginning at a first or upper end 155 and stopping at a second or lower end 158 in order to create an expansion 159 in the passageway 149 configured for the protrusion 139 of the plunger 135. The first finger 132, the second finger 133, and the third finger 134 preferably are symmetrical in that the first, second, and third fingers 132-134 are spaced about the central vertical axis 130 and the barrel 131 equidistant or at least substantially equidistant in order to facilitate interfacing of the first, second, and third fingers 132-134 with an implant 5. Moreover, the symmetry of the first, second, and third fingers 132-134 includes the first, second, and third fingers 132-134 being dimensionally identical or at least substantially, dimensionally identical; particularly with respect to length.

The first finger 132 at the tip 146 thereof includes an abutment 160, the second finger 133 at a tip 147 thereof includes an abutment 161, and the third finger 134 at a tip 148 thereof includes an abutment 162. The abutments 160-162 preferably extend perpendicular to or at least substantially perpendicular to the first, second, third fingers 132-134, respectively, at the tips 146-148 thereof. The abutment 160 includes a rod interface 163 that faces toward the central vertical axis 130 and an implant interface 166 that resides opposite to the rod interface 163 and thus faces away from the central vertical axis 130. The abutment 161 includes a rod interface 164 that faces toward the central vertical axis 130 and an implant interface 167 that resides opposite to the rod interface 164 and thus faces away from the central vertical axis 130. The abutment 162 includes a rod interface 165 that faces toward the central vertical axis 130 and an implant interface 161 that resides opposite to the rod interface 165 and thus faces away from the central vertical axis 130. The abutments 160-162 include the rod interfaces 163-165 to facilitate an engagement of the abutments 160-162 in an abutting relationship with the rod 141 of the plunger 135 and the implant interfaces 166-168 to facilitate an engagement of the abutments 160-162 in an abutting relationship with the implant 5, and, in particular, respectively, with the legs 25-27 of the implant 5, such that the implant delivery device 125 constrains the implant 5 in the insertion shape 7. The rod interfaces 163-165 and the implant interfaces 166-168 of the abutments 160-162, preferably, and due to the symmetry of the first, second, and third fingers 132-134, are spaced about the central vertical axis 130 and the barrel 131 equidistant or at least substantially equidistant in order to facilitate engagement of the rod interfaces 163-165 with the rod 141 of the plunger 135 and the implant interfaces 166-168 with an implant 5, and, in particular, respectively, with the legs 25-27 of the implant 5.

In integrating the plunger 135 with the barrel 131 and the first, second, and third fingers 132-134, the plunger 135 at the shaft 136 inserts through the channel 145 of the barrel 131 and into the passageway 149 defined by the first, second, and third fingers 132-134 while the head 137 atop the shaft 136 remains above the barrel 131 at the first or top end 143 thereof. The shaft 136 includes a length that locates the protrusion 139 of the plunger 135 in the expansion 159 of the passageway 149 created by the bends 150-152 of the first, second, and third fingers 132-134. Moreover, the rod 141 of the plunger 135 includes a length that permits the rod to interface with an implant 5 and with the abutments 160-162 of the first, second, and third fingers 132-134 at the rod interfaces 163-165.

When the implant delivery device 125 resides in the implant release position 126 as illustrated in FIGS. 7A-7C and 9G, the plunger 135 retracts from the barrel 131 until the head 137 atop the shaft 136 is positioned above the barrel 131 at the first or top end 143 thereof, resulting in a movement of the protrusion 139 adjacent and in abutment with the first or upper ends 153-155 of the bends 150-152 and a movement of the rod 141 above the abutments 160-162 of the first, second, and third fingers 132-134 as well as the bridge 8 of an implant 5. The location of the protrusion 139 adjacent and in abutment with the first or upper ends 153-155 of the bends 150-152 expands the first, second, and third fingers 132-134 and thus the abutments 160-162 thereof to a disengaged position 169 whereby the abutments 160-162 are spaced apart from the central vertical axis 130 a distance sufficient for the abutments 160-162 to bypass the bridge 8 of the implant 5 at respective first, second, and third bridge segments 12-14 thereof. Similarly, movement of the rod 141 to a location above the abutments 160-162 disengages the rod 141 from the bridge 8 of the implant 5 at the aperture 9 thereof. The bypassing of the bridge 8 by the abutments 160-162 and the disengagement of the rod 141 from the bridge 8 releases the implant 5 from the implant delivery device 125.

Figure 8A:
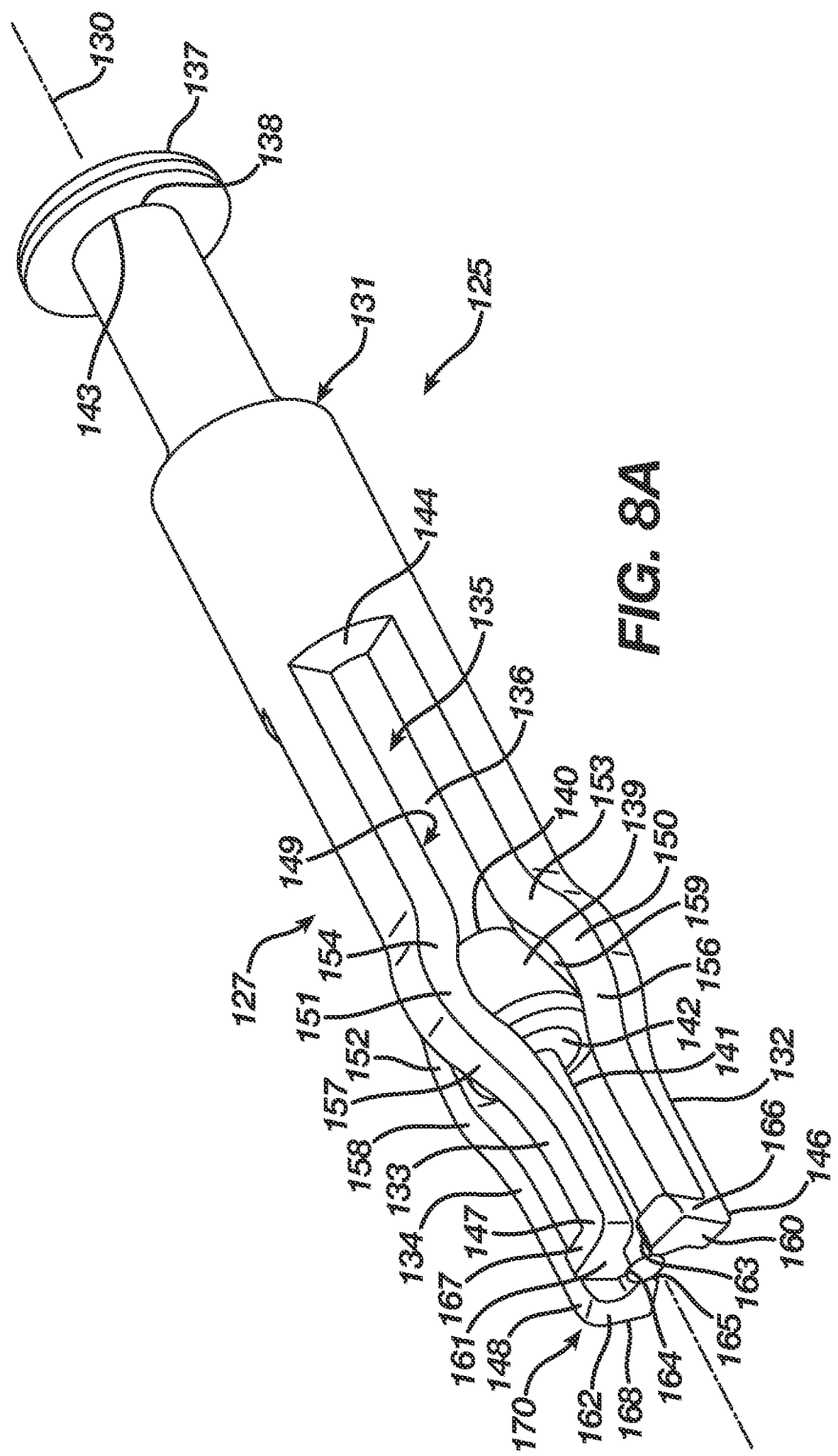
FIG. 8A is an isometric view illustrating the implant delivery device for the radially compressive shape memory implant according to the first embodiment residing in an implant engagement position.
Figure 8B:
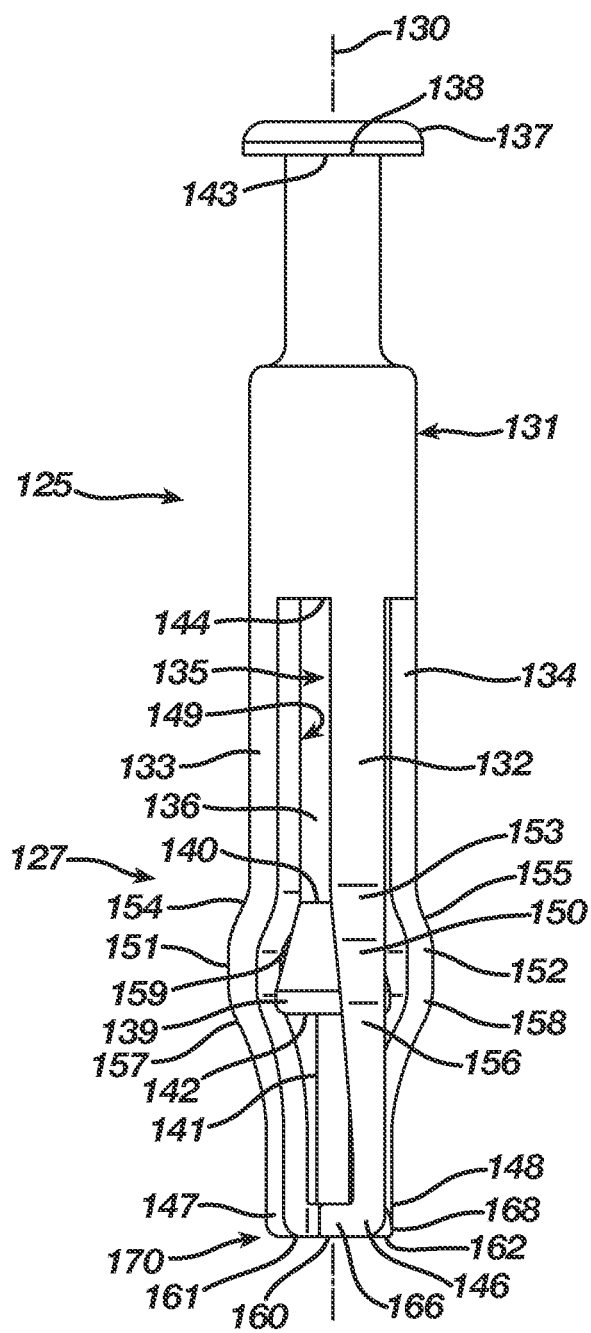
FIG. 8B is a side view illustrating the implant delivery device for the radially compressive shape memory implant according to the first embodiment residing in the implant engagement position.
Figure 8C:
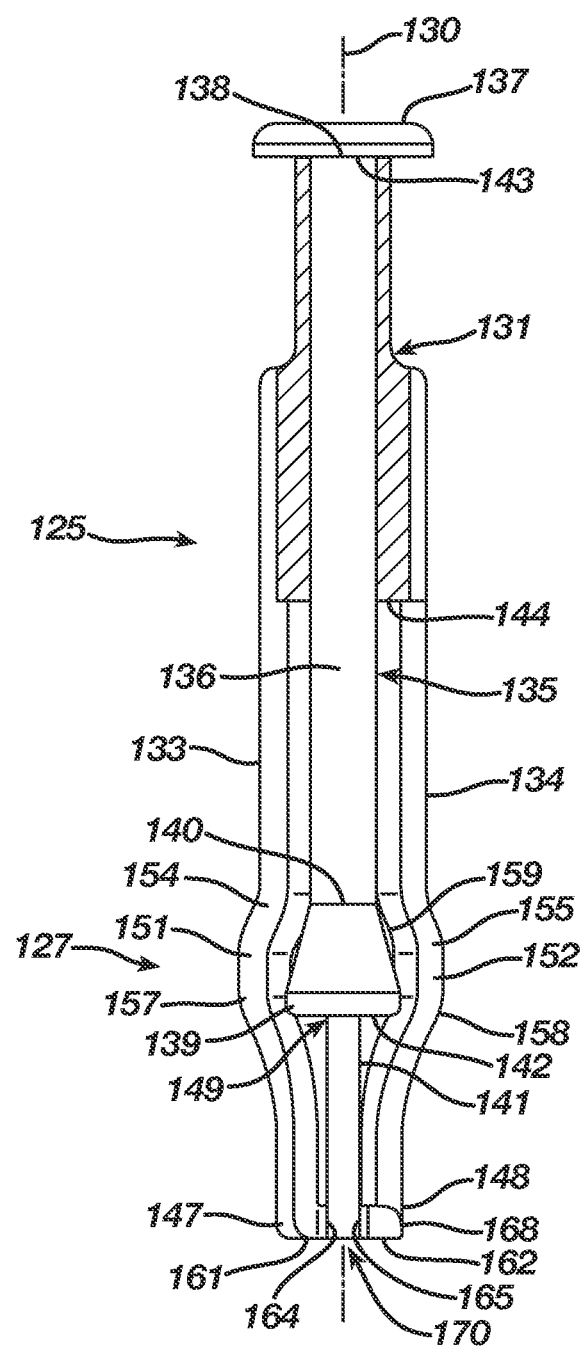
FIG. 8C is a side view in partial cross-section illustrating the implant delivery device for the radially compressive shape memory implant according to the first embodiment residing in the implant engagement position.

Conversely, when the implant delivery device 125 resides in the implant engagement position 127 as illustrated in FIGS. 8A-8C, the plunger 135 advances into the barrel 131 until the head 137 atop the shaft 136 abuts the barrel 131 at the first or top end 143 thereof, resulting in a movement of the protrusion 139 adjacent and in abutment with the second or lower ends 156-158 of the bends 150-152 and a movement of the rod 141 through the aperture 9 of an implant 5 to a position adjacent and in abutment with the rod interfaces 163-165 of the abutments 160-162 for the first, second, and third fingers 132-134. The location of the protrusion 139 adjacent and in abutment with the second or lower ends 156-158 of the bends 150-152 and the rod 141 adjacent and in abutment with the rod interfaces 163-165 of the abutments 160-162 expands the first, second, and third fingers 132-134 and the abutments 160-162 thereof to an engaged position 170 whereby the abutments 160-162 are spaced apart from the central vertical axis 130 a distance sufficient for the abutments 160-162 at the implant interfaces 166-168, respectively, to abut the implant 5, and, in particular, the legs 25-27 thereof. The insertion of the rod 141 through the aperture 9 of the bridge 8 and the resulting abutment of the implant interfaces 166-168, respectively, with the legs 25-27 of the implant 5 engage the implant delivery device 125 with the implant 5 in the implant engagement position 127 such that the implant delivery device 125 constrains the implant 5 in the insertion shape 7.

In order for the implant delivery device 125 to transition between the implant release position 126 and the implant engagement position 127, the implant delivery device 125 includes the transitional position 128 illustrated in FIGS. 9C-9F. The implant delivery device 125 progresses to the transitional position 128 from the implant engagement position 127 through a retraction of the plunger 135 relative to the barrel 131 until the protrusion 139 moves from the second or lower ends 156-158 of the bends 150-152 into the expansion 159 defined by the bends 150-152 and the rod 141 moves to discontinue abutment with the rod interfaces 163-165 of the abutments 160-162 while remaining disposed within the aperture 9 of the bridge 8 for the implant 5. Alternatively, the implant delivery device 125 progresses to the transitional position 128 from the implant release position 126 through an advancing of the plunger 135 relative to the barrel 131 until the protrusion 139 moves from the first or upper ends 153-155 of the bends 150-152 into the expansion 159 defined by the bends 150-152 and the rod 141 moves from above the implant 5 into the aperture 9 of the bridge 8 thereof. The location of the protrusion 139 adjacent the bends 150-152 in the expansion 159 with the rod 141 disengaged from the rod interfaces 163-165 of the abutments 160-162 collapses the first, second, and third fingers 132-134 and the abutments 160-162 thereof to an intermediate position 171 whereby the abutments 160-162 are spaced apart from the central vertical axis 130 a distance sufficient for the abutments 160-162 at the implant interfaces 166-168, respectively, to cease contact with the implant 5, and, in particular, with the legs 25-27 thereof. The abutments 160-162 in the intermediate position 171 are movable to facilitate either disengagement of the implant delivery device 125 from the legs 25-27 and thus the implant 5 or engagement of the implant delivery device 125 with the legs 25-27 and thus the implant 5 due to the removal of the abutments 160-162 from contact with the rod 141 and the legs 25-27 of the implant 5.

Figure 9A:
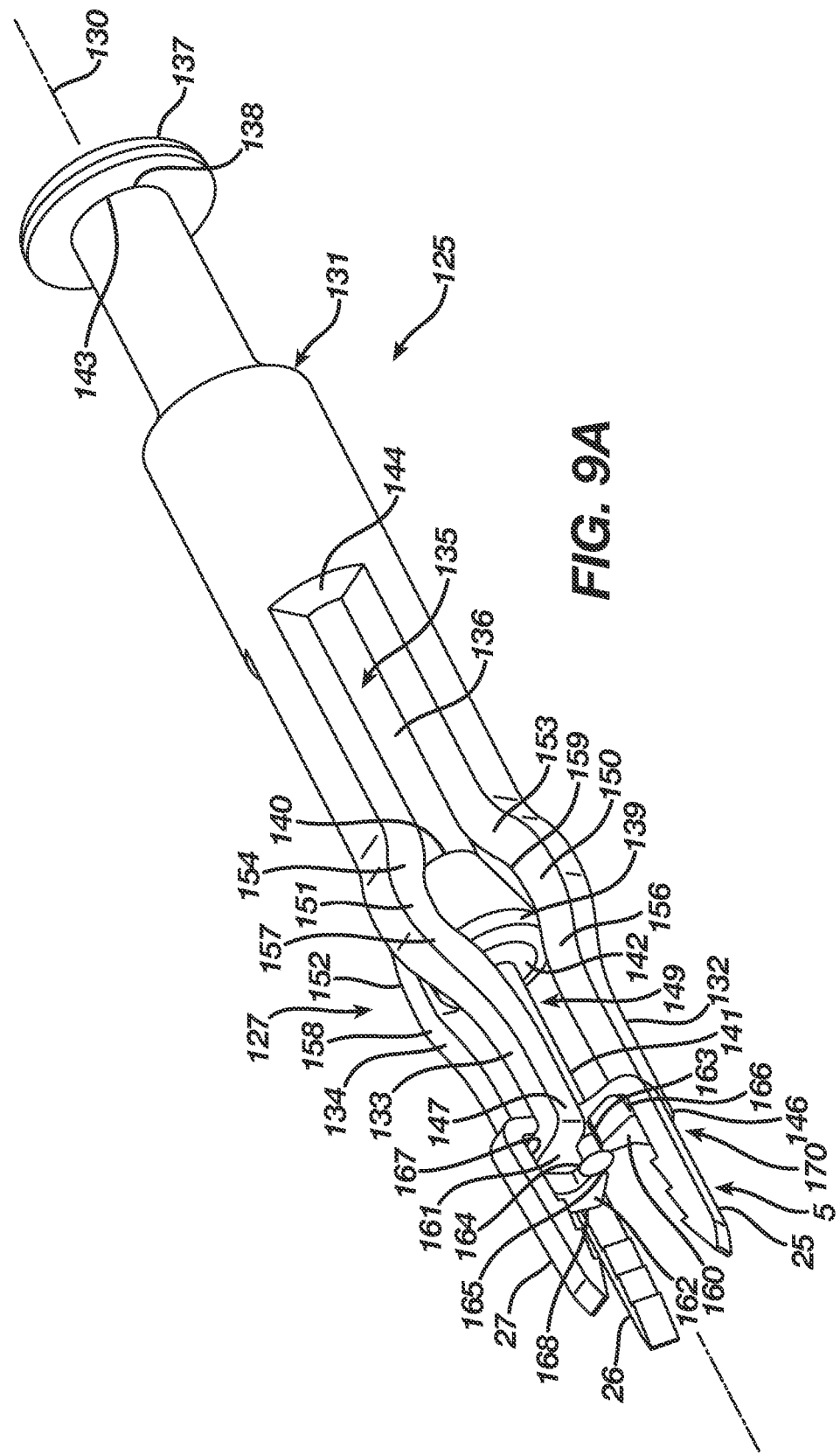
FIGS. 9A and 9B are isometric views illustrating the implant delivery device in the implant engagement position engaging the radially compressive shape memory implant according to the first embodiment.
Figure 9B:
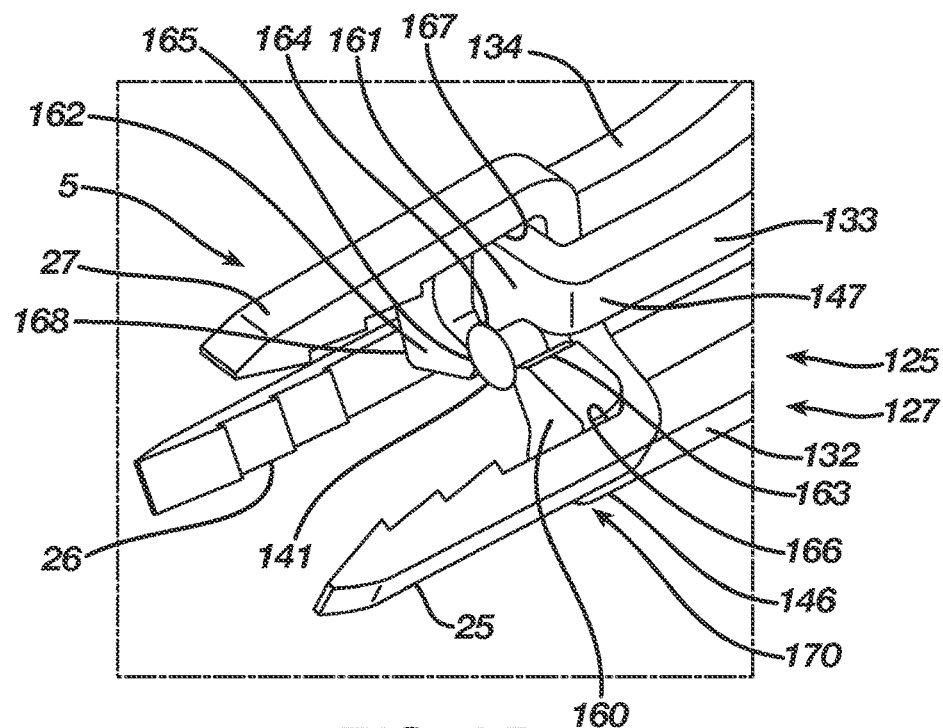
Figure 9C:
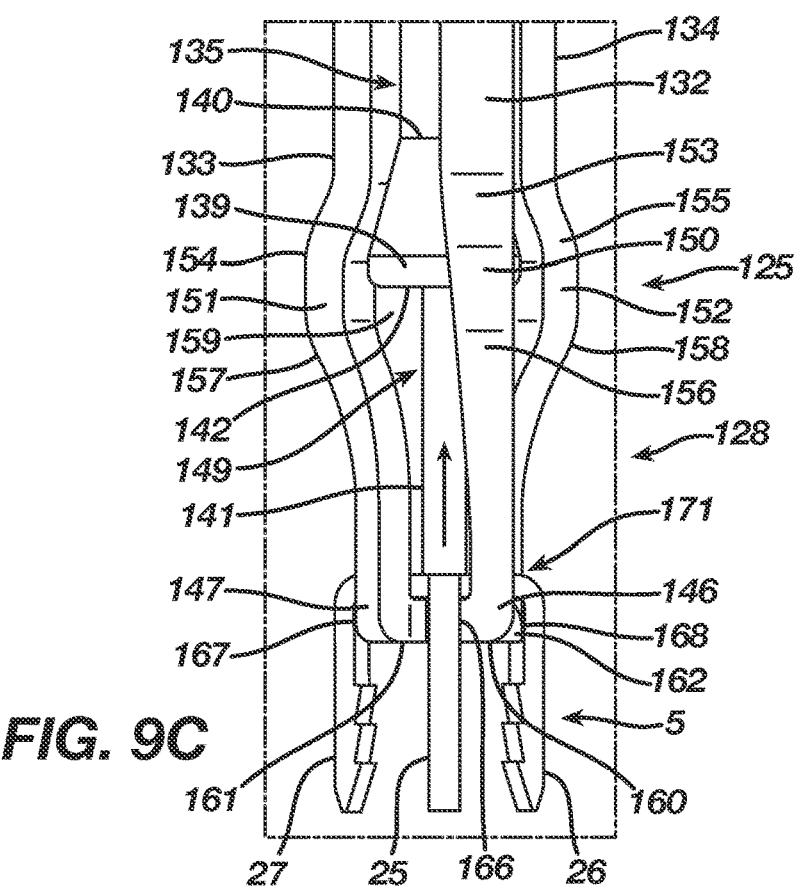
FIG. 9C is a side view illustrating a movement of the implant delivery device from the implant engagement position toward the implant release position in order to initiate a release of the radially compressive shape memory implant according to the first embodiment from the implant delivery device.
Figure 9D:
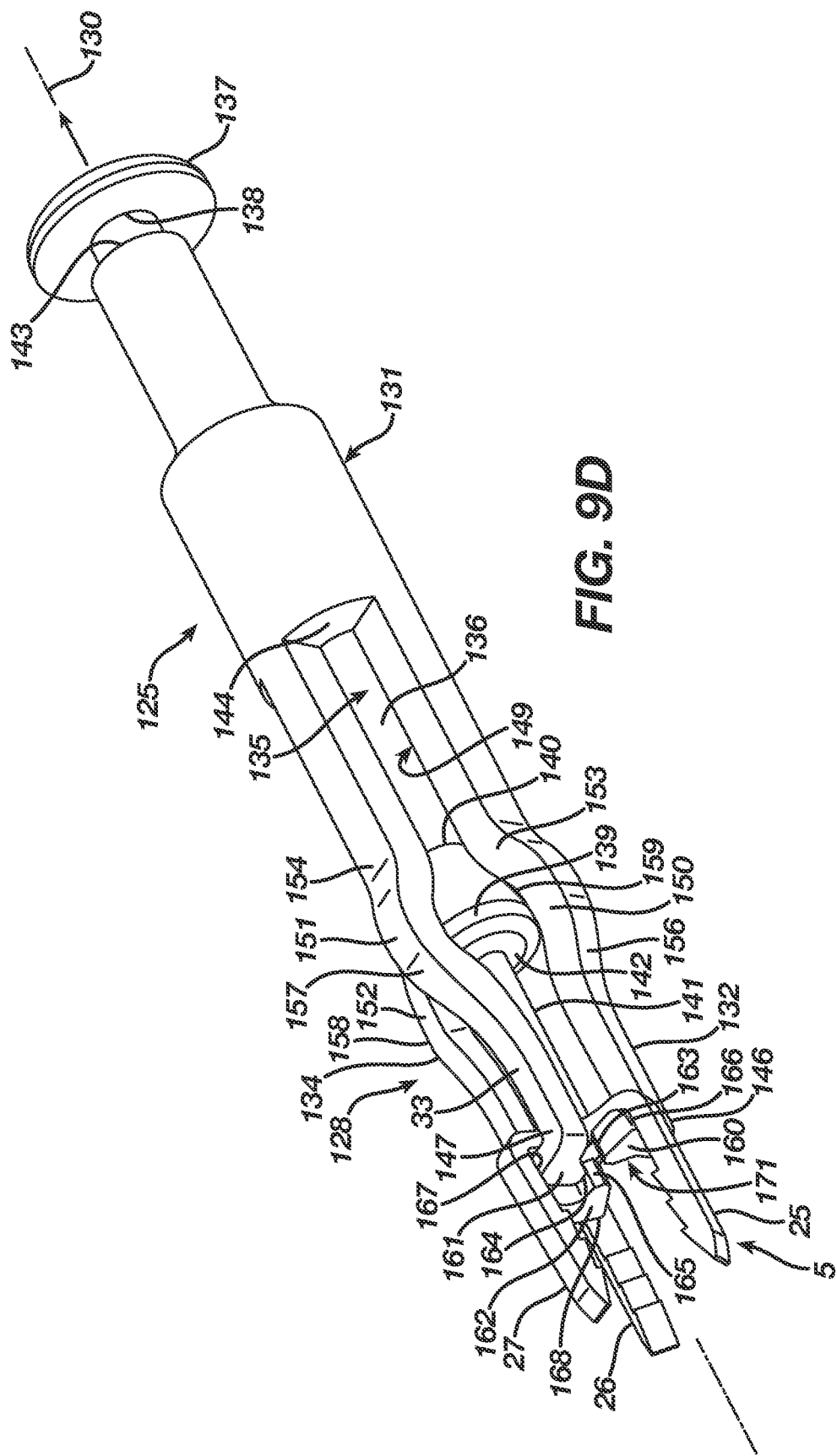
FIGS. 9D and 9E are isometric views illustrating the movement of the implant delivery device from the implant engagement position toward the implant release position in order to initiate the release of the radially compressive shape memory implant according to the first embodiment from the implant delivery device.
Figure 9E:
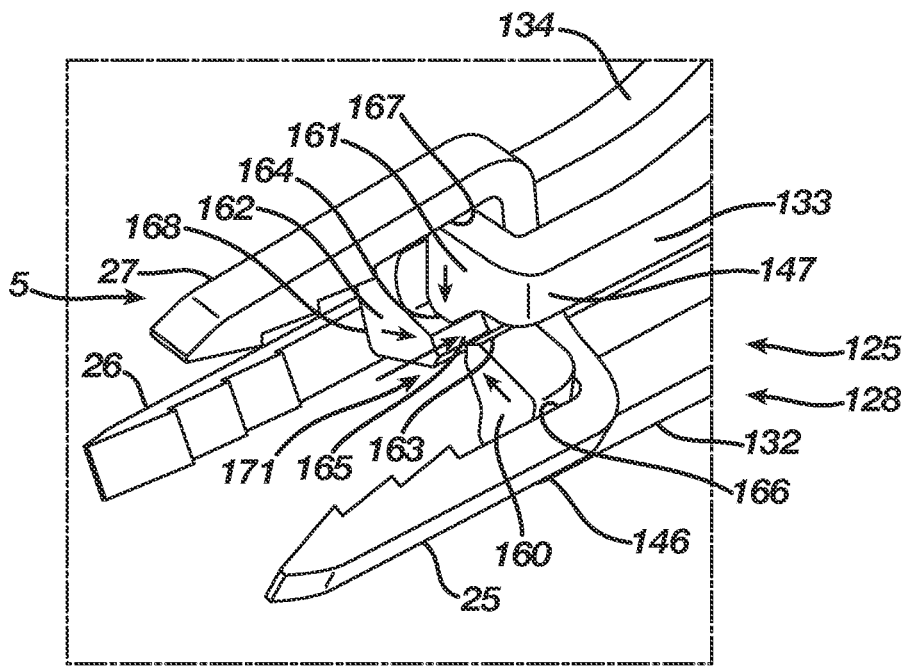
Figure 9F:
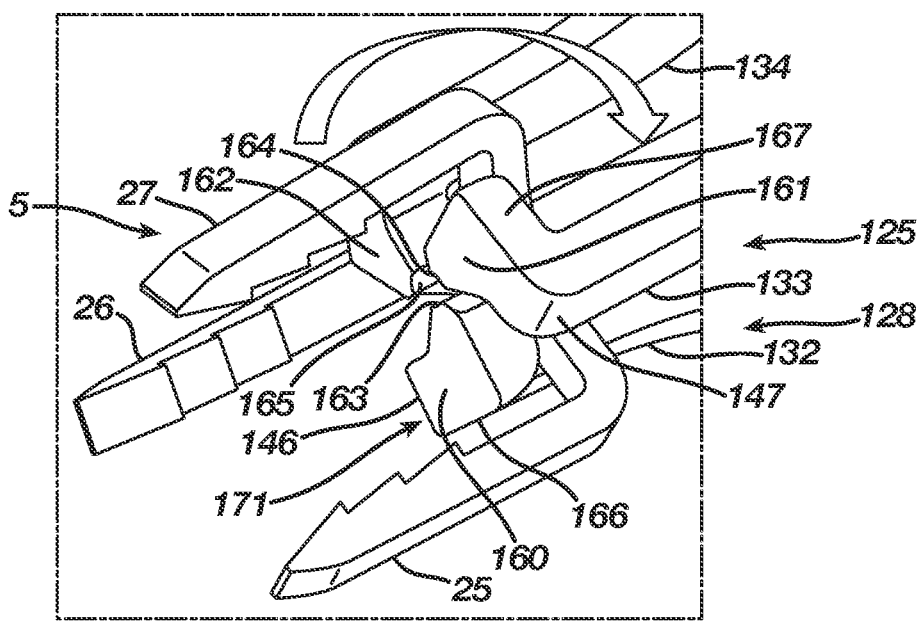
FIG. 9F is an isometric view illustrating a movement of the implant delivery device to the implant release position in order to release the radially compressive shape memory implant according to the first embodiment from the implant delivery device.
Figure 9G:
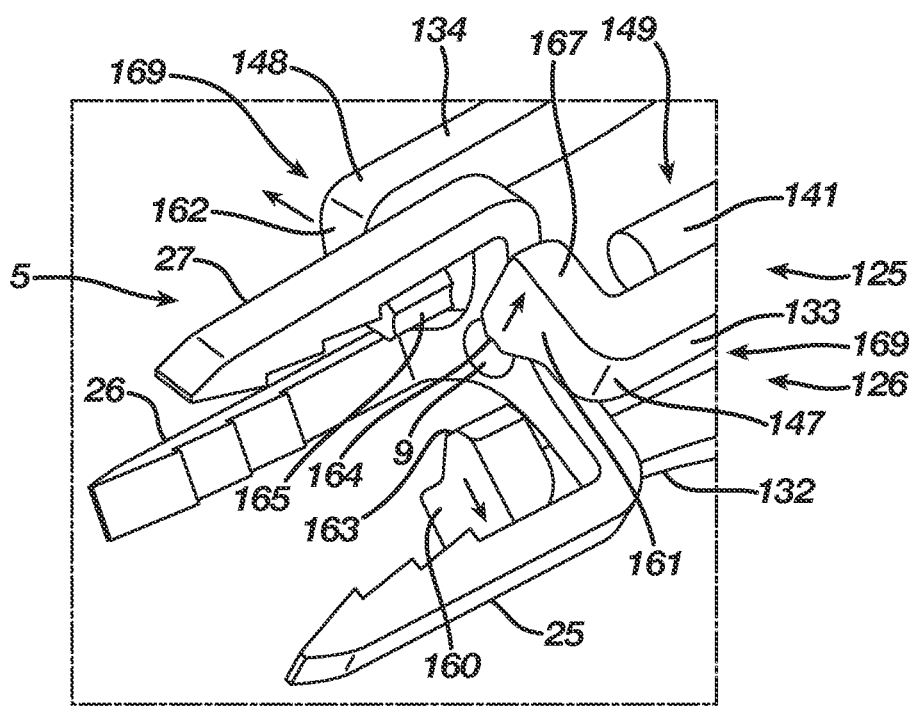
FIG. 9G is an isometric view illustrating the implant delivery device in the implant release position that releases the radially compressive shape memory implant according to the first embodiment from the implant delivery device.

The implant delivery device 125, when loaded with an implant 5 according to the first embodiment whereby the implant delivery device 125 in the implant engagement position 127 as illustrated in FIGS. 9A and 9B constrains the implant 5 in the insertion shape 7, delivers the implant 5 as follows. As illustrated in FIGS. 9C-9E, a retraction of the plunger 135 relative to the barrel 131 through a pulling on the head 137 moves the protrusion 139 from the second or lower ends 156-158 of the bends 150-152 into the expansion 159 defined by the bends 150-152. Concurrently, the rod 141 ceases its abutting relationship with the rod interfaces 163-165 of the abutments 160-162 while remaining disposed in the aperture 9 of the bridge 8 for the implant 5. Although the rod 141 stops supporting the abutments 160-162, the rod 141 remains in the aperture 9 of the bridge 8 in order to stabilize the implant 5 in the implant delivery device 125. With the protrusion 139 located in the expansion 159 defined by the bends 150-152 and the rod 141 retracted from the rod interfaces 163-165 of the abutments 160-162, the first, second, and third fingers 132-134 and the abutments 160-162 thereof collapse to the intermediate position 171, resulting in the abutments 160-162 at the implant interfaces 166-168, respectively, releasing the legs 25-27 of the implant 5. Once the abutments 160-162 at the implant interfaces 166-168, respectively, separate from the legs 25-27, the implant delivery device 125 as illustrated in FIG. 9F rotates, which, in the illustrated embodiment of the implant delivery device 125, is clockwise, about the central vertical axis 130 until the abutments 160-162 at the implant interfaces 166-168, respectively, travel from a position in alignment with the legs 25-27 to an unaligned position remote therefrom. After the abutments 160-162 separate from the legs 25-27 and rotate to an unaligned position remote from the legs 25-27, a further retraction of the plunger 135 relative to the barrel 131 through a pulling on the head 137 moves the protrusion 139 from the expansion 159 defined by the bends 150-152 to a location adjacent and in abutment with the first or upper ends 153-155 of the bends 150-152. Concurrently, the rod 141 moves from the aperture 9 of the bridge 8 such that the rod 141 releases the bridge 8 and thus the implant 5 while also remaining separated from the implant interfaces 166-168 of the abutments 160-162. With the protrusion 139 located adjacent and in abutment with the first or upper ends 153-155 of the bends 150-152, the first, second, and third fingers 132-134 and thus the abutments 160-162 thereof expand to the disengaged position 169, resulting in the abutments 160-162 as illustrated in FIG. 9G traveling away from the central vertical axis 130 to a position remote, respectively, from the bridge 8 of the implant 5 at the first, second, and third bridge segments 12-14 thereof. Once the abutments 160-162, respectively, separate to a position remote from the first, second, and third bridge segments 12-14 of the bridge 8, the implant delivery device 125 in the implant release position 126 releases the implant 5 through a movement of the implant delivery device 125 whereby the abutments 160-162, respectively, bypass the bridge 8 of the implant 5 at the first, second, and third bridge segments 12-14 thereof. The released implant 5, now unconstrained, attempts to transition from the insertion shape 7 to the natural shape 6 such that the implant 5 delivers the energy stored therein to bone, bones, or bone pieces in order to affix the bone, bones, or bone pieces through a radially compress thereof thereby promoting a healing of bone, bones, or bone pieces.

The implant delivery device 125, when residing in the implant release position 126 as illustrated in FIGS. 7A-7C and 9G, loads with an implant 5 according to the first embodiment placed in the insertion shape 7 as follows. The protrusion 139 in the implant release position 126 is located adjacent and in abutment with the first or upper ends 153-155 of the bends 150-152 while the rod 141 resides above the abutments 160-162 of the first, second, and third fingers 132-134. In accordance therewith, the abutments 160-162 begin separated and spaced apart from the central vertical axis 130 a distance sufficient for the abutments 160-162, respectively, to bypass the bridge 8 of the implant 5 at the first, second, and third bridge segments 12-14 thereof. The implant delivery device 125, which initially is placed above the bridge 8 of the implant 5 with the abutments 160-162, respectively, offset from the first, second, and third bridge segments 12-14 of the bridge 8, moves such that the abutments 160-162, respectively, bypass the first, second, and third bridge segments 12-14 until the abutments 160-162, respectively, reside below the first, second, and third bridge segments 12-14. An advancement of the plunger 135 relative to the barrel 131 through a pushing on the head 137 moves the protrusion 139 from the first or upper ends 153-155 of the bends 150-152 into the expansion 159 defined by the bends 150-152. Concurrently, the rod 141 progresses into the aperture 9 of the bridge 8 in order to stabilize the implant 5 in the implant delivery device 125. With the protrusion 139 located in the expansion 159 defined by the adjacent the bends 150-152, the first, second, and third fingers 132-134 and the abutments 160-162 thereof collapse to the intermediate position 171, resulting in the abutments 160-162 at the implant interfaces 166-168, respectively, moving to an unaligned position remote from the legs 25-27 of the implant 5 but interior thereto. Once the abutments 160-162 at the implant interfaces 166-168, respectively, reside in the unaligned position remote from the legs 25-27 of the implant 5 but interior thereto, the implant delivery device 125 rotates, which, in the illustrated embodiment of the implant delivery device 125, is counterclockwise, about the central vertical axis 130 until the abutments 160-162 at the implant interfaces 166-168, respectively, travel from the unaligned position remote from the legs 25-27 of the implant 5 but interior thereto to a position in alignment with the legs 25-27 but separated therefrom. After the abutments 160-162 rotate to the position in alignment with the legs 25-27 but separated therefrom, a further advancement of the plunger 135 relative to the barrel 131 through a pushing on the head 137 until the head 137 sits atop the barrel 131 at the first or top end 143 thereof moves the protrusion 139 from the expansion 159 defined by the bends 150-152 to a location adjacent and in abutment with the second or lower ends 156-158 of the bends 150-152. Concurrently, the rod 141 moves through the aperture 9 of the bridge 8 and into an abutting relationship with the rod interfaces 163-165 of the abutments 160-162. With the protrusion 139 located adjacent and in abutment with the second or lower ends 156-158 of the bends 150-152 and the rod 141 abutting the rod interfaces 163-165 of the abutments 160-162, the first, second, and third fingers 132-134 and thus the abutments 160-162 thereof expand to the engaged position 170, resulting in the abutments 160-162 traveling away from the central vertical axis 130 a distance sufficient for the abutments 160-162 at the implant interfaces 166-168, respectively, to abut the implant 5, and, in particular, the legs 25-27 thereof. The implant delivery device 125, now residing in the implant engagement position 127 with the rod 141 supporting the abutments 160-162, respectively, against the legs 25-27 at the implant interfaces 166-168, constrains the implant 5 in the insertion shape 7 whereby the implant 5 stores energy deliverable to bone, bones, or bone pieces. While the implant delivery device 125 loads with an implant 5 maintained in the insertion shape 7, one of ordinary skill in the art will recognize the implant delivery device 125 loads with an implant 5 in the natural shape 6 in that the expansion of the first, second, and third fingers 132-134 and thus the abutments 160-162 to the engaged position 170 results in the first, second, and third fingers 132-134 at the abutments 160-162 acting upon the transition sections 18-20 via the legs 25-27 such that the legs 25-27 move in order to facilitate a transition of the implant 5 from the natural shape 6 to the insertion shape 7.

As illustrated in FIGS. 10A-10D, an implant delivery device 175 is substantially similar in design and operation relative to the implant delivery device 125 such that, for the sake of brevity, only differences therebetween will be described in detail herein. In accordance with the similar design and operation of the implant delivery device 175, one of ordinary skill in the art will recognize that like parts of the implant delivery device 175 labeled with like numerals of the implant delivery device 125 incorporate a design and function as previously set forth in the detailed description of the implant delivery device 125. Illustratively, the implant delivery device 175 is substantially similar in design and operation relative to the implant delivery device 125 in that the implant delivery device 175 about the central vertical axis 130 thereof includes the barrel 131 with the first finger 132, the second finger 133, and the third finger 134 extending therefrom and the plunger 135 integrated with the barrel 131 and the first, second, and third fingers 132-134. In accordance with the differences of the implant delivery device 175, the implant delivery device 175 is dissimilar to the implant delivery device 125 in that the implant delivery device 175 includes a fourth finger 176 extending from the barrel 131 whereby the plunger 135 integrates with the barrel 131 and the first, second, third, and fourth fingers 132-134 and 176. The implant delivery device 175 includes the fourth finger 176 in order for the implant delivery device 175 to engage an implant 50 according to the second embodiment and constrain the implant 50 in its insertion shape 52 such that the implant 50 may be implanted in bone, bones, or bone pieces during a surgical operation.

The fourth finger 176 extends from the second or bottom end 144 of the barrel 131 to a tip 177. The extension of the first, second, third, and fourth fingers 132-134 and 176 from the second or bottom end 144 of the barrel 131 to a respective tip 146-148 and 177 forms the passageway 149 interior of the first, second, third, and fourth fingers 132-134 and 176 configured to receive therethrough the plunger 135 at the shaft 136, the protrusion 139, and the rod 141. More particularly, the fourth finger 176 includes a bend 178 beginning at a first or upper end 179 and stopping at a second or lower end 180 in order to create with the bends 150-152 of the first, second, and third fingers 132-134 the expansion 159 in the passageway 149 configured for the protrusion 139 of the plunger 135. The first finger 132, the second finger 133, the third finger 134, and the fourth finger 176 preferably are symmetrical in that the first, second, third, and fourth fingers 132-134 and 176 are spaced about the central vertical axis 130 and the barrel 131 equidistant or at least substantially equidistant in order to facilitate interfacing of the first, second, third, and fourth fingers 132-134 and 176 with an implant 50. Moreover, the symmetry of the first, second, third, and fourth fingers 132-134 and 176 includes the first, second, third, and fourth fingers 132-134 and 176 being dimensionally identical or at least substantially, dimensionally identical; particularly with respect to length.

The fourth finger 176 at the tip 177 thereof includes an abutment 181 that preferably extends perpendicular to or at least substantially perpendicular to the fourth finger 176 at the tip 177 thereof. The abutment 181 includes a rod interface 182 that faces toward the central vertical axis 130 and an implant interface 183 that resides opposite to the rod interface 182 and thus faces away from the central vertical axis 130. The abutment 181 includes the rod interface 182 to facilitate an engagement of the abutment 181 in an abutting relationship with the rod 141 of the plunger 135 and the implant interface 183 to facilitate an engagement of the abutment 181 in an abutting relationship with the implant 50, and, in particular, with one of the legs 69-72 of the implant 50, such that the implant delivery device 175 constrains the implant 50 in the insertion shape 52. The rod interfaces 163-165 and 182 and the implant interfaces 166-168 and 183 of the abutments 160-162 and 181, preferably, and due to the symmetry of the first, second, third, and fourth fingers 132-134 and 176, are spaced about the central vertical axis 130 and the barrel 131 equidistant or at least substantially equidistant in order to facilitate engagement of the rod interfaces 163-165 and 182 with the rod 141 of the plunger 135 and the implant interfaces 166-168 and 183 with an implant 50, and, in particular, respectively, with the legs 69-72 of the implant 50.

In integrating the plunger 135 with the barrel 131 and the first, second, third, and fourth fingers 132-134 and 176, the plunger 135 at the shaft 136 inserts through the channel 145 of the barrel 131 and into the passageway 149 defined by the first, second, third, and fourth fingers 132-134 and 176 while the head 137 atop the shaft 136 remains above the barrel 131 at the first or top end 143 thereof. The shaft 136 includes a length that locates the protrusion 139 of the plunger 135 in the expansion 159 of the passageway 149 created by the bends 150-152 and 178 of the first, second, third, and fourth fingers 132-134 and 176. Moreover, the rod 141 of the plunger 135 includes a length that permits the rod to interface with an implant 50 and with the abutments 160-162 and 181 of the first, second, third, and fourth fingers 132-134 and 176 at the rod interfaces 163-165 and 183.

Figure 10A:
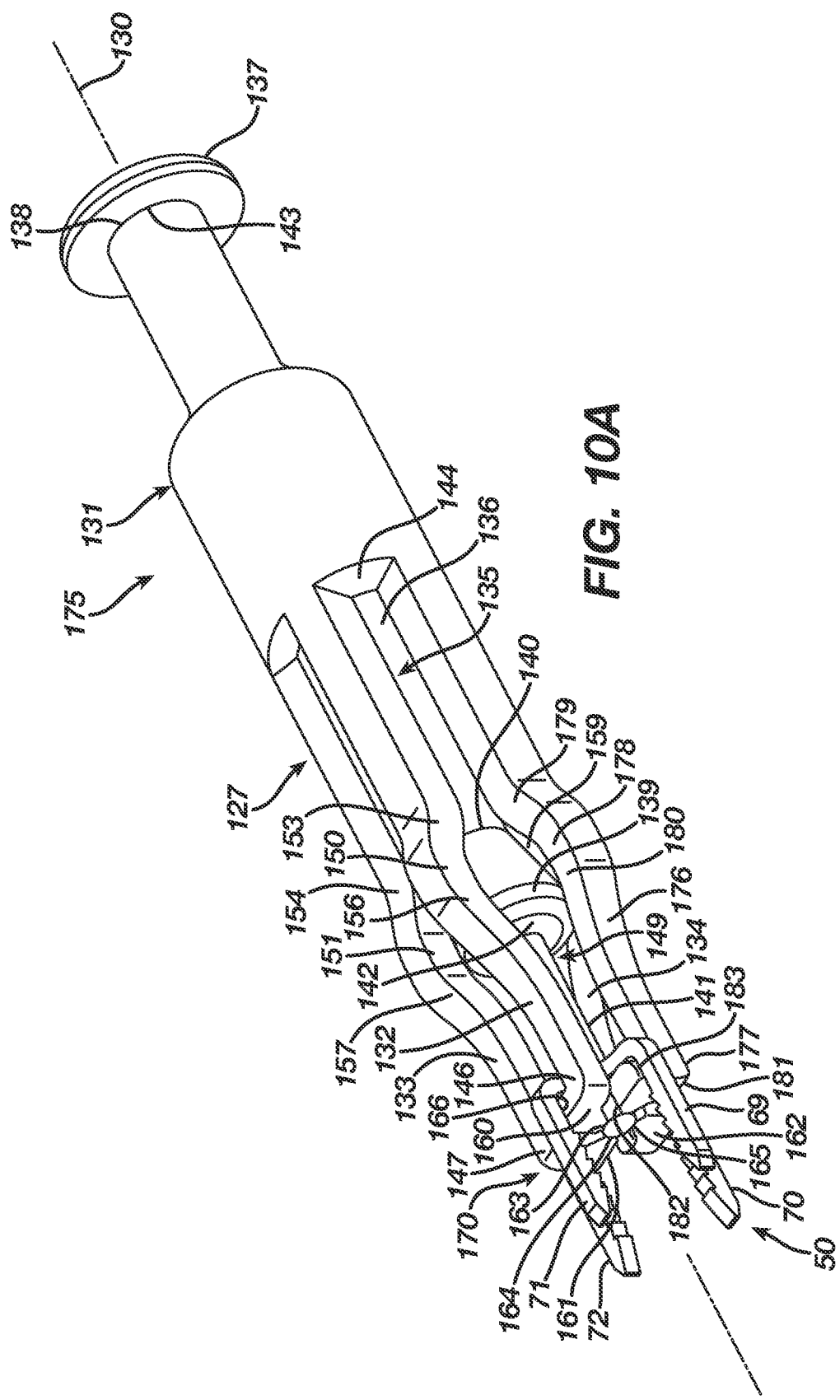
FIGS. 10A and 10B are isometric views illustrating an implant delivery device in an implant engagement position engaging the radially compressive shape memory implant according to the second embodiment.
Figure 10B:
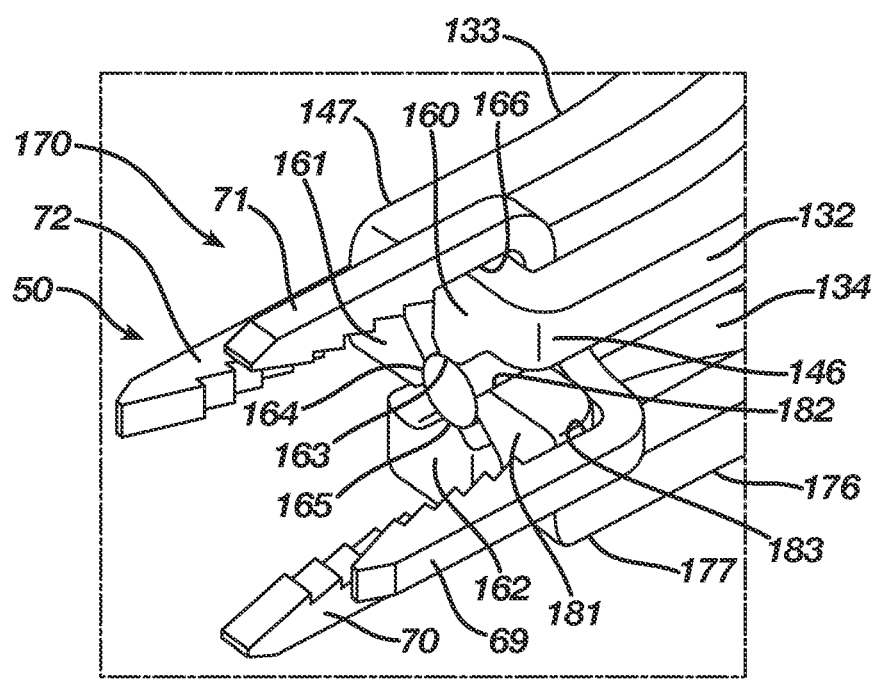
Figure 10C:
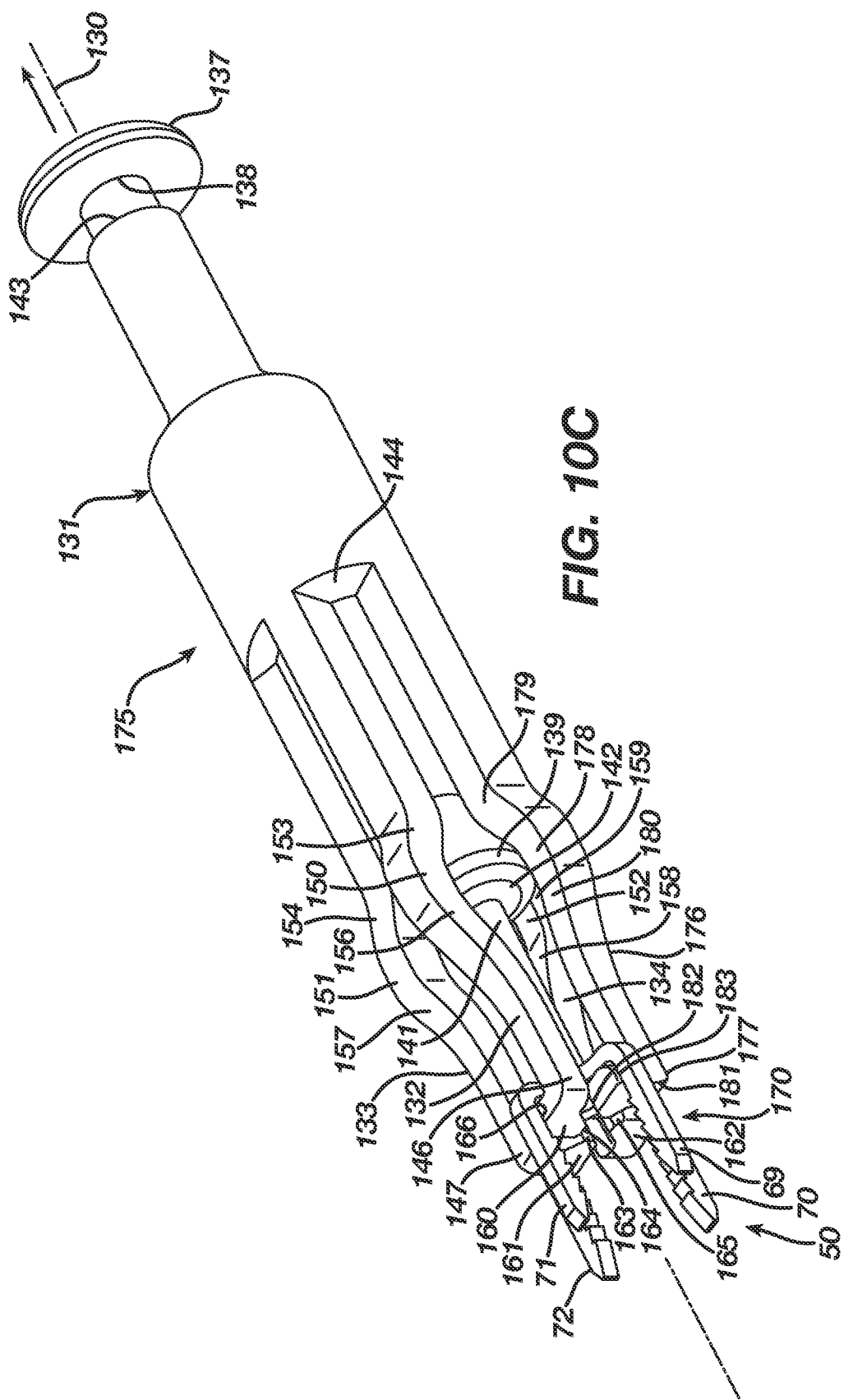
FIG. 10C is an isometric view illustrating a movement of the implant delivery device from the implant engagement position toward an implant release position in order to initiate a release of the radially compressive shape memory implant according to the second embodiment from the implant delivery device.
Figure 10D:
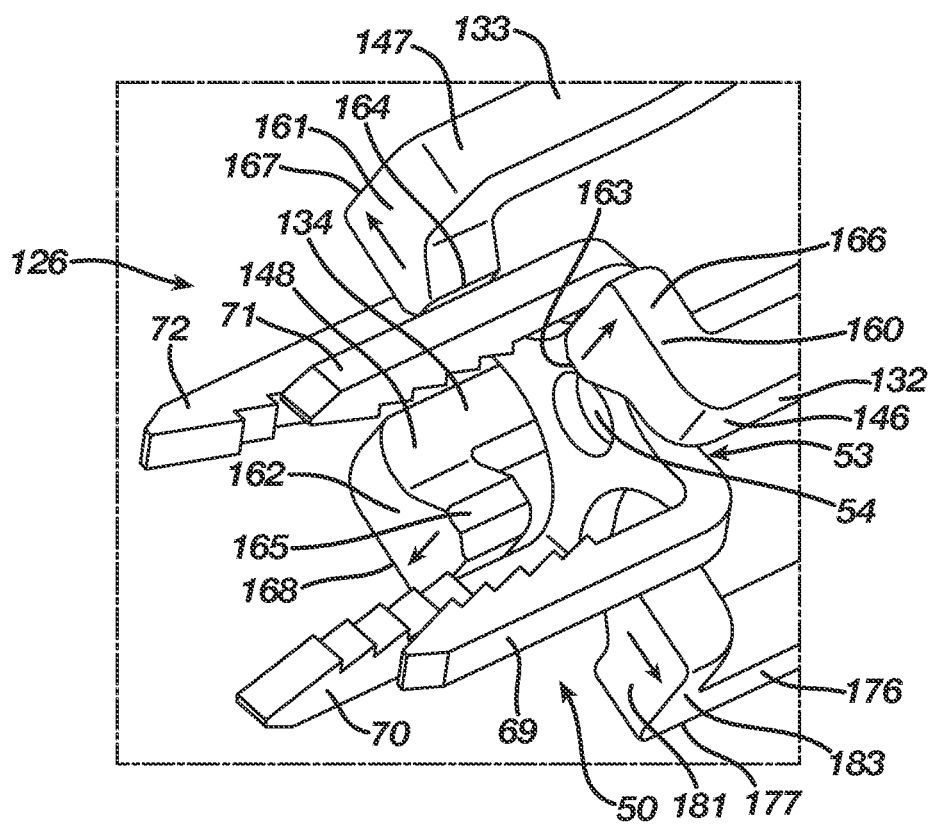
FIG. 10D is an isometric view illustrating the implant delivery device in the implant release position that releases the radially compressive shape memory implant according to the second embodiment from the implant delivery device.

The implant delivery device 175, when loaded with an implant 50 according to the second embodiment whereby the implant delivery device 175 in the implant engagement position 127 as illustrated in FIGS. 10A and 10B constrains the implant 50 in the insertion shape 52, delivers the implant 50 as follows. As illustrated in FIGS. 10C-10D, a retraction of the plunger 135 relative to the barrel 131 through a pulling on the head 137 moves the protrusion 139 from the second or lower ends 156-158 and 180 of the bends 150-152 and 178 into the expansion 159 defined by the bends 150-152 and 178. Concurrently, the rod 141 ceases its abutting relationship with the rod interfaces 163-165 and 182 of the abutments 160-162 and 181 while remaining disposed in the aperture 54 of the bridge 53 for the implant 50. Although the rod 141 stops supporting the abutments 160-162 and 181, the rod 141 remains in the aperture 54 of the bridge 53 in order to stabilize the implant 50 in the implant delivery device 175. With the protrusion 139 located in the expansion 159 defined by the bends 150-152 and 178 and the rod 141 retracted from the rod interfaces 163-165 and 182 of the abutments 160-162 and 181, the first, second, third, and fourth fingers 132-134 and 176 and the abutments 160-162 and 181 thereof collapse to the intermediate position 171, resulting in the abutments 160-162 and 181 at the implant interfaces 166-168 and 182, respectively, releasing the legs 69-72 of the implant 50. Once the abutments 160-162 and 181 at the implant interfaces 166-168 and 183, respectively, separate from the legs 69-72, the implant delivery device 175 rotates, which, in the illustrated embodiment of the implant delivery device 175, is clockwise, about the central vertical axis 130 until the abutments 160-162 and 181 at the implant interfaces 166-168 and 182, respectively, travel from a position in alignment with the legs 69-72 to an unaligned position remote therefrom. After the abutments 160-162 and 181 separate from the legs 69-72 and rotate to an unaligned position remote from the legs 69-72, a further retraction of the plunger 135 relative to the barrel 131 through a pulling on the head 137 moves the protrusion 139 from the expansion 159 defined by the bends 150-152 and 178 to a location adjacent and in abutment with the first or upper ends 153-155 and 179 of the bends 150-152 and 178. Concurrently, the rod 141 moves from the aperture 54 of the bridge 53 such that the rod 141 releases the bridge 53 and thus the implant 50 while also remaining separated from the rod interfaces 163-165 and 182 of the abutments 160-162 and 181. With the protrusion 139 located adjacent and in abutment with the first or upper ends 153-155 and 179 of the bends 150-152 and 178, the first, second, third, and fourth fingers 132-134 and 176 and thus the abutments 160-162 and 181 thereof expand to the disengaged position 169, resulting in the abutments 160-162 and 181 traveling away from the central vertical axis 130 to a position remote, respectively, from the bridge 53 of the implant 50 at the first, second, third, and fourth bridge segments 57-60 thereof. Once the abutments 160-162, respectively, separate to a position remote from the first, second, third, and fourth bridge segments 57-60 of the bridge 53, the implant delivery device 175 in the implant release position 126 releases the implant 50 through a movement of the implant delivery device 175 whereby the abutments 160-162 and 181, respectively, bypass the bridge 53 of the implant 50 at the first, second, third, and fourth bridge segments 57-60 thereof. The released implant 50, now unconstrained, attempts to transition from the insertion shape 52 to the natural shape 51 such that the implant 50 delivers the energy stored therein to bone, bones, or bone pieces in order to affix the bone, bones, or bone pieces through a radially compression thereof thereby promoting a healing of bone, bones, or bone pieces.

The implant delivery device 175, when residing in the implant release position 126 as illustrated in FIG. 10D, loads with an implant 50 according to the second embodiment placed in the insertion shape 52 as follows. The protrusion 139 in the implant release position 126 is located adjacent and in abutment with the first or upper ends 153-155 and 179 of the bends 150-152 and 178 while the rod 141 resides above the abutments 160-162 and 181 of the first, second, third, and fourth fingers 132-134 and 176. In accordance therewith, the abutments 160-162 and 181 begin separated and spaced apart from the central vertical axis 130 a distance sufficient for the abutments 160-162 and 181, respectively, to bypass the bridge 53 of the implant 50 at the first, second, third, and fourth bridge segments 57-60 thereof. The implant delivery device 175, which initially is placed above the bridge 53 of the implant 50 with the abutments 160-162 and 181, respectively, offset from the first, second, third, and fourth bridge segments 57-60 of the bridge 53, moves such that the abutments 160-162 and 181, respectively, bypass the first, second, third, and fourth bridge segments 57-60 until the abutments 160-162 and 181, respectively, reside below the first, second, third, and fourth bridge segments 57-60. An advancement of the plunger 135 relative to the barrel 131 through a pushing on the head 137 moves the protrusion 139 from the first or upper ends 153-155 and 179 of the bends 150-152 and 178 into the expansion 159 defined by the bends 150-152 and 178. Concurrently, the rod 141 progresses into the aperture 54 of the bridge 53 in order to stabilize the implant 50 in the implant delivery device 175. With the protrusion 139 located in the expansion 159 defined by the adjacent the bends 150-152 and 178, the first, second, third, and fourth fingers 132-134 and 176 and the abutments 160-162 and 181 thereof collapse to the intermediate position 171, resulting in the abutments 160-162 and 181 at the implant interfaces 166-168 and 183, respectively, moving to an unaligned position remote from the legs 69-72 of the implant 50 but interior thereto. Once the abutments 160-162 and 181 at the implant interfaces 166-168 and 183, respectively, reside in the unaligned position remote from the legs 69-72 of the implant 50 but interior thereto, the implant delivery device 175 rotates, which, in the illustrated embodiment of the implant delivery device 175, is counterclockwise, about the central vertical axis 130 until the abutments 160-162 and 181 at the implant interfaces 166-168 and 183, respectively, travel from the unaligned position remote from the legs 69-72 of the implant 50 but interior thereto to a position in alignment with the legs 69-72 but separated therefrom. After the abutments 160-162 and 181 rotate to the position in alignment with the legs 69-72 but separated therefrom, a further advancement of the plunger 135 relative to the barrel 131 through a pushing on the head 137 until the head 137 sits atop the barrel 131 at the first or top end 143 thereof moves the protrusion 139 from the expansion 159 defined by the bends 150-152 and 178 to a location adjacent and in abutment with the second or lower ends 156-158 and 180 of the bends 150-152 and 178. Concurrently, the rod 141 moves through the aperture 54 of the bridge 53 and into an abutting relationship with the rod interfaces 163-165 and 182 of the abutments 160-162 and 181. With the protrusion 139 located adjacent and in abutment with the second or lower ends 156-158 and 180 of the bends 150-152 and 178 and the rod 141 abutting the rod interfaces 163-165 and 182 of the abutments 160-162 and 181, the first, second, third, and fourth fingers 132-134 and 176 and thus the abutments 160-162 and 181 thereof expand to the engaged position 170, resulting in the abutments 160-162 and 181 traveling away from the central vertical axis 130 a distance sufficient for the abutments 160-162 and 181 at the implant interfaces 166-168 and 183, respectively, to abut the implant 50, and, in particular, the legs 69-72 thereof. The implant delivery device 125, now residing in the implant engagement position 127 with the rod 141 supporting the abutments 160-162, respectively, against the legs 69-72 at the implant interfaces 166-168 and 183, constrains the implant 50 in the insertion shape 52 whereby the implant 50 stores energy deliverable to bone, bones, or bone pieces. While the implant delivery device 175 loads with an implant 50 maintained in the insertion shape 52, one of ordinary skill in the art will recognize the implant delivery device 175 loads with an implant 50 in the natural shape 51 in that the expansion of the first, second, third, and fourth fingers 132-134 and 176 and thus the abutments 160-162 and 181 to the engaged position 170 results in the first, second, third, and fourth fingers 132-134 and 176 at the abutments 160-162 and 181 acting upon the transition sections 65-68 via the legs 69-72 such that the legs 69-72 move in order to facilitate a transition of the implant 50 from the natural shape 51 to the insertion shape 52.

Based upon the foregoing, the implant delivery device 175 differs from the implant delivery device 125 primarily in that the implant delivery device 175 includes the fourth finger 176. In accordance therewith, the implant delivery device 175 is substantially similar in design and operation relative to the implant delivery device 125, except that the implant delivery device 175 is engageable with an implant 50 having the four legs 69-72.

Figure 11A:
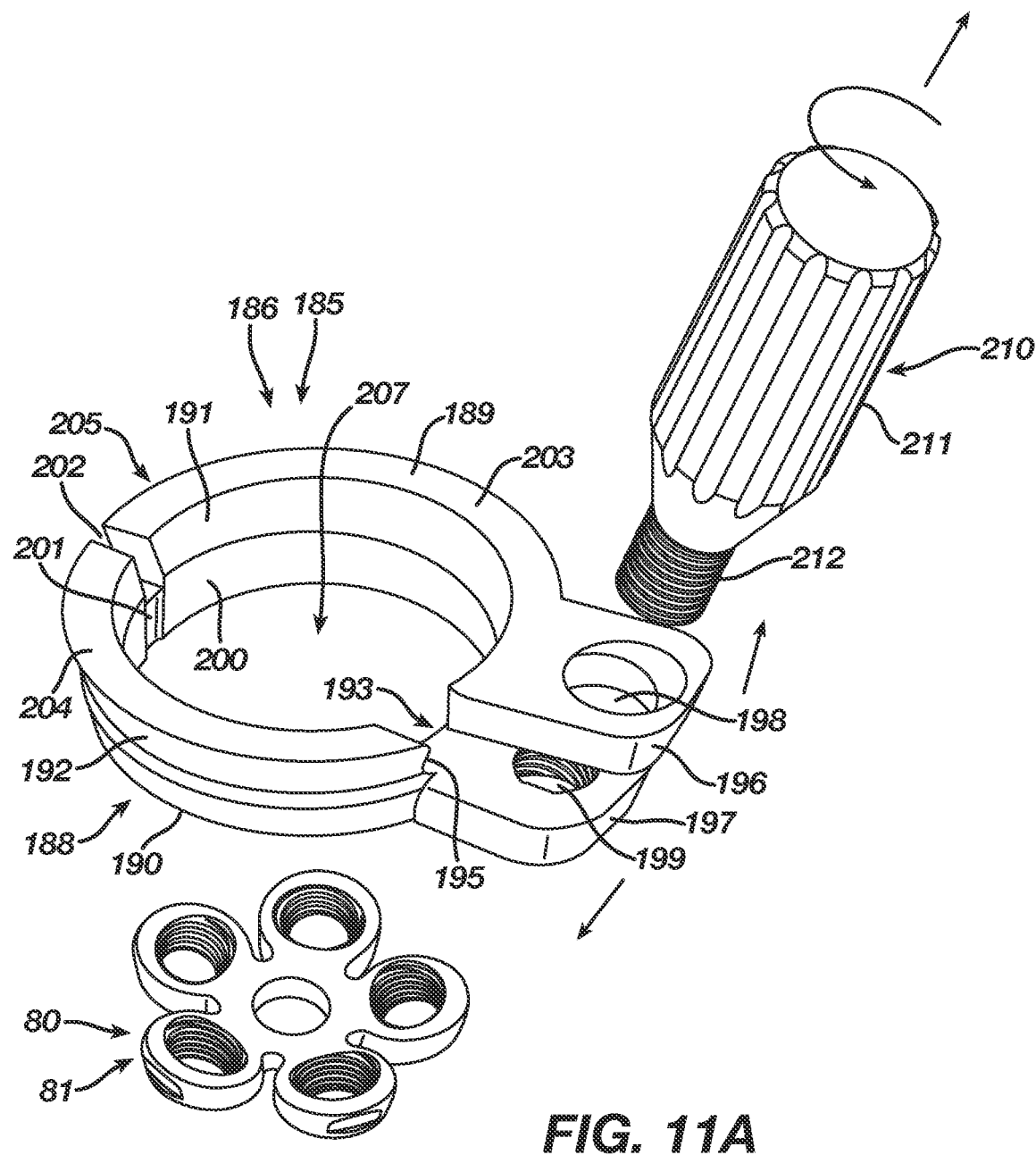
FIG. 11A is an isometric view illustrating the radially compressive shape memory implant according to the third embodiment residing in the natural shape and an implant delivery device thereof residing in an implant release position.
Figure 11B:
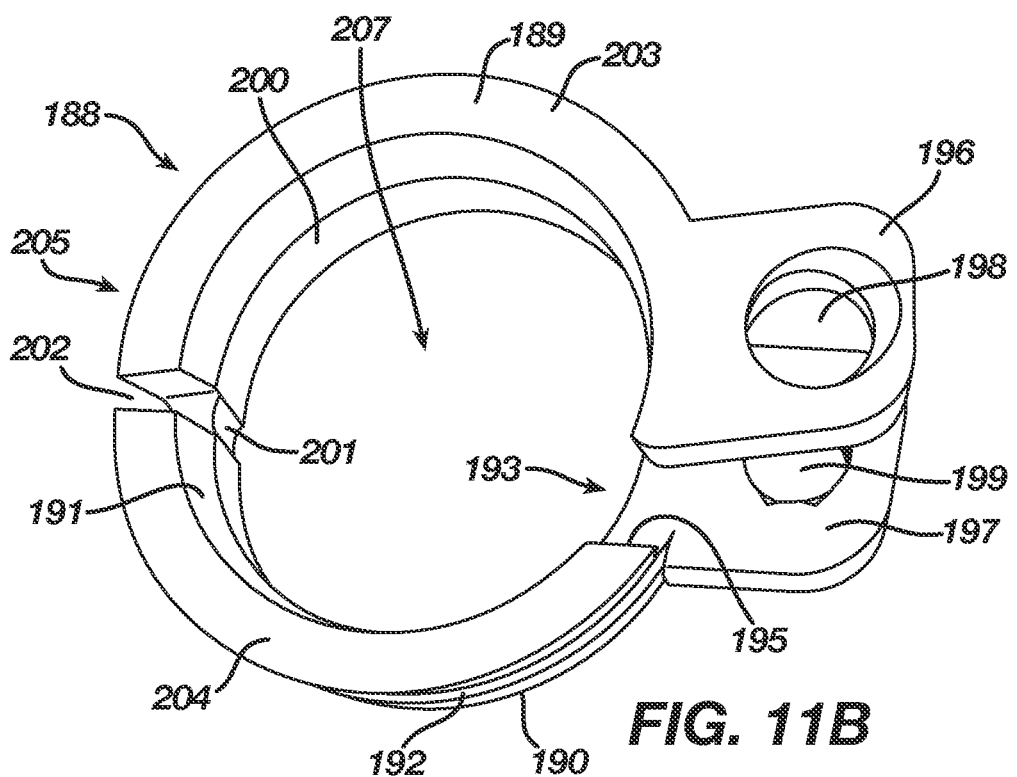
FIG. 11B is an isometric view illustrating an implant engagement ring of the implant delivery device when the implant delivery device resides in the implant release position.
Figure 11C:
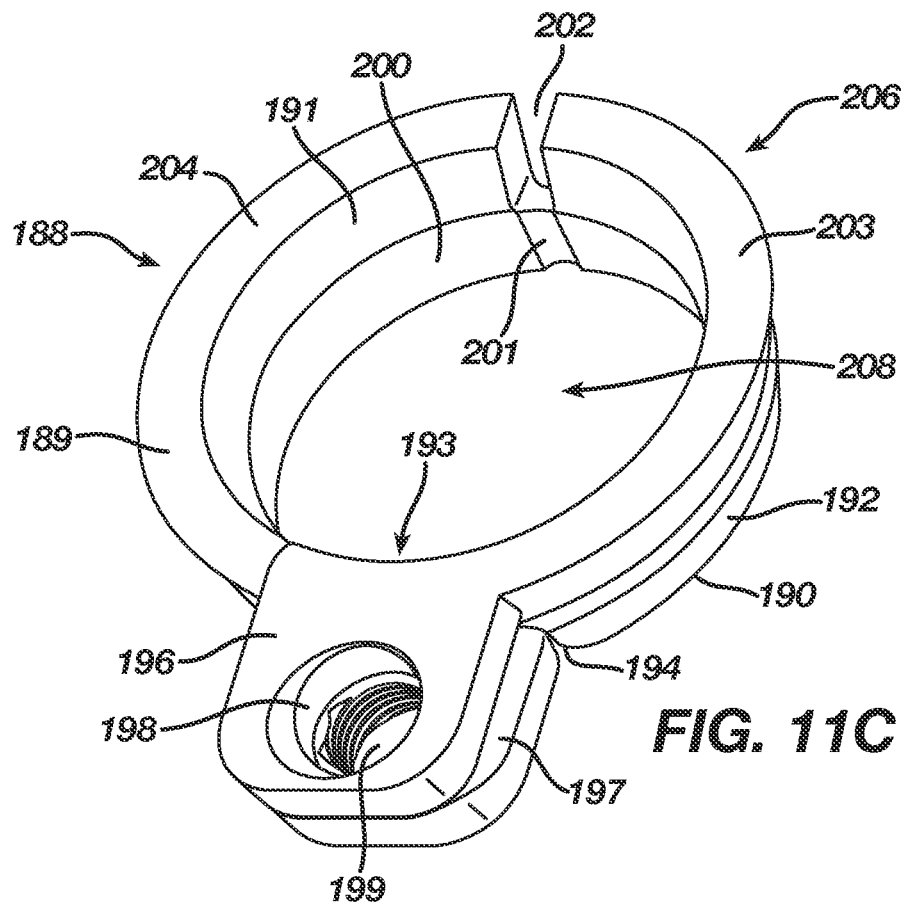
FIG. 11C is an isometric view illustrating the implant engagement ring of the implant delivery device when the implant delivery device resides in an implant engagement position.
Figure 11D:
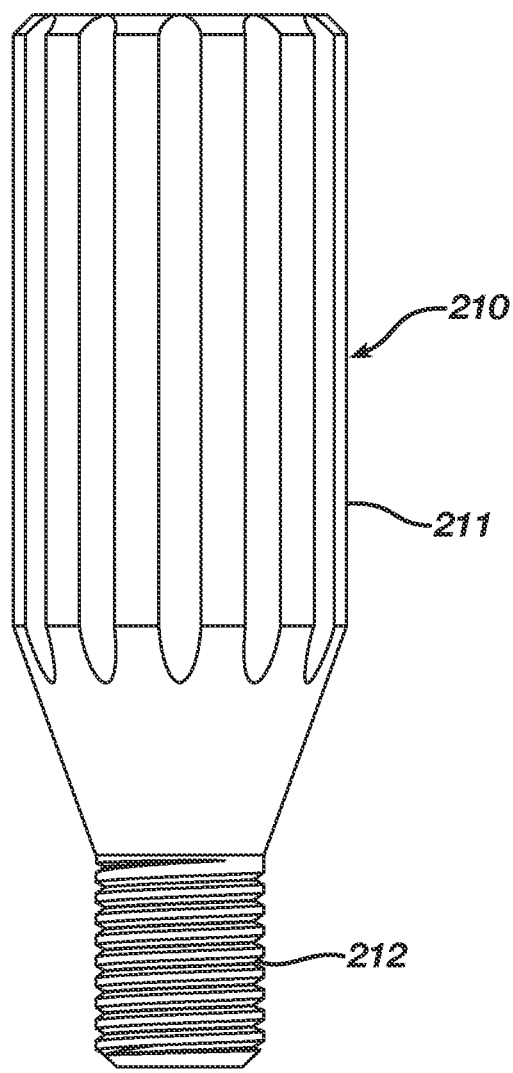
FIG. 11D is an isometric view illustrating a fastener of the implant delivery device.
Figure 12A:
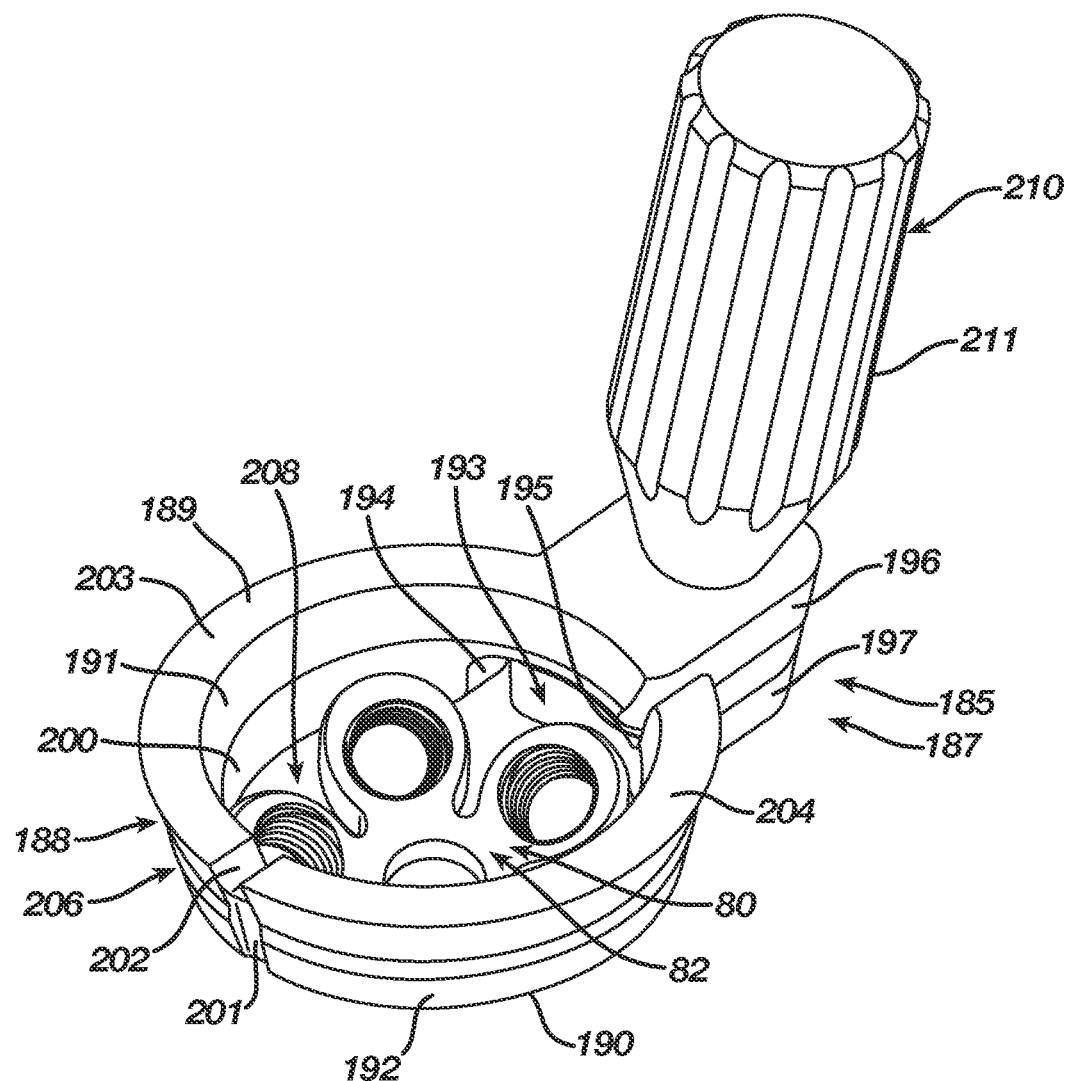
FIG. 12A is an isometric view illustrating the implant delivery device in the implant engagement position engaging the radially compressive shape memory implant according to the third embodiment.
Figure 12B:
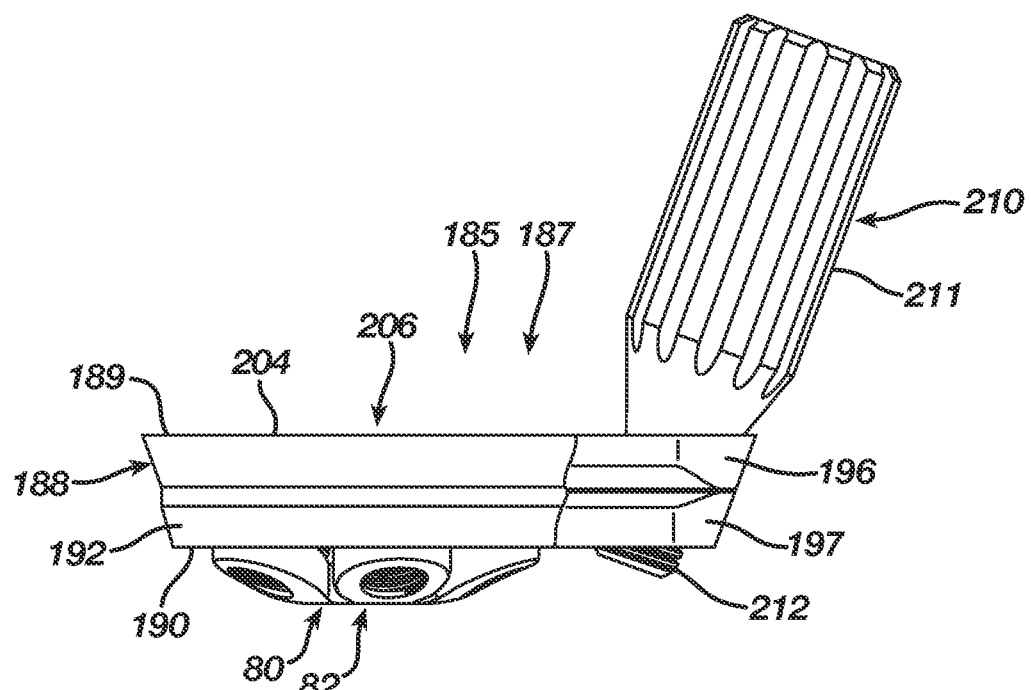
FIG. 12B is a side view illustrating the implant delivery device in the implant engagement position engaging the radially compressive shape memory implant according to the third embodiment.
Figure 12C:
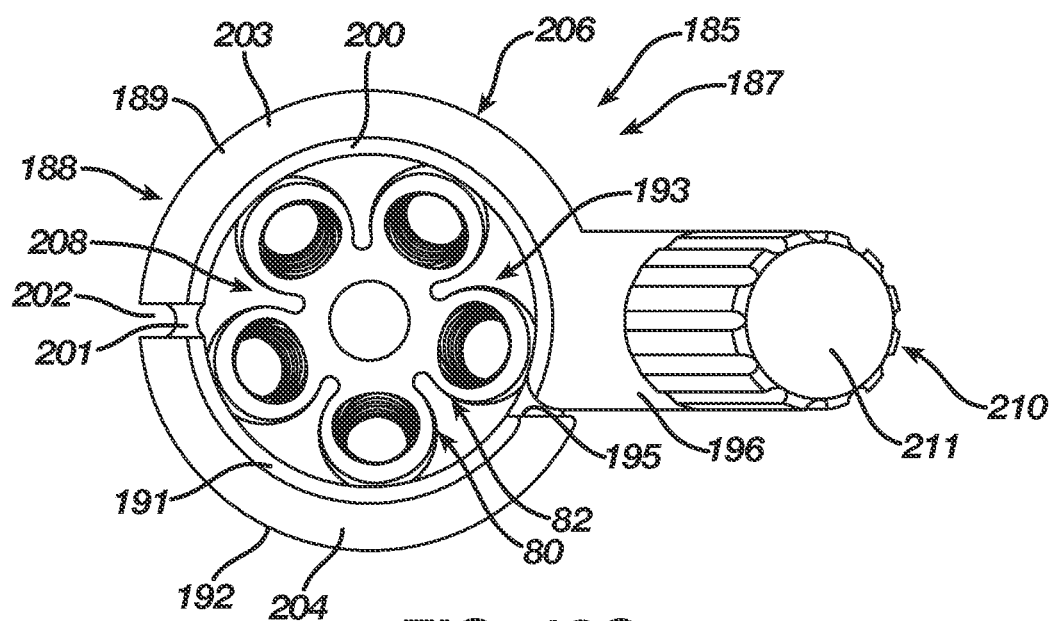
FIG. 12C is a top view illustrating the implant delivery device in the implant engagement position engaging the radially compressive shape memory implant according to the third embodiment.

FIGS. 11A-12C illustrate an implant delivery device 185 configured to engage an implant 80 according to the third embodiment and constrain the implant 80 in its insertion shape 82 such that the implant 80 may be implanted in bone, bones, or bone pieces during a surgical operation. The implant delivery device 185 resides in either an implant release position 186 as illustrated in FIG. 11A or an implant engagement position 187 as illustrated in FIGS. 12A-12C and is movable therebetween. The implant delivery device 185 when residing in the implant release position 186 releases the implant 80 whereby the implant 80 disengages from the implant delivery device 185 without obstruction. Conversely, the implant delivery device 185 when residing in the implant engagement position 187 engages the implant 80 and maintains the implant 80 constrained in the insertion shape 82. In addition, the implant delivery device 185 allows a surgeon to manipulate the implant 80 and implant the implant 80 into bone, bones, or bone pieces requiring fixation.

The implant delivery device 185 includes an implant holding ring 188 with a top 189, a bottom 190, an inner wall 191, and an outer wall 192. The implant holding ring 188 includes a split 193 whereby the implant holding ring 188 terminates in a first end 194 and a second end 195. The implant holding ring 188 includes a first or upper projection 196 with an aperture 198 therethrough extending from the first end 194 of the implant holding ring 188 at the top 189 thereof into the split 193 as well as away from the outer wall 192. The implant holding ring 188 includes a second or lower projection 197 with an aperture 199 therethrough, preferably threaded, extending from the second end 195 of the implant holding ring 188 at the bottom 190 thereof into the split 193 as well as away from the outer wall 192. The positioning of the first or upper projection 196 at the top 189 and the second or lower projection 197 at the bottom 190 permits a vertical alignment of the apertures 198 and 199. The implant holding ring 188 in the inner wall 191 at the bottom 190 includes an implant holding surface 200 configured to engage the first, second, third, fourth, and fifth bridge segments 87-91 of the implant 80 at their respective ends 92-96. More particularly, the implant holding surface 200 engages the interlocks 107 such that the implant holding surface 200 abuts the engagement interfaces 108 while the bottom 190 abuts the detents 109. The implant holding ring 188 includes a pivot member 201 across from the split 193 at the bottom 190 of the implant holding ring 188. The pivot member 201, which is produced by a slot 202 created in the implant holding ring 188 at the top 189 thereof, divides the implant holding ring 188 into first and second ring sections 203 and 204.

The implant holding ring 188 and the pivot member 201 in particular preferably are manufactured from a resilient metal or plastic material that allows flexing of the implant holding ring 188 about the pivot member 201 in order to facilitate an expansion and a contraction of the implant holding ring 188. The implant holding ring 188 includes an open position 205 as illustrated in FIG. 11B where the implant holding ring 188 is expanded to a first diameter 207 dimensionally larger than the implant 80. When the implant holding ring 188 resides in the open position 205, the first end 194 and the second end 195 and thus the first or upper projection 196 and the second or lower projection 197 are spaced apart resulting in a lack of vertical alignment between the apertures 198 and 199. As a consequence, the implant holding ring 188 due to the first diameter 207 releases the implant 80 whereby the implant 80 disengages from the implant holding ring 188 without obstruction. Conversely, the implant holding ring 188 includes a closed position 206 as illustrated in FIG. 11C where the implant holding ring 188 is contracted to a second diameter 208 that is less than the first diameter 207 while being dimensionally substantially identical to the implant 80. When the implant holding ring 188 resides in the closed position 206, the first end 194 is located adjacent the second end 195 such that the first or upper projection 196 is position atop the second or lower projection 197 resulting in a vertical alignment between the apertures 198 and 199. As a consequence, the implant holding ring 188 due to the second diameter 208 engages the implant 80 and maintains the implant 80 constrained in the insertion shape 82.

The implant delivery device 185 as illustrated in FIG. 11D includes a fastener 210 engageable with the implant holding ring 188 in order to retain the implant holding ring 188 in the closed position 206 such that the implant delivery device 185 resides in the implant engagement position 187. When the implant holding ring 188 resides in the closed position 206, the fastener 210 inserts through the vertically aligned apertures 198 and 199 and secures with at least the aperture 199 in order to maintain the implant holding ring 188 locked in the closed position 206. The fastener 210 preferably includes a handle 211 terminating in threads 212 configured to engage threads in at least the aperture 199. The handle 211 permits a surgeon to grasp the implant delivery device 185 and through a manipulation thereof to implant the implant 80 into bone, bones, or bone pieces requiring fixation.

The implant delivery device 185, when loaded with an implant 80 according to the third embodiment whereby the implant delivery device 185 in the implant engagement position 187 as illustrated in FIGS. 12A-12C constrains the implant 80 in the insertion shape 82, delivers the implant 80 as follows. A rotation of the fastener 210 via the handle 211 relative to the first or upper projection 196 and the second or lower projection 197, which, in the illustrated embodiment of the implant delivery device 185, is counterclockwise, removes the fastener 210 at the threads 212 from the apertures 198 and 199. With the fastener 210 removed from the first or upper projection 196 and the second or lower projection 197, the implant holding ring 188 expands about the pivot member 201 from the closed position 206 to the open position 205 either naturally due to its resilient material or through a physical manipulation thereof whereby the implant delivery device 185 transitions from the implant engagement position 187 to the implant release position 186. The expansion of the implant holding ring 188 from the closed position 206 to the open position 205 separates and spaces apart the first end 194 from the second end 195 and thus the first or upper projection 196 from the second or lower projection 197 such that the implant holding ring 188 opens in a movement from the second diameter 208 to the first diameter 207. The implant holding ring 188 when opened to the first diameter 207 whereby the implant delivery device 185 resides in the implant release position 186 disengages at the implant holding surface 200 from the interlocks 107 of the implant 80 in order to release the implant 80 from the implant holding ring 188. The released implant 80, now unconstrained, attempts to transition from the insertion shape 82 to the natural shape 81 such that the implant 80 delivers the energy stored therein to bone, bones, or bone pieces in order to affix the bone, bones, or bone pieces through a radially compression thereof thereby promoting a healing of bone, bones, or bone pieces.

The implant delivery device 185, when residing in the implant release position 186 as illustrated in FIG. 11A, loads with an implant 80 according to the third embodiment placed in the insertion shape 82 as follows. The implant holding ring 188, which begins in the open position 205 where the first or upper projection 196 and the second or lower projection 197 and thus the apertures 198 and 199 are misaligned, is placed about an implant 80 in the insertion shape 82 such that the interlocks 107 of the implant 80 align with the implant holding surface 200 disposed along the inner wall 191 of the implant holding ring 188. With the implant holding ring 188 placed about the implant 80, the implant holding ring 188 is contracted about the pivot member 201 from the open position 205 to the closed position 206 through a physical manipulation of the implant holding ring 188. The contraction of the implant holding ring 188 from the open position 205 to the closed position 206 closes the implant holding ring 188 in a movement from the first diameter 207 to the second diameter 208 that vertically aligns the first or upper projection 196 with the second or lower projection 197 and thus the aperture 198 with the aperture 199. The implant holding ring 188 when closed to the second diameter 208 engages the interlocks 107 of the implant 80 at the implant holding surface 200 in order to retain the implant 80 therein. After retention of the implant 80 in the implant holding ring 188, the fastener 210 inserts into the vertically aligned apertures 198 and 199 whereby a rotation of the fastener 210 via the handle 211, which, in the illustrated embodiment of the implant delivery device 185, is clockwise, introduces the fastener 210 at the threads 212 into the apertures 198 and 199 for engagement with at least corresponding threads of the aperture 199. The implant delivery device 185, now residing in the implant engagement position 187 with the fastener 210 retaining the implant holding ring 188 in the closed position 206 and the implant holding ring 188 at the implant holding surface 200 grasping the implant 80 at the interlocks 107, constrains the implant 80 in the insertion shape 82 whereby the implant 80 stores energy deliverable to bone, bones, or bone pieces. While the implant delivery device 185 loads with an implant 80 maintained in the insertion shape 82, one of ordinary skill in the art will recognize the implant delivery device 185 loads with an implant 80 in the natural shape 81 in that the contraction of the implant holding ring 188 to the closed position 206 results in the implant holding ring 188 at the implant holding surface 200 acting upon the transition sections 102-106 via the first, second, third, fourth, and fifth bridge segments 87-91 at their respective ends 92-96 such that the first, second, third, fourth, and fifth bridge segments 87-91 move in order to facilitate a transition of the implant 80 from the natural shape 81 to the insertion shape 82.

Figure 13A:
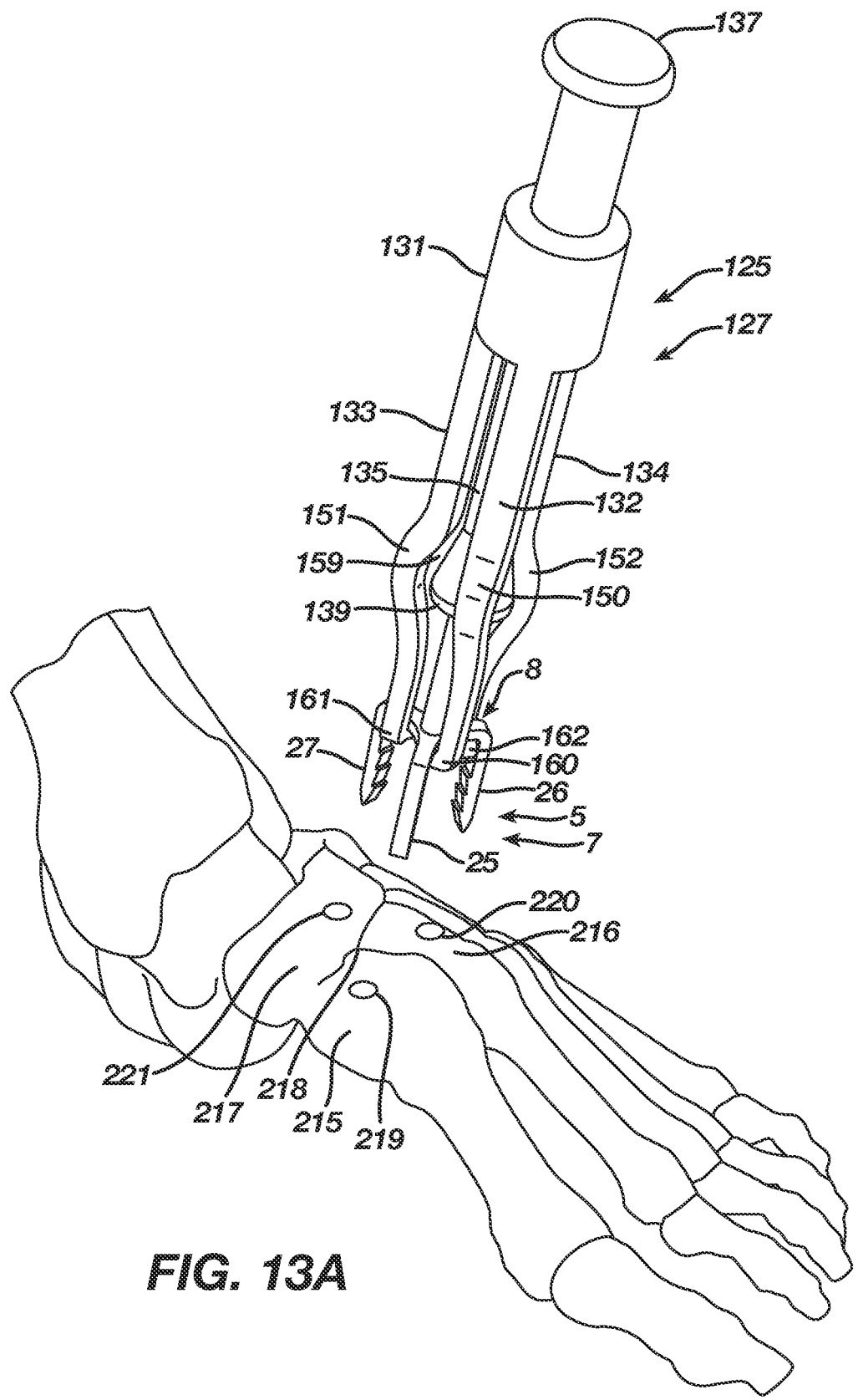
FIGS. 13A-13C are isometric views illustrating use of the radially compressive shape memory implant according to the first embodiment and the implant delivery device associated therewith to affix bone, bones, or bone pieces.

FIG. 13A illustrates the implant delivery device 125 with the implant 5 of the first embodiment loaded thereon in an orthopedic fixation system whereby the implant delivery device 125 in the implant engagement position 127 retains the implant 5 in its insertion shape 7 such that the implant 5 is ready for implantation into bone, bones, or bone pieces, and, in particular, into a first bone 215, a second bone 216, and a third bone 217, which are presented herein as an example. A surgeon as illustrated in FIG. 13A aligns the first bone 215, the second bone 216, and the third bone 217 at a fusion zone 218 in an orientation that promotes fixation of the first bone 215, the second bone 216, and the third bone 217 and a proper healing thereof. The surgeon, if necessary, temporarily affixes the first, second, and third bones 215-217, and then drills a first hole 219 in the first bone 215, a second hole 220 in the second bone 218, and a third hole 221 in the third bone 217. The first, second, and third holes 219-221 are drilled at spacings and locations desired for insertion of the leg 25 of the implant 5 into the first bone 215, the leg 26 of the implant 5 into the second bone 216, and the leg 27 of the implant 5 into the third bone 217 with the bridge 8 of the implant 5 spanning the fusion zone 218 when the implant 5 resides in its insertion shape 7. While not required, the surgeon may create grooves in the first, second, and third bones 215-217 that facilitate a more flush seating of the bridge 8 for the implant 5 relative to the first, second, and third bones 215-217. The surgeon next utilizes the implant delivery device 125 to position the tip 28 of the leg 25 for the implant 5 adjacent the first hole 219, the tip 29 of the leg 26 for the implant 5 adjacent the second hole 220, and the tip 30 of the leg 27 for the implant 5 adjacent the third hole 221.

Figure 13B:
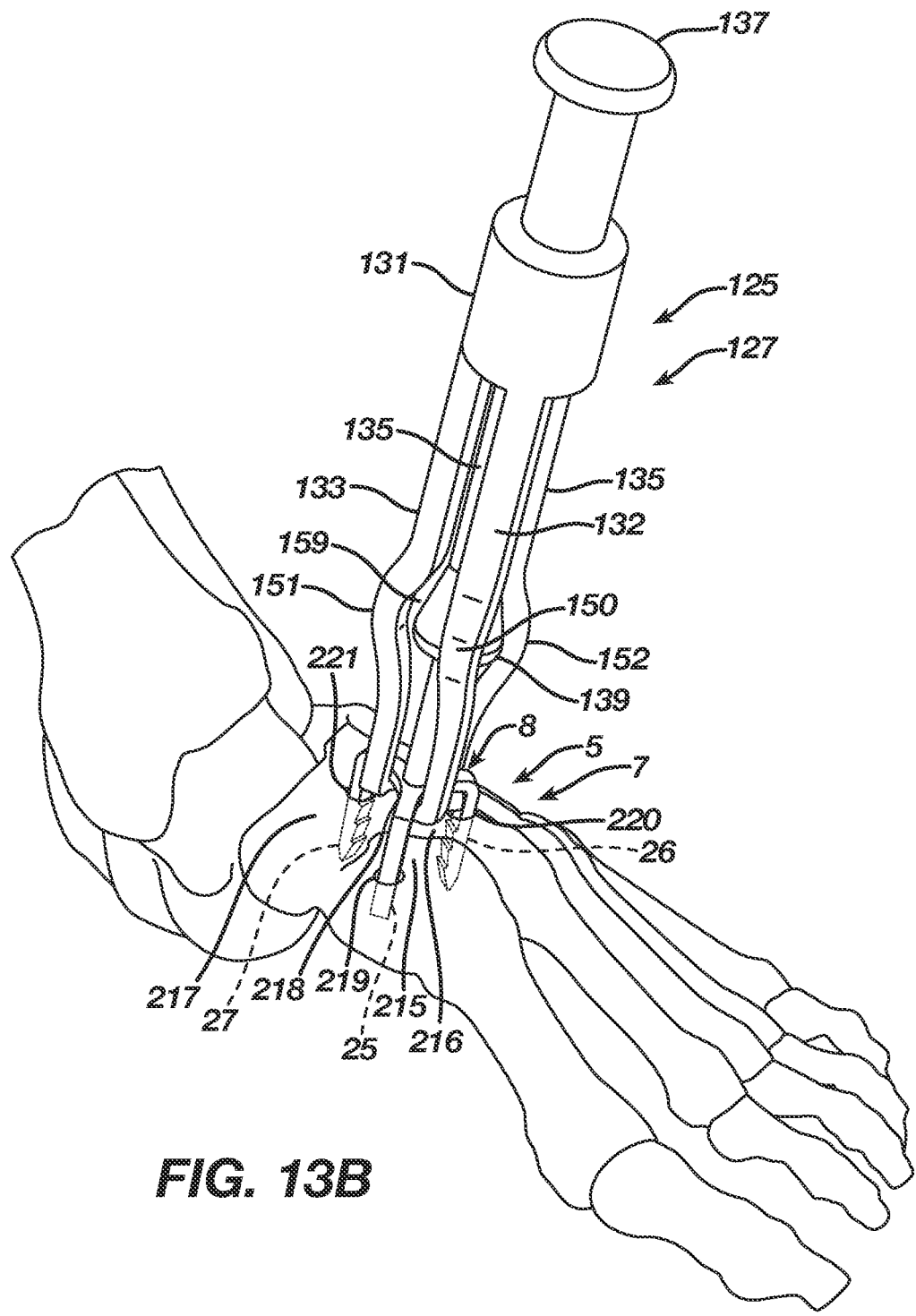

The surgeon as illustrated in FIG. 13B maneuvers the implant 5 using the implant delivery device 125 such that the legs 25-27 respectively enter the first, second, and third holes 219-221. The surgeon further manipulates the implant delivery device 125 to insert the legs 23-26 respectively into the first, second, and third holes 219-221 as far as possible while leaving sufficient space for the implant delivery device 125 to release the implant 5. Upon positioning the legs 25-27 respectively in the first, second, and third holes 219-221, the surgeon transitions the implant delivery device 125 from the implant engagement position 127 to the implant release position 126 as previously described with reference to FIGS. 9A-9G. The surgeon transitions the implant delivery device 125 from the implant engagement position 127 to the transitional position 128 by pulling on the head 137 to retract the plunger 135 relative to the barrel 131. The protrusion 139 accordingly moves from the second or lower ends 156-158 of the bends 150-152 into the expansion 159 defined by the bends 150-152. Concurrently, the rod 141 ceases its abutting relationship with the rod interfaces 163-165 of the abutments 160-162 while remaining disposed in the aperture 9 of the bridge 8 for the implant 5. With the protrusion 139 located in the expansion 159 defined by the bends 150-152 and the rod 141 retracted from the rod interfaces 163-165 of the abutments 160-162, the first, second, and third fingers 132-134 and the abutments 160-162 thereof collapse to the intermediate position 171, resulting in the abutments 160-162 at the implant interfaces 166-168, respectively, releasing the legs 25-27 of the implant 5. Once the abutments 160-162 at the implant interfaces 166-168, respectively, separate from the legs 25-27, the surgeon rotates the implant delivery device 125 about the central vertical axis 130 until the abutments 160-162 at the implant interfaces 166-168, respectively, travel from a position in alignment with the legs 25-27 to an unaligned position remote therefrom. After the abutments 160-162 separate from the legs 25-27 and rotate to an unaligned position remote from the legs 25-27, the surgeon further retracts the plunger 135 relative to the barrel 131 by pulling on the head 137. The protrusion 139 accordingly moves from the expansion 159 defined by the bends 150-152 to a location adjacent and in abutment with the first or upper ends 153-155 of the bends 150-152. Concurrently, the rod 141 moves from the aperture 9 of the bridge 8 such that the rod 141 releases the bridge 8 and thus the implant 5 while also remaining separated from the implant interfaces 166-168 of the abutments 160-162. With the protrusion 139 located adjacent and in abutment with the first or upper ends 153-155 of the bends 150-152, the first, second, and third fingers 132-134 and thus the abutments 160-162 thereof expand to the disengaged position 169, resulting in a complete release of the implant 5 as the abutments 160-162 travel away from the central vertical axis 130 to a position remote, respectively, from the bridge 8 of the implant 5 at the first, second, and third bridge segments 12-14 thereof. Once the abutments 160-162, respectively, separate to a position remote from the first, second, and third bridge segments 12-14 of the bridge 8, the surgeon, now that the implant delivery device 125 resides in the implant release position 126, withdraws the implant delivery device 125 from the implant 5 by moving the implant delivery device 125 such that the abutments 160-162, respectively, bypass the bridge 8 of the implant 5 at the first, second, and third bridge segments 12-14 thereof. While an insertion of the implant 5 typically includes pre-drilling of the first, second, and third holes 219-221, the surgeon may use implant delivery device 125 to impact the legs 25-27 respectively into the first, second, and third bones 215-217 at a desired location.

Figure 13C:
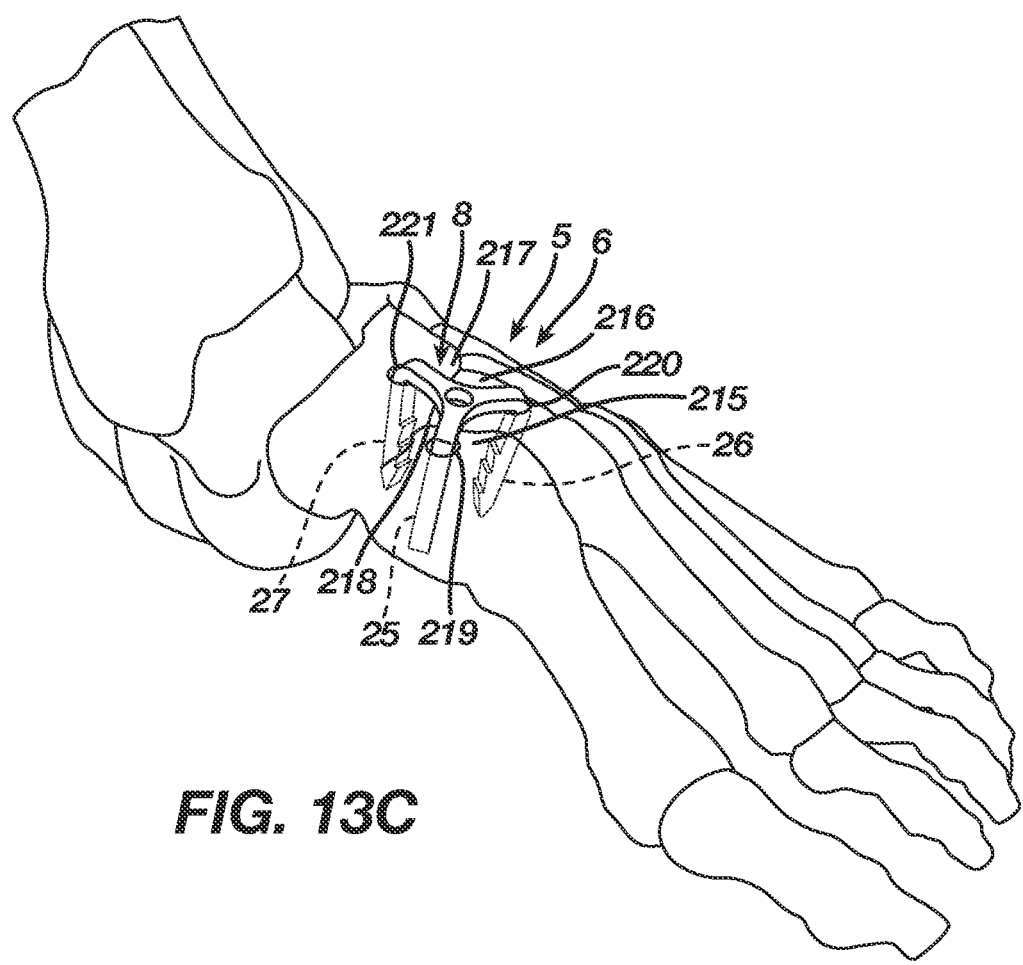

After withdrawing the implant delivery device 125 from the implant 5, the surgeon tamps the implant 5 at the bridge 8 until the implant 5 at the bridge 8 seats completely flush atop the first, second, and third bones 215-217 with the bridge 8 spanning the fusion zone 218. With the legs 25-27 respectively fully inserted into the first, second, and third bones 215-217 via the first, second, and third holes 219-221 and the bridge 8 seated completely flush atop the first, second, and third bones 215-217 across the fusion zone 218 as illustrated in FIG. 13C, the implant 5, due to its superelastic or temperature dependent properties, delivers the energy stored in the transition sections 18-20 such that the bridge 8 attempts to transition from its insertion form to its natural form, resulting in the legs 25-27 attempting to move from their insertion position to their natural position, whereby the implant 5 affixes the first, second, and third bones 215-217 through an application of a radially compressive force to the fixation zone 218. One of ordinary skill in the art will recognize that a method of implanting an implant 50 of the second embodiment involving the implant delivery device 175 with the implant 50 loaded thereon in an orthopedic fixation system would be substantially, completely similar to the above-described method of implanting an implant 5 using the implant delivery device 125.

Figure 14A:
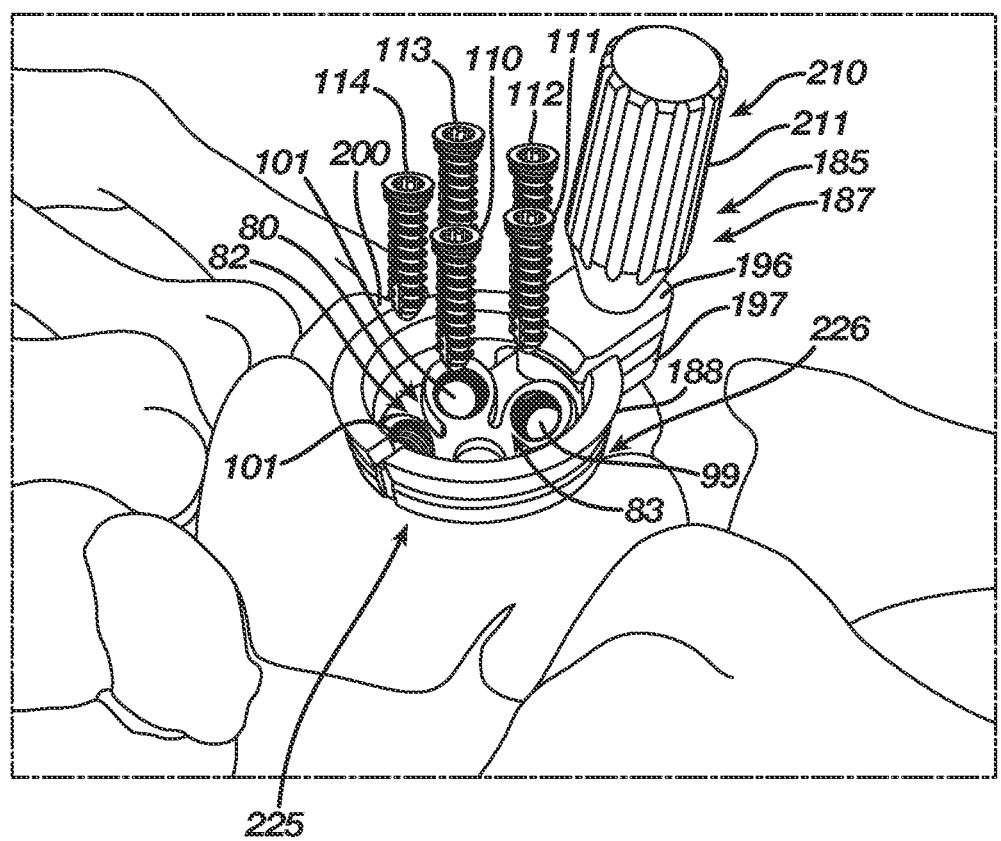
FIGS. 14A-14C are isometric views illustrating use of the radially compressive shape memory implant according to the third embodiment and the implant delivery device associated therewith to affix bone, bones, or bone pieces.

FIG. 14A illustrates the implant delivery device 185 with the implant 80 of the third embodiment loaded thereon in an orthopedic fixation system whereby the implant delivery device 185 in the implant engagement position 187 retains the implant 80 in its insertion shape 82 such that the implant 80 is ready for implantation into bone, bones, or bone pieces, and, in particular, into a plurality of bones referred to generally as bones 225, which are presented herein as an example. A surgeon as illustrated in FIG. 14A aligns the bones 225 at a fusion zone 226 in an orientation that promotes fixation of the bones 225 and a proper healing thereof. The surgeon, if necessary, temporarily affixes the bones 225, and then, the surgeon, utilizing the implant delivery device 185 via the fastener 211, places the implant 80 atop the bones 225 with the bridge 83 of the implant 80 spanning the fusion zone 226 when the implant 80 resides in its insertion shape 82.

Figure 14B:
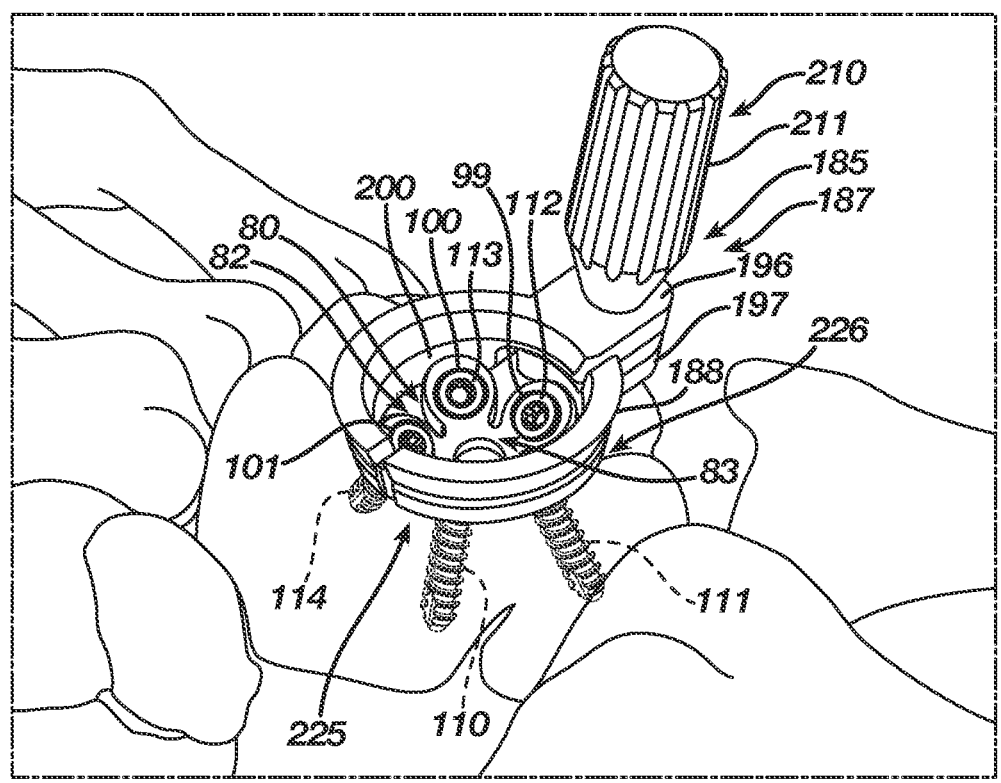

The surgeon as illustrated in FIG. 14B next inserts the screws 110-114 respectively through the openings 97-101 respectively of the first, second, third, fourth, and fifth bridge segments 87-91 of the bridge 83. The surgeon inserts the screws 110-114 into the bones 225 until the screws 110-114 fully seat within the respective first, second, third, fourth, and fifth bridge segments 87-91. The surgeon directly inserts the screws 110-114 into the bones 225 when the screws 110-114 are self-tapping bone screws. Alternatively, the surgeon may drill holes in the bones 225, which may include use of the openings 97-101 of the bridge 83 as a guide, when the screws 110-114 are not self-tapping.

After securing the implant 80 atop the bones 225 using the screws 110-114, the surgeon transitions the implant delivery device 185 from the implant engagement position 187 to the implant release position 186 as previously described with reference to FIGS. 11A-12C. The surgeon rotates the fastener 210 via the handle 211 relative to the first or upper projection 196 and the second or lower projection 197 until the fastener 210 at the threads 212 is removed from the apertures 198 and 199. With the fastener 210 removed from the first or upper projection 196 and the second or lower projection 197, the surgeon expands the implant holding ring 188 about the pivot member 201 from the closed position 206 to the open position 205 such that the implant delivery device 185 transitions from the implant engagement position 187 to the implant release position 186. The implant holding ring 188 accordingly disengages at the implant holding surface 200 from the interlocks 107 of the implant 80 thereby facilitating a release of the implant 80 from the implant holding ring 188. Upon release of the implant 80 from the implant holding ring 188, the surgeon withdraws the implant delivery device 185 from the implant 80.

Figure 14C:
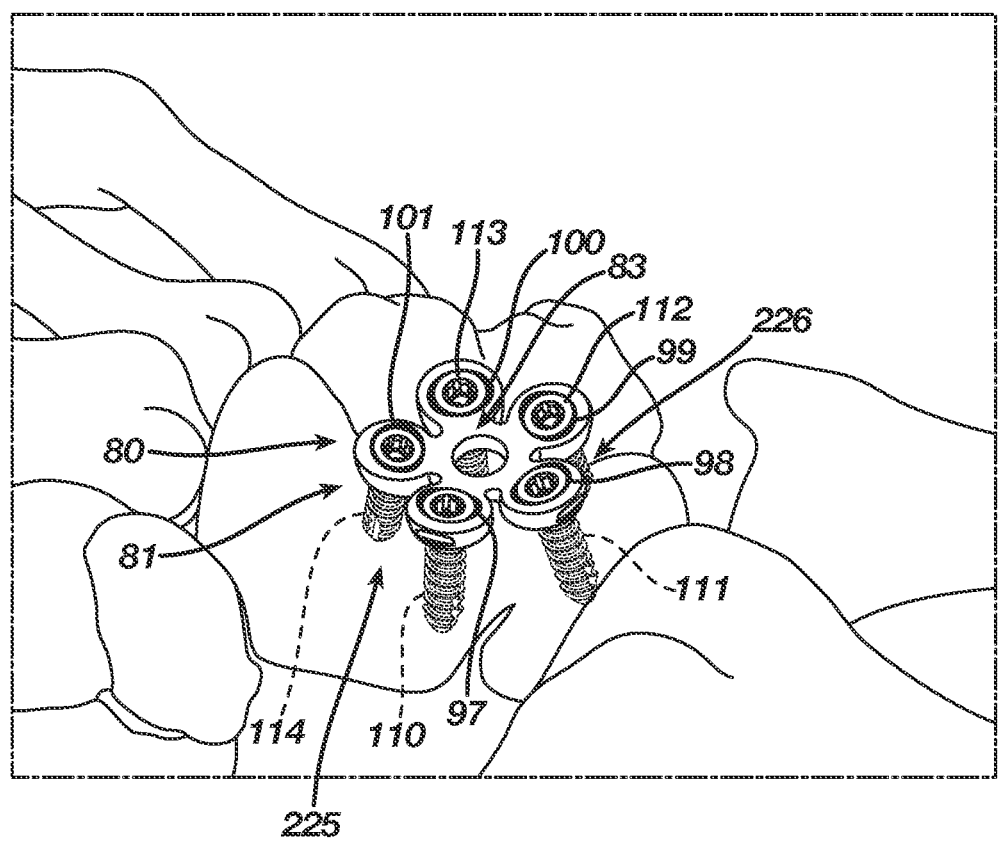

With the screws 110-114 fully inserted into the bones 225 and the bridge 83 seated atop the bones 225 across the fusion zone 226 as illustrated in FIG. 14C, the implant 80, due to its superelastic or temperature dependent properties, delivers the energy stored in the transition sections 102-106 such that the bridge 83 attempts to transition from its insertion form to its natural form, resulting in the screws 110-114 attempting to move from their insertion position to their natural position, whereby the implant 80 affixes the bones 225 through an application of a radially compressive force to the fixation zone 226.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. A radially compressive implant, comprising:
 a bridge including a central vertical axis, the bridge, comprising:
  a center section,
  a first bridge segment extending from the center section to an end thereof, the first bridge segment including an opening adjacent the end thereof,
  a second bridge segment extending from the center section to an end thereof, the second bridge segment including an opening adjacent the end thereof,
  a third bridge segment extending from the center section to an end thereof, the third bridge segment including an opening adjacent the end thereof, whereby the first bridge segment, the second bridge segment, and the third bridge segment at the ends thereof each define an interlock adapted to facilitate engagement of the implant with an implant delivery device,
  a first transition section located in the first bridge segment between the center section and the opening of the first bridge segment,
  a second transition section located in the second bridge segment between the center section and the opening of the second bridge segment, and
  a third transition section located in the third bridge segment between the center section and the opening of the third bridge segment;
 a first fixation member inserted through the opening of the first bridge segment at the end thereof;
 a second fixation member inserted through the opening of the second bridge segment at the end thereof;
 a third fixation member inserted through the opening of the third bridge segment at the end thereof; and
 the implant being transitionable between a natural shape and an insertion shape, wherein:
  a transition of the implant from the natural shape to the insertion shape includes the first transition section, the second transition section, and the third transition section being deformable to store energy whereby the first transition section, the second transition section, and the third transition section move the bridge from a natural form to an insertion form, further whereby the first transition section moves the first fixation member, the second transition section moves the second fixation member, and the third transition section moves the third fixation member away from the central axis such that the first fixation member, the second fixation member, and the third fixation member diverge relative to the central axis as the first fixation member, the second fixation member, and the third fixation member progress from a natural position to an insertion position thereby facilitating the implant storing energy deliverable radially relative to the central vertical axis, and a transition of the implant from the insertion shape toward the natural shape includes the first transition section, the second transition section, and the third transition section delivering the energy stored therein whereby the first transition section, the second transition section, and the third transition section move the bridge from the insertion form toward the natural form, further whereby the first transition section moves the first fixation member, the second transition section moves the second fixation member, and the third transition section moves the third fixation member toward the central axis such that the first fixation member, the second fixation member, and the third fixation member converge relative to the central axis as the first fixation member, the second fixation member, and the third fixation member progress from the insertion position toward the natural position thereby facilitating the implant delivering the energy stored therein radially relative to the central vertical axis.

2. The radially compressive implant of claim 1, wherein the first bridge segment, the second bridge segment, and the third bridge segment radially extend from the center section and are spaced symmetrically about the central vertical axis of the implant.

3. The radially compressive implant of claim 1, wherein the first bridge segment, the second bridge segment, and the third bridge segment are dimensionally identical.

4. The radially compressive implant of claim 1, wherein the first fixation member, the second fixation member, and the third fixation member are spaced symmetrically about the central vertical axis of the implant in both the natural position and the insertion position.

5. The radially compressive implant of claim 1, wherein:
the first fixation member, the second fixation member, and the third fixation member in the natural position reside from the central vertical axis at a first distance; and
the first fixation member, the second fixation member, and the third fixation member in the insertion position reside from the central vertical axis at a second distance that is greater than the first distance.

6. The radially compressive implant of claim 1, wherein the bridge defines an aperture at the central vertical axis of the implant.

7. The radially compressive implant of claim 1, wherein:
the first fixation member, the second fixation member, and the third fixation member in the natural position reside from the central vertical axis at a first angle measured from a plane perpendicular to the central vertical axis; and
the first fixation member, the second fixation member, and the third fixation member in the insertion position reside from the central vertical axis at a second angle measured from a plane perpendicular to the central vertical axis that is greater than the first angle.

8. The radially compressive implant of claim 1, wherein:
the first fixation member comprises a first screw inserted through the opening of the first bridge segment at the end thereof;
the second fixation member comprises a second screw inserted through the opening of the second bridge segment at the end thereof; and
the third fixation member comprises a third screw inserted through the opening of the third bridge segment at the end thereof.

9. The radially compressive implant of claim 8, wherein:
the transition of the implant from the natural shape to the insertion shape includes the first transition section, the second transition section, and the third transition section being deformable to store energy whereby the first transition section, the second transition section, and the third transition section move the bridge from the natural form to the insertion form, further whereby the first transition section moves the first screw, the second transition section moves the second screw, and the third transition section moves the third screw away from the central axis such that the first screw, the second screw, and the third screw diverge relative to the central axis as the first screw, the second screw, and the third screw progress from the natural position to the insertion position thereby facilitating the implant storing energy deliverable radially relative to the central vertical axis; and the transition of the implant from the insertion shape toward the natural shape includes the first transition section, the second transition section, and the third transition section delivering the energy stored therein whereby the first transition section, the second transition section, and the third transition section move the bridge from the insertion form toward the natural form, further whereby the first transition section moves the first screw, the second transition section moves the second screw, and the third transition section moves the third screw toward the central axis such that the first screw, the second screw, and the third screw converge relative to the central axis as the first screw, the second screw, and the third screw progress from the insertion position toward the natural position thereby facilitating the implant delivering the energy stored therein radially relative to the central vertical axis.

10. The radially compressive implant of claim 1, the implant, comprising:
the bridge, comprising:
a fourth bridge segment extending from the center section to an end thereof, the fourth bridge segment including an opening adjacent the end thereof,
a fifth bridge segment extending from the center section to an end thereof, the fifth bridge segment including an opening adjacent the end thereof, whereby the first bridge segment, the second bridge segment, the third bridge segment, the fourth bridge segment, and the fifth bridge segment are spaced symmetrically about the central vertical axis of the implant,
a fourth transition section located in the fourth bridge segment between the center section and the opening of the fourth bridge segment, and
a fifth transition section located in the fifth bridge segment between the center section and the opening of the fifth bridge segment;

a fourth fixation member insertable through the opening of the fourth bridge segment at the end thereof;

a fifth fixation member insertable through the opening of the fifth bridge segment at the end thereof; and the implant being transitionable between the natural shape and the insertion shape, wherein:

the transition of the implant from the natural shape to the insertion shape includes the first transition section, the second transition section, the third transition section, the fourth transition section, and the fifth transition section being deformable to store energy whereby the first transition section, the second transition section, the third transition section, the fourth transition section, and the fifth transition section move the bridge from the natural form to the insertion form, further whereby the first transition section moves the first fixation member, the second transition section moves the second fixation member, the third transition section moves the fourth fixation member, the fourth transition section moves the fourth fixation member, and the fifth transition section moves the fifth fixation member away from the central axis such that the first fixation member, the second fixation member, the third fixation member, the fourth fixation member, and the fifth fixation member diverge relative to the central axis as the first fixation member, the second fixation member, the third fixation member, the fourth fixation member, and the fifth fixation member progress from the natural position to the insertion position thereby facilitating the implant storing energy deliverable radially relative to the central vertical axis, and the transition of the implant from the insertion shape toward the natural shape includes the first transition section, the second transition section, the third transition section, the fourth transition section, and the fifth transition section delivering the energy stored therein whereby the first transition section, the second transition section, the third transition section, the fourth transition section, and the fifth transition section move the bridge from the insertion form toward the natural form, further whereby the first transition section moves the first fixation member, the second transition section moves the second fixation member, the third transition section moves the third fixation member, the fourth transition section, and the fifth transition section moves the fifth fixation member toward the central axis such that the first fixation member, the second fixation member, the third fixation member, the fourth fixation member, and the fifth fixation member converge relative to the central axis as the first fixation member, the second fixation member, the third fixation member, the fourth fixation member, and the fifth fixation member progress from the insertion position toward the natural position thereby facilitating the implant delivering the energy stored therein radially relative to the central vertical axis.

11. The radially compressive implant of claim 10, wherein the fourth bridge segment and the fifth bridge segments at the ends thereof each define an interlock adapted along with the interlocks of the first bridge segment, the second bridge segment, and the third bridge segment to facilitate engagement of the implant with an implant delivery device.

12. A radially compressive implant, comprising:

a bridge including a central vertical axis, the bridge, comprising:

a center section, a first bridge segment extending from the center section to an end thereof, the first bridge segment including an opening adjacent the end thereof, a second bridge segment extending from the center section to an end thereof, the second bridge segment including an opening adjacent the end thereof, a third bridge segment extending from the center section to an end thereof, the third bridge segment including an opening adjacent the end thereof, a first transition section located in the first bridge segment between the center section and the opening of the first bridge segment, a second transition section located in the second bridge segment between the center section and the opening of the second bridge segment, and a third transition section located in the third bridge segment between the center section and the opening of the third bridge segment;

a first fixation member inserted through the opening of the first bridge segment at the end thereof;

a second fixation member inserted through the opening of the second bridge segment at the end thereof;

a third fixation member inserted through the opening of the third bridge segment at the end thereof; and the implant being transitionable between a natural shape and an insertion shape, wherein:

a transition of the implant from the natural shape to the insertion shape includes the first transition section, the second transition section, and the third transition section being deformable to store energy whereby the first transition section, the second transition section, and the third transition section move the bridge from a natural form to an insertion form, further whereby the first transition section moves the first fixation member, the second transition section moves the second fixation member, and the third transition section moves the third fixation member away from the central axis such that the first fixation member, the second fixation member, and the third fixation member diverge relative to the central axis as the first fixation member, the second fixation member, and the third fixation member progress from a natural position whereby the first fixation member, the second fixation member, and the third fixation member reside from the central vertical axis at a first angle measured from a plane perpendicular to the central vertical axis to an insertion position whereby the first fixation member, the second fixation member, and the third fixation member reside from the central vertical axis at a second angle measured from the plane perpendicular to the central vertical axis that is greater than the first angle thereby facilitating the implant storing energy deliverable radially relative to the central vertical axis, and a transition of the implant from the insertion shape toward the natural shape includes the first transition section, the second transition section, and the third transition section delivering the energy stored therein whereby the first transition section, the second transition section, and the third transition section move the bridge from the insertion form toward the natural form, further whereby the first transition section moves the first fixation member, the second transition section moves the second fixation member, and the third transition section moves the third fixation member toward the central axis such that the first fixation member, the second fixation member, and the third fixation member converge relative to the central axis as the first fixation member, the second fixation member, and the third fixation member progress from the insertion position toward the natural position thereby facilitating the implant delivering the energy stored therein radially relative to the central vertical axis.

13. The radially compressive implant of claim 12, wherein the first bridge segment, the second bridge segment, and the third bridge segment radially extend from the center section and are spaced symmetrically about the central vertical axis of the implant.

14. The radially compressive implant of claim 12, wherein the first bridge segment, the second bridge segment, and the third bridge segment are dimensionally identical.

15. The radially compressive implant of claim 12, wherein the first fixation member, the second fixation member, and the third fixation member are spaced symmetrically about the central vertical axis of the implant in both the natural position and the insertion position.

16. The radially compressive implant of claim 12, wherein:
the first fixation member, the second fixation member, and the third fixation member in the natural position reside from the central vertical axis at a first distance; and
the first fixation member, the second fixation member, and the third fixation member in the insertion position reside from the central vertical axis at a second distance that is greater than the first distance.

17. The radially compressive implant of claim 12, wherein the bridge defines an aperture at the central vertical axis of the implant.

18. The radially compressive implant of claim 12, wherein the first bridge segment, the second bridge segment, and the third bridge segment at the ends thereof each define an interlock adapted to facilitate engagement of the implant with an implant delivery device.

19. The radially compressive implant of claim 12, wherein:
the first fixation member comprises a first screw inserted through the opening of the first bridge segment at the end thereof;
the second fixation member comprises a second screw inserted through the opening of the second bridge segment at the end thereof; and
the third fixation member comprises a third screw inserted through the opening of the third bridge segment at the end thereof.

20. The radially compressive implant of claim 19, wherein:
the transition of the implant from the natural shape to the insertion shape includes the first transition section, the second transition section, and the third transition section being deformable to store energy whereby the first transition section, the second transition section, and the third transition section move the bridge from the natural form to the insertion form, further whereby the first transition section moves the first screw, the second transition section moves the second screw, and the third transition section moves the third screw away from the central axis such that the first screw, the second screw, and the third screw diverge relative to the central axis as the first screw, the second screw, and the third screw progress from the natural position to the insertion position thereby facilitating the implant storing energy deliverable radially relative to the central vertical axis; and
the transition of the implant from the insertion shape toward the natural shape includes the first transition section, the second transition section, and the third transition section delivering the energy stored therein whereby the first transition section, the second transition section, and the third transition section move the bridge from the insertion form toward the natural form, further whereby the first transition section moves the first screw, the second transition section moves the second screw, and the third transition section moves the third screw toward the central axis such that the first screw, the second screw, and the third screw converge relative to the central axis as the first screw, the second screw, and the third screw progress from the insertion position toward the natural position thereby facilitating the implant delivering the energy stored therein radially relative to the central vertical axis.

21. The radially compressive implant of claim 12, the implant, comprising:
the bridge, comprising:
a fourth bridge segment extending from the center section to an end thereof, the fourth bridge segment including an opening adjacent the end thereof,
a fifth bridge segment extending from the center section to an end thereof, the fifth bridge segment including an opening adjacent the end thereof, whereby the first bridge segment, the second bridge segment, the third bridge segment, the fourth bridge segment, and the fifth bridge segment are spaced symmetrically about the central vertical axis of the implant,
a fourth transition section located in the fourth bridge segment between the center section and the opening of the fourth bridge segment, and
a fifth transition section located in the fifth bridge segment between the center section and the opening of the fifth bridge segment;
a fourth fixation member insertable through the opening of the fourth bridge segment at the end thereof;
a fifth fixation member insertable through the opening of the fifth bridge segment at the end thereof; and
the implant being transitionable between the natural shape and the insertion shape, wherein:
the transition of the implant from the natural shape to the insertion shape includes the first transition section, the second transition section, the third transition section, the fourth transition section, and the fifth transition section being deformable to store energy whereby the first transition section, the second transition section, the third transition section, the fourth transition section, and the fifth transition section move the bridge from the natural form to the insertion form, further whereby the first transition section moves the first fixation member, the second transition section moves the second fixation member, the third transition section moves the fourth fixation member, the fourth transition section moves the fourth fixation member, and the fifth transition section moves the fifth fixation member away from the central axis such that the first fixation member, the second fixation member, the third fixation member, the fourth fixation member, and the fifth fixation member diverge relative to the central axis as the first fixation member, the second fixation member, the third fixation member, the fourth fixation member, and the fifth fixation member progress from the natural position to the insertion position thereby facilitating the implant storing energy deliverable radially relative to the central vertical axis, and the transition of the implant from the insertion shape toward the natural shape includes the first transition section, the second transition section, the third transition section, the fourth transition section, and the fifth transition section delivering the energy stored therein whereby the first transition section, the second transition section, the third transition section, the fourth transition section, and the fifth transition section move the bridge from the insertion form toward the natural form, further whereby the first transition section moves the first fixation member, the second transition section moves the second fixation member, the third transition section moves the third fixation member, the fourth transition section, and the fifth transition section moves the fifth fixation member toward the central axis such that the first fixation member, the second fixation member, the third fixation member, the fourth fixation member, and the fifth fixation member converge relative to the central axis as the first fixation member, the second fixation member, the third fixation member, the fourth fixation member, and the fifth fixation member progress from the insertion position toward the natural position thereby facilitating the implant delivering the energy stored therein radially relative to the central vertical axis.

22. The radially compressive implant of claim 21, wherein the first bridge segment, the second bridge segment, the third bridge segment, the fourth bridge segment, and the fifth bridge segments at the ends thereof each define an interlock adapted to facilitate engagement of the implant with an implant delivery device.

\* \* \* \* \*